United States Patent [19]

Dininno et al.

[11] Patent Number: 5,336,674

[45] Date of Patent: * Aug. 9, 1994

[54] 2-PHENANTHRIDINYL CARBAPHENEM ANTIBACTERIAL AGENT

[75] Inventors: Frank P. Dininno, Old Bridge; Mark L. Greenlee, Rahway; Thomas A. Rano, Somerville, all of N.J.; Wendy Lee, Chicago, Ill.

[73] Assignee: Merck & Co., Inc., Rahway, N.J.

[ * ] Notice: The portion of the term of this patent subsequent to Jul. 12, 2011 has been disclaimed.

[21] Appl. No.: 9,626

[22] Filed: Jan. 27, 1993

[51] Int. Cl.$^5$ ................ C07D 487/00; A61K 31/395; A01N 43/00
[52] U.S. Cl. ..................................... 514/210; 540/302
[58] Field of Search ......................... 540/302; 514/210

[56] References Cited

U.S. PATENT DOCUMENTS

| 4,260,627 | 4/1981 | Christensen et al. ............... 424/274 |
| 4,465,632 | 8/1984 | Christensen et al. ............ 260/245.2 |
| 4,543,257 | 9/1985 | Cama et al. ........................ 514/210 |
| 4,978,659 | 8/1989 | Salzmann et al. . |
| 5,004,739 | 4/1991 | Salzmann et al. . |
| 5,004,740 | 4/1991 | Salzmann et al. . |
| 5,006,519 | 4/1991 | DiNinno et al. . |
| 5,011,832 | 4/1991 | Salzmann et al. . |
| 5,035,385 | 7/1991 | DiNinno et al. . |
| 5,037,820 | 8/1991 | DiNinno et al. . |
| 5,132,422 | 7/1992 | DiNinno et al. . |
| 5,153,185 | 10/1992 | DiNinno et al. . |
| 5,157,033 | 10/1992 | DiNinno et al. . |
| 5,162,314 | 11/1992 | DiNinno et al. . |

FOREIGN PATENT DOCUMENTS 0277743 8/1988 European Pat. Off. .
0444889 2/1991 European Pat. Off. .

OTHER PUBLICATIONS

L. D. Cama et al., Total Synthesis of Theinamycn Analgos-III, Tetrahedron 39, 2531 (1983).
R. N. Guthikonda et al., Structure Activity Relationships in the 2-Arylcarbapenem Series, J. Med. Chem., 30, 871 (1987).

Primary Examiner—Marianne M. Cintins
Assistant Examiner—Rebecca Cook
Attorney, Agent, or Firm—David A. Muthard; Mark D. Daniel; Joseph F. DiPrima

[57] ABSTRACT

The present invention relates to antibacterial agents of the carbapenem class, in which the 2-position sidechain is characterized by a phenanthridine moiety typically having a substituent attached to the nitrogen of the phenanthridine and substituted at other positions by various neutral substituents. When there is substitution on the nitrogen of the phenathridine moiety that nitrogen is a charged quaternary nitrogen.

19 Claims, No Drawings

2-PHENANTHRIDINYL CARBAPHENEM ANTIBACTERIAL AGENT

BACKGROUND OF THE INVENTION

The present invention relates to antibacterial agents of the carbapenem class, in which the 2-position sidechain is characterized by a phenanthridine moiety having a substituent on the nitrogen and substituted by various neutral substituents, as described in more detail further below.

Thienamycin was an early carbapenem antibacterial agent having a broad spectrum; it has the following formula:

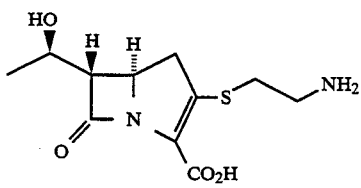

Later, N-formimidoyl thienamycin was discovered; it has the formula:

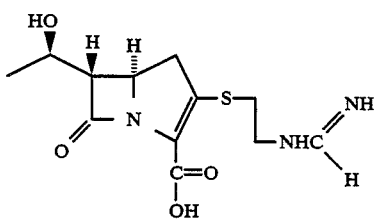

The 2-phenanthridinyl-carbapenems of the present invention are not characterized by an antibacterial spectrum such as that of thienamycin or N-formimidoyl thienamycin. Rather, their spectrum of activity includes gram positive microorganisms, especially methicillin resistant *Staphylococcus aureus* (MRSA), methicillin resistant *Staphylococcus epidermidis* (MRSE), and methicillin resistant coagulase negative Stapphylococci (MRCNS). The antibacterial compounds of the present invention thus comprise an important contribution to therapy of these difficult to control pathogens. Moreover, there is an increasing need for agents effective against such pathogens (MRSA/MRCNS) which are at the same time safe, i.e., free from undesirable toxic side effects. No β-lactam antibacterial has yet been found which meets these requirements. And, the current agent of choice, vancomycin, a glycopeptide antibacterial, is experiencing an ever increasing amount of resistance in the MRSA/MRCNS pathogens.

More recently, carbapenem antibacterial agents have been described which have a 2-substituent which is an aryl moiety optionally substituted by, e.g., aminomethyl and substituted aminomethyl. These agents are described in U.S. Pat. Nos. 4,543,257 and 4,260,627 and have the formula:

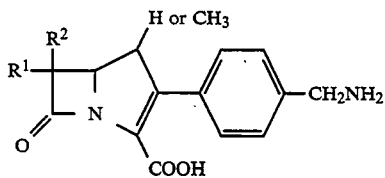

However, there is no description or suggestion of a phenanthridinyl 2-substituent such as characterizes the compounds of the present invention, nor is there any suggestion of the surprisingly better anti-MRSA/MRCNS activity of the compounds of the present invention.

EP-A-0277 743 describes a particular class of compounds of the formula:

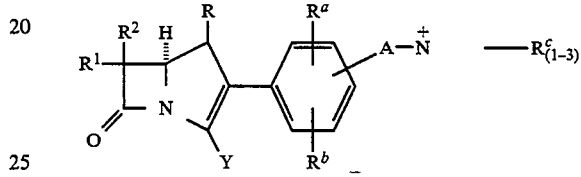

but this limited teaching in no way suggests the totally different compounds of the present invention, nor their surprisingly better anti-MRSA/MRCNS activity.

SUMMARY OF THE INVENTION

The present invention provides novel carbapenem compounds of the formula:

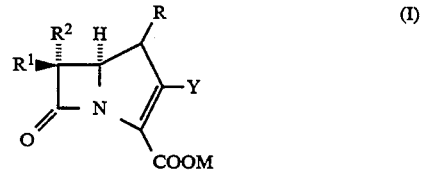

wherein
Y is a) 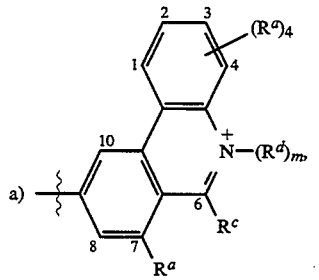

b) 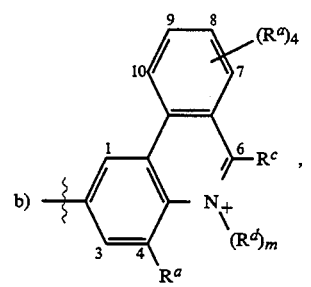

-continued

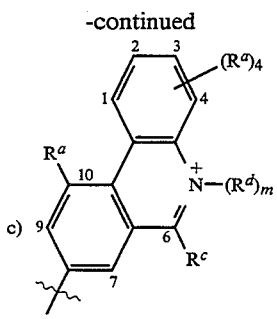

or

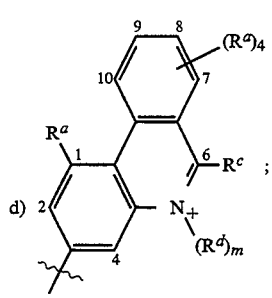

R is H or $CH_3$;

$R^1$ and $R^2$ are independently H, $CH_3$—, $CH_3CH_2$—, $(CH_3)_2CH$—, $HOCH_2$—, $CH_3CH(OH)$—, $(CH_3)_2C(OH)$—, $FCH_2CH(OH)$—, $F_2CHCH(OH)$—, $F_3CCH(OH)$—, $CH_3CH(F)$—, $CH_3CF_2$—, or $(CH_3)_2C(F)$—;

$R^a$ are independently selected from the group consisting of hydrogen and the radicals set out below, provided that not more than four $R^a$ radicals are other than hydrogen:

a) a trifluoromethyl group: —$CF_3$;
b) a halogen atom: —Br, —Cl, —F, or —I;
c) $C_1$-$C_4$ alkoxy radical: —$OC_{1-4}$ alkyl, wherein the alkyl is optionally mono-substituted by $R^q$, where $R^q$ is a member selected from the group consisting of —OH, —$OCH_3$, —CN, —C(O)$NH_2$, —OC(O)$NH_2$, CHO, —OC(O)N($CH_3$)$_2$, —$SO_2NH_2$, —$SO_2N(CH_3)_2$, —$SOCH_3$, —$SO_2CH_3$, —F, —$CH_3$, —$COOM^a$ (where $M^a$ is hydrogen, alkali metal, methyl or phenyl), tetrazolyl (where the point of attachment is the carbon atom of the tetrazole ring and one of the nitrogen atoms is mono-substituted by $M^a$ as defined above) and —$SO_3M^b$ (where $M^b$ is hydrogen or an alkali metal);

d) a hydroxy group: —OH;
e) a carbonyloxy radical: —O(C=O)$R^s$, where $R^s$ is $C_{1-4}$ alkyl or phenyl, each of which is optionally mono-substituted by $R^q$ as defined above;

f) a carbamoyloxy radical: —O(C=O)N($R^y$)$R^z$ where $R^y$ and $R^z$ are independently H, $C_{1-4}$ alkyl (optionally mono-substituted by $R^q$ as defined above), together a 3- to 5-membered alkylidene radical to form a ring (optionally substituted with $R^q$ as defined above) or together a 2- to 4-membered alkylidene radical, interrupted by —O—, —S—, —S(O)— or —S(O)$_2$— to form a ring (where the ring is optionally mono-substituted with Rq as defined above);

g) a sulfur radical: —$S(O)_n$—$R^s$ where n=0-2, and $R^s$ is defined above;
h) a sulfamoyl group: —$SO_2$N($R^y$)$R^z$ where $R^y$ and $R^z$ are as defined above;
i) azido: $N_3$
j) a formamido group: —N($R^t$)(C=O)H, where $R^t$ is H or $C_{1-4}$ alkyl, and the alkyl thereof is optionally mono-substituted by $R^q$ as defined above;
k) a ($C_1$-$C_4$ alkyl)carbonylamino radical: —N($R^t$)(C=O)$C_{1-4}$ alkyl, where $R^t$ is as defined above, and the alkyl group is also optionally mono-substituted by $R^q$ as defined above;
l) a ($C_1$-$C_4$ alkoxy) carbonylamino radical: —N($R^t$)(C=O)O$C_{1-4}$ alkyl, where $R^t$ is as defined above, and the alkyl group is also optionally mono-substituted by $R^q$ as defined above;
m) a ureido group: —N($R^t$)(C=O)N($R^y$)$R^z$ where $R^t$, $R^y$ and $R^z$ are as defined above;
n) a sulfonamido group: —N($R^t$)$SO_2R_s$, where $R^s$ and $R^t$ are as defined above;
o) a cyano group: —CN;
p) a formyl or acetalized formyl radical: —(C=O)H or —CH(OCH$_3$)$_2$;
q) ($C_1$-$C_4$ alkyl)carbonyl radical wherein the carbonyl is acetalized: —C(OCH$_3$)$_2$$C_{1-4}$ alkyl, where the alkyl is optionally mono-substituted by $R^q$ as defined above;
r) carbonyl radical: —(C=O)$R^s$, where $R^s$ is as defined above;
s) a hydroximinomethyl radical in which the oxygen or carbon atom is optionally substituted by a $C_1$-$C_4$ alkyl group: —(C=NOR$^z$)$R^y$ where $R^y$ and $R^z$ are as defined above, except they may not be joined together to form a ring;
t) a ($C_1$-$C_4$ alkoxy)carbonyl radical: —(C=O)O$C_{1-4}$ alkyl, where the alkyl is optionally mono-substituted by $R^q$ as defined above;
u) a carbamoyl radical: —(C=O)N($R^y$)$R^z$ where $R^y$ and $R^z$ are as defined above;
v) an N-hydroxycarbamoyl or N($C_1$-$C_4$ alkoxy)-carbamoyl radical in which the nitrogen atom may be additionally substituted by a $C_1$-$C_4$ alkyl group: —(C=O)—N(OR$^y$)$R^z$ where $R^y$ and $R^z$ are as defined above, except they may not be joined together to form a ring;
w) a thiocarbamoyl group: —(C=S)N($R^y$)($R^z$) where $R^y$ and $R^z$ are as defined above;
x) carboxyl: —$COOM^b$, where $M^b$ is as defined above;
y) thiocyanate: —SCN;
z) trifluoromethylthio: —$SCF_3$;
aa) tetrazolyl, where the point of attachment is the carbon atom of the tetrazole ring and one of the nitrogen atoms is mono-substituted by hydrogen, an alkali metal or a $C_1$-$C_4$ alkyl optionally substituted by $R^q$ as defined above;
ab) an anionic function selected from the group consisting of: phosphono [P=O(O$M^b$)$_2$]; alkylphosphono {P=O(O$M^b$)-[O($C_1$-$C_4$ alkyl)]}; alkylphosphinyl [P=O(O$M^b$)-($C_1$-$C_4$ alkyl)]; phosphoramido [P=O(O$M^b$)N($R^y$)$R^z$ and P=O-(O$M^b$)NHR$^x$]; sulfino (SO$_2M^b$); sulfo (SO$_3M^b$); acylsulfonamides selected from the structures CON$M^b$SO$_2R^x$, CON$M^b$SO$_2$N($R^y$)$R^z$, SO$_2$N$M^b$CON($R^y$)$R^z$; and SO$_2$N$M^b$CN, where $R^x$ is phenyl or heteroaryl, where heteroaryl is a monocyclic aromatic hydrocarbon group having 5 or 6 ring atoms, in which a carbon atom is the point of attachment, in which one of the carbon atoms has been replaced by a nitrogen atom, in which one additional carbon atom is optionally replaced by a heteroatom selected from O or S, and in which from 1 to 2 additional carbon atoms are optionally replaced by a nitrogen heteroatom, and where the phenyl and heteroaryl are optionally mono-substituted by $R^q$, as defined above; $M^b$ is as defined above; and $R^y$ and $R^z$ are as defined above;

ac) $C_5$-$C_7$ cycloalkyl group in which one of the carbon atoms in the ring is replaced by a heteroatom selected from O, S, NH or N($C_1$-$C_4$ alkyl) and in which one additional carbon atom may be replaced by NH or N($C_1$-$C_4$ alkyl), and in which at least one carbon atom adjacent to each nitrogen heteroatom has both of its attached hydrogen atoms replaced by one oxygen thus forming a carbonyl moiety and there are one or two carbonyl moieties present in the ring;

ad) $C_2$-$C_4$ alkenyl radical, optionally mono-substituted by one of the substituents a) to ac) above and phenyl which is optionally substituted by $R^q$ as defined above;

ae) $C_2$-$C_4$ alkynyl radical, optionally mono-substituted by one of the substituents a) to ac) above;

af) $C_1$-$C_4$ alkyl radical;

ag) $C_1$-$C_4$ alkyl mono-substituted by one of the substituents a)-ac) above;

ah) a 2-oxazolidinonyl moiety in which the point of attachment is the nitrogen atom of the oxazolidinone ring, the ring oxygen atom is optionally replaced by a heteroatom selected from —S— and $NR^t$ (where $R^t$ is as defined above) and one of the saturated carbon atoms of the oxazolidinone ring is optionally mono-substituted by one of the substituents a) to ag) above;

ai) an amine group: —$NR^eR^f$, where $R^e$ and $R^f$ are independently H, $C_{1-4}$ alkyl (optionally mono-substituted by $R^q$ as defined above), together a 4- to 5-membered alkylidene radical to form a ring (optionally substituted with $R^q$ as defined above);

$R^c$ is selected from the group consisting of hydrogen and the radicals set out below:

ba) $C_1$-$C_4$ alkyl radical;

bb) $C_1$-$C_4$ alkyl mono-substituted by one of the substituents a)-ac) described hereinabove;

bc) $C_1$-$C_4$ alkoxy radical: —$OC_{1-4}$ alkyl, wherein the alkyl is optionally mono-substituted by $R^q$, where $R^q$ is as described hereinabove; and bd) an amine group: —$NR^gR^h$, where $R^g$ and $R^h$ are independently H, $C_{1-4}$ alkyl (optionally mono-substituted by $R^q$ as defined above), together a 4- to 5-membered alkylidene radical to form a ring (optionally substituted with $R^q$ as defined above) or $R^g$ is combined with $R^d$ to form a diradical selected from the group consisting of: —$CH_2CH_2$—, —$CH_2CH_2CH_2$— and —CH=CH—;

$R^d$ is —$NH_2$, —$O^-$, $C_1$-$C_4$-alkyl (where the alkyl group is optionally monosubstituted with $R^q$ as defined above), or hydrogen, or $R^d$ is combined with $R^g$ to form a diradical selected from the group consisting of: —$CH_2CH_2$—, —$CH_2CH_2CH_2$— and —CH=CH—;

provided that $R^d$ is hydrogen only if at least one $R^a$ or $R^c$ is an amine group;

m is 0 or 1, if at least one $R^a$ or $R^c$ is an amine group;

m is 1 if neither $R^a$ nor $R^c$ is an amine group; and

M is selected from:
i) hydrogen;
ii) a pharmaceutically acceptable esterifying group or removable carboxyl protecting group;
iii) an alkali metal or other pharmaceutically acceptable cation; or
iv) a negative charge.

DETAILED DESCRIPTION OF THE INVENTION

The manufacture of compounds of Formula I may be carried out in a three-stage synthesis scheme followed by a final step which allows for the removal of any protecting groups. The objective of the first synthetic stage is to produce a base phenanthridine compound which may be converted to the two-position substituent of the carbapenem of Formula I. The objective of the second synthetic stage is to attach the base phenanthridine to the carbapenem. Finally, the objective of the third synthetic stage is to substitute the phenanthridine with the desired $R^a$. This third synthetic stage may be performed after the first synthetic stage or during or after the second synthetic stage according to the nature of the various $R^a$.

Flow Sheets A-E demonstrate alternative first stage syntheses. Flow Sheet F demonstrates a second stage synthesis. The third synthesis varies according to the selected $R^a$.

Referring to Flow Sheet A, 2-bromophenanthridine A1, obtained by bromination of phenanthridine, was modified to the trimethylstannylphenanthridine A2. This is accomplished by reacting A1 with hexamethylditin in the presence of a palladium (O) catalyst such as tetrakis(triphenylphosphine)palladium and the like, and a phosphine, such as triphenylphosphine and the like, in a solvent such as toluene at an elevated temperature. The intermediate A2 may be incorporated in the synthesis of the compounds of the instant invention or it may be further modified.

Thus, the trimethylstannyl phenanthridine A2 may be oxidized by reacting A2 with an oxidizing agent such as m-chloroperbenzoic acid (MCPBA), magnesium monoperoxyphthalate (MMPP) and the like, optionally in the presence of a base such as sodium bicarbonate and the like.

Alternatively, the phenanthridinine A2 may be alkylated with a suitable alkylating agent, such as methyl triflate, ethyl triflate, and the like, in a suitable solvent, such as methylene chloride, tetrahydrofuran and the like. This alkylated compound A4 may then be incorporated in the synthesis of the compounds of the instant invention.

Also, the nitrogen atom of the phenanthridine A2 may be substituted with an amine group by reacting A2 with O-mesitylene sulfonylhydroxylamine (Y. Tamura, J. Minamikawa, M. Ikeda; *Synthesis,* 1977, 1–17) and the like, to provide the phenanthridine A5.

The N-oxide A3 may be methylated to provide phenanthridine A6. Intermediate A6 may be reacted with a nucleophilic reagent, such as sodium cyanide, potassium cyanide, sodium methoxide, ammonia, methylamine and the like to provide the phenanthridine A7 having a substituent in the 6-position ($R^c$ is —$OCH_3$, —$NH_2$, —$NHCH_3$, —$N(CH_3)_2$, —CN, and the like) (L. Stephenson and W. K. Warburton, *J. Chem. Soc. (C),* 1355(1970)). Such an intermediate A7 may then be substituted on the ring nitrogen by a method described hereinabove.

FLOW SHEET A

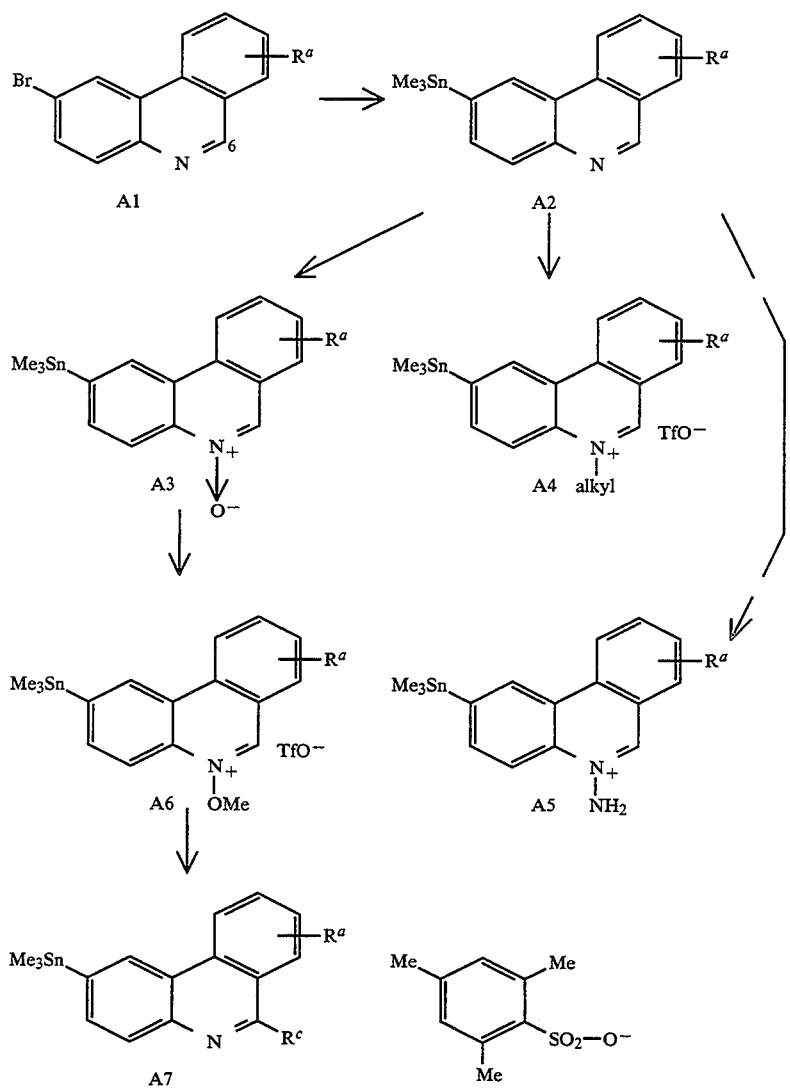

Alternatively, if the substitution pattern is not accessible from a commercially available phenanthridine, the substituted phenanthridine may be constructed from monocyclic components. Referring to Flow Sheets B and C this alternative synthesis can be generally described as a directed ortho metallation reaction to prepare starting materials required for a Suzuki cross-coupling reaction, ring closure to produce a suitably substituted phenanthridone and subsequent reductive dehalogenation to produce the desired phenanthridine platform. The first part of this suggested synthesis is utilized to produce similar phenanthridone and phenanthridine compounds by Snieckus, V., *Chem. Rev.* 1990, 90, 879–933; Fu. J. M. and Snieckus, V., *Tetrahedron Lett.* 1990, 31, p. 1665; Siddiqui, M. A., et al., *Tetrahedron Lett.*, Vol. 29, No. 43, 5463–5466 (1988); Mills, R. J., et al., *J. Org. Chem.*, 1989, 54, 4372–4385; Mills, R. J., *J. Org. Chem.*, 1989, 54, 4386–4390; and Suzuki, A., et al., *Synthetic Communications*, 11(7), 513–519 (1981).

Referring to Flow Sheet B, compound B-1, which has as a substituent a directed metallation group (DMG), is utilized by methods according to Snieckus, et al., above. The function of the directed metallation group (DMG) is to orchestrate adornment of the aromatic ring. It is highly desirable of the DMG that it also provide a precursor substituent for the necessary carboxy function or amino function forming the amide linkage of the object phenanthridone or the imine function of the object phenanthridine. Suitable DMG to serve as a carboxyl precursor are secondary and tertiary amides and oxazolino groups. Specifically, these precursors may be, for example, —CONEt$_2$, —CONHMe, 4,4-dimethyl-2-oxazolinyl, and the like. In the instance of compound B-1, DMG is of the carboxyl precursor type. Suitable DMG to serve as an amino precursor are protected primary and secondary amines. Specifically, these precursors may be —NH-tert-butoxycarbonyl (—NH-t-Boc), —NH-pivaloyl, phenylsulfonamido, and the like. Compound C-1 as described below is by way of example, substituted by a DMG of the amino precursor type.

As the first step of Flow Sheet B, the bromine of compound B-1 is protected through silylation via halogen metal exchange in the presence of TMS chloride at between about −100° to −50° C. to produce aryl silane B-2. Incorporation of an ortho substituent $R^a$ or its appropriate precursor may be made on compound B-2 in accordance with standard directed metallation procedures described by Snieckus, et al., above. The resultant substituted aryl silane B-3 is ortho metallated and treated with an appropriate boron containing electrophile to obtain the requisite aryl boronic acid B-4. Suitable boron containing electrophiles include lower alkyl borates, such as trimethyl borate and tri-i-propyl borate. Alternatively, and not shown in the Flow Sheets, the ortho metallated compound may be treated with electrophiles such as trialkyltin halides providing the corresponding aryl stannanes which in turn are also useful intermediates in the production of biphenyls as reported by Stille, et al., *J. Am. Chem. Soc.*, 1987, Vol. 109, page 5478–5486. Preparation of biphenyl intermediate B-6 is accomplished in the Flow Sheets utilizing the Suzuki cross-coupling procedure and the appropriately adorned aryl compounds B-4 and B-5. The Suzuki coupling can be generally described as the reaction of an aryl boronic acid with an aryl halide or halide equivalent employing tetrakis(triphenylphosphine) palladium(O) catalyst in the presence of an aqueous solution of sodium carbonate in the solvents toluene/ethanol. The resulting biphenyl compound is isolated by standard methods. Compound B-5 may itself be produced by standard methods to obtain the halogen substitution, X', the amino moiety —NR'$_2$ and the desired substituents $R^a$ or their precursors. The preferred halogen X' is bromine, iodine or the halogen equivalent trifluoromethanesulfonyloxy. The preferred amino moiety, —NR'$_2$, may be any of —NO$_2$, —N$_3$, protected amine or amine. Biphenyl compound B-6 is subsequently transformed into the halogenated biphenyl B-7 via ipso substitution of the trimethylsilyl moiety in methylene chloride or other appropriate solvent employing iodine monochloride. Any number of halogenating reagents are suitable such IBr, NBS, I$_2$, Br$_2$, etc., which must be compatible with the already existing functionalities. The halogenated phenanthridone B-8 is obtained via transamidation of the amino moiety with the latent carboxy precursor in the form of DMG. Alternatively, the phenanthridone may be formed via transamidation of a biphenyl compound such as B-6 and the ipso substitution of the halogen performed upon the trimethylsilyl- phenanthridone.

The phenanthridone B-8 is subsequently transformed into the corresponding trimethylstannyl phenanthridine B-10. Such a transformation may be accomplished by reacting the phenanthridone B-8 with a halogenating agent such as phosphorous pentachloride, phosphorous oxychloride and the like to provide the halogenated phenanthridine B-9 (where X" is the halogen). The halogenated phenanthridine B-9 may then be treated with hexamethylditin in the presence of tetrakis(triphenylphosphine)palladium (O) and triphenylphosphine to provide the phenanthridine B-10. Phenanthridine B-10 is subsequently transformed as described hereinabove, and illustrated in Flow Sheet A, to provide the quaternized phenanthridine B-11 (where Q⁻ is the counterion which is defined by the nature of the quaternizing agent).

Alternative syntheses of phenanthridones via a Beckmann Rearrangement are described by E. C. Horning et al. *J. Am. Chem. Soc.*, 5153 (1952); H. L. Pan and T. L. Fletcher, *J. Heterocyclic Chem.*, 7, 313 (1970); H. L. Pan and T. L. Fletcher, *J. Heterocyclic Chem.*, 7, 597 (1970); H. L. Pan and T. L. Fletcher, *J. Med Chem.*, 12, 822 (1969); and A. Guy and J. P. Guette, Synthesis, 222 (1980). One Such synthetic route is illustrated in Examples 11 and 12.

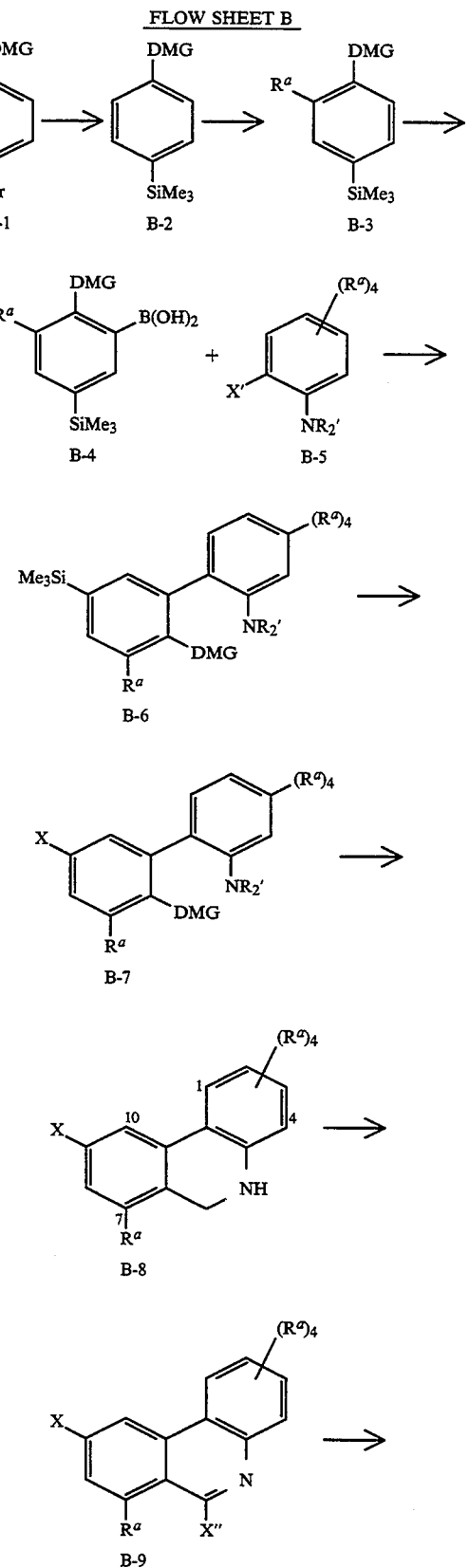

FLOW SHEET B

-continued
FLOW SHEET B

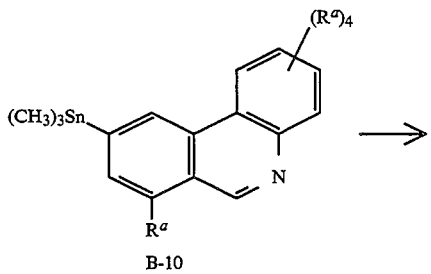
B-10

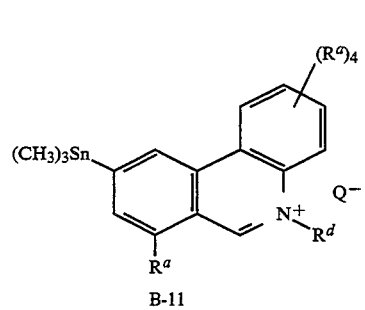
B-11

-continued
FLOW SHEET C

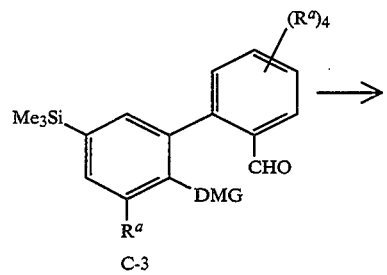
C-3

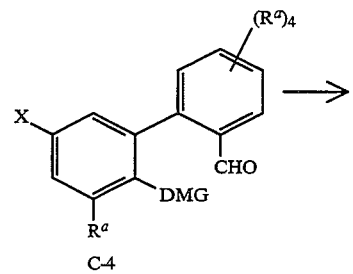
C-4

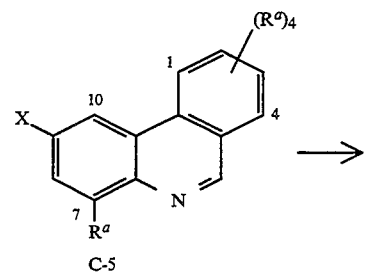
C-5

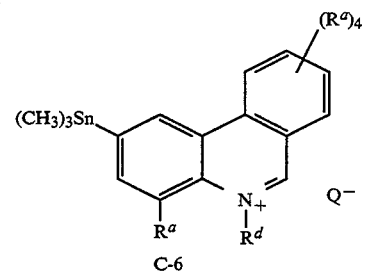
C-6

Referring to Flow Sheet C, the regioisomeric phenanthridine C-5, and subsequently the phenanthridine C-6, maybe produced in a manner analogous to that of phenanthridone B-8. Compound C1 is dissimilar to compound B-4 in that DMG of compound C1 is of the amino precursor type. Compound C1 is reacted with the appropriately adorned compound C2 to prepare biphenyl intermediate C3 utilizing the Suzuki cross-coupling procedure. As above biphenyl compound C3 is transformed into halogenated biphenyl C4 via ipso substitution and subsequently dehydrated to provide phenanthridine C5. Conversion of the phenanthridine C5 into the substituted phenanthridine C-6 may be accomplished by the method described herein above.

FLOW SHEET C

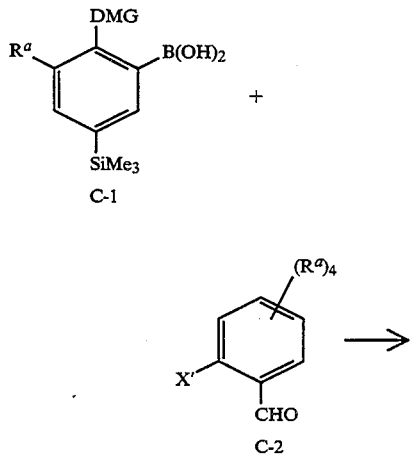

Referring to Flow Sheets D and E, the phenanthridine D-5 and phenanthridone E-5, having halogen group X in the 3-position (which will subsequently lead to attachment of the carbapenem nucleus at a different position on the phenanthridine moiety) may be similarly produced from starting materials analogous to those employed in Flow Sheet B and C.

Specifically referring to Flow Sheet D, compound D-1, wherein DMG represents an amino precursor and X' is a suitable leading group, may be derived from readily available compounds, such as 5-bromo-2-hydroxyaniline and the like. Compound D-1 is reacted with a suitably substituted phenyl boronic acid D-2 via a Suzuki cross-coupling procedure to form the biphenyl compound D-3. The silyl moiety on compound D-3 is then replaced with a suitable halogen, such as bromine or iodine via ipso substitution. The halogenated biphenyl D-4 then is cyclized to form the desired phenanthridine D-5. This phenanthridine may be subsequently converted to the trimethylstannyl phenanthridine by the methods described herein above.

FLOW SHEET D

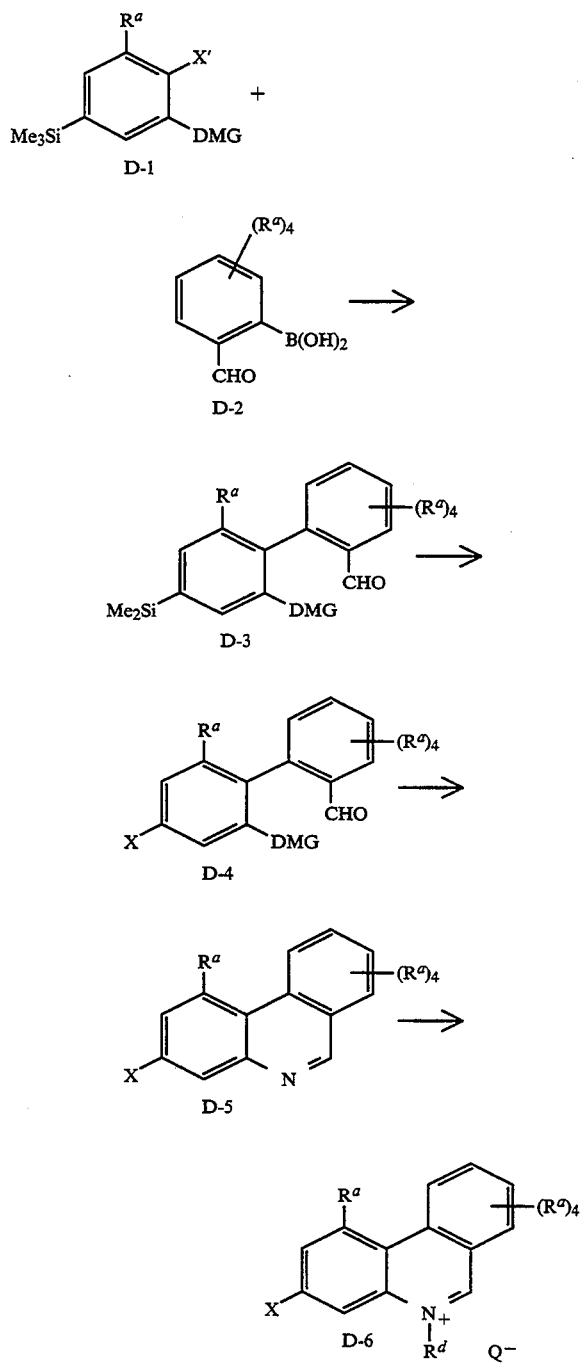

FLOW SHEET E

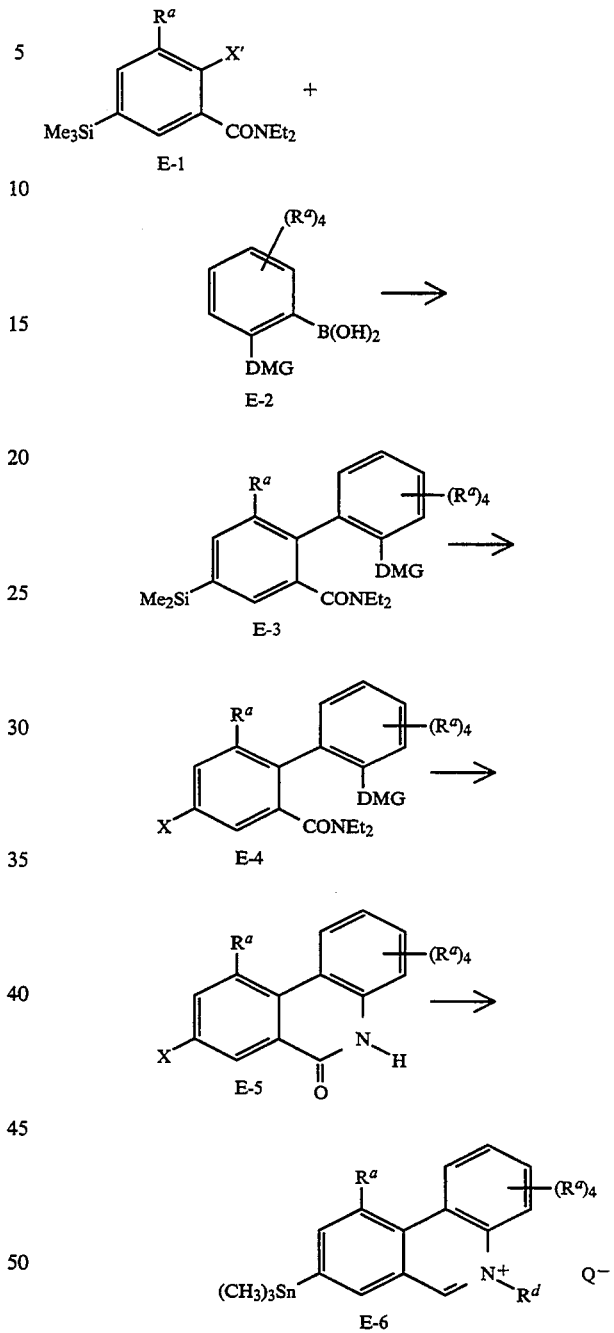

Specifically referring to Flow Sheet E, the starting material, compound E-1, may be derived from commercially available compounds, such as 5-bromo salicyclic acid and the like. Compound E-1 is reacted with the suitably substituted phenyl boronic acid E-2 via a Suzuki cross-coupling procedure to form the biphenyl compound E-3. The silyl moiety on Compound E-3 is transformed into a halogen moiety via ipso substitution. The halogenated biphenyl E-4 is then cyclized to form the phenanthridone E5 via transamidization. The phenanthridone intermediate may then be converted to the phenanthridine as previously described.

The object compounds of Flow Sheets A–E, the various regioisomeric phenanthridines, form the nucleus of the 2-position substitution of the carbapenem compounds taught herein. As such they are shown to be $R^a$ substituted. However, it is immediately clear to those skilled in the art that certain $R^a$ listed above, if substituted on B-3, B-5, or both (or the corresponding intermediates found in Flow Sheets A and C–E) would not survive or permit the synthesis to the phenanthridines. Thus, where a certain $R^a$ is desired, for example, on compound B-10 and this $R^a$ is not compatible with the synthesis scheme to produce B-10, then a compatible precursor substituent may be employed through the synthesis.

The identity of the precursor substituent employed is not crucial so long as it does not interfere with the synthesis to the phenanthridine and so long as it may be thereafter converted to more desireable substitution. Preferred precursor substituents are methyl, hydroxymethyl and protected hydroxymethyl.

Thus, for example as to the $R^a$ substituent on compound B-10, it may be an $R^a$ with or without protecting groups stable to the conditions of producing compound B-10 and stable to the conditions of subsequently adding B-10 to the carbapenem. Alternatively, it may be a stable precursor substituent which is stable to the conditions of making B-10, which is optionally stable to the conditions of adding B-10 to the carbapenem and which is convertible to a desired $R^a$ or to another precursor substituent.

As stated above, the second stage synthesis is to attach the base phenanthridine to the 2-position of the carbapenem.

Flow Sheet F shows a second stage synthesis, i.e. attachment of the base phenanthridine, such as B-11, to the 2-position of the carbapenem. This synthesis involves a palladium catalyzed cross-coupling reaction between a carbapenem triflate and a suitably substituted arylstannane, a process which is described in U.S. patent application No. 485,096 filed Feb. 26, 1990. Referring to Flow Sheet F, the 2-oxocarbapenam F-1 is reacted with a suitable trifluoromethanesulfonyl source, such as trifluoromethanesulfonic anhydride, trifluoromethanesulfonyl chloride and the like, in the presence of an organic nitrogen base, such as triethylamine, diisopropylamine and the like, in polar aprotic solvent, such as tetrahydrofuran or methylene chloride. The hydroxyl moiety may then be protected. Thus, optionally an organic nitrogen base, such as triethylamine and the like, is added to the reaction solution followed immediately by a silylating agent, such as trimethylsilyl trifluoromethanesulfonate or triethylsilyl triflate to provide intermediate F2 where $R^p$ is an alkyl silyl group. Regardless of whether the hydroxyl moiety is left unprotected or is modified with a protecting group, an aprotic polar coordinating solvent, such as DMF, 1-methyl-2-pyrrolidinone and the like, is then added. This is followed by the addition of a palladium compound, such as tris(dibenzylideneacetone)dipalladium chloroform, palladium acetate and the like, the stannane B-11 and optionally a suitably substituted phenylphosphine, such as tris(4-methoxyphenyl)phosphine, tris(2,4,6-trimethoxyphenyl)phosphine and the like. A halide source, such as lithium chloride, zinc chloride, tetrabutylammonium chloride, diisopropylamine hydrochloride, triethylamine hydrochloride and the like, is added and the reaction solution is allowed to warm and is stirred at a suitable temperature, such as 0° to 50° C. for from a few minutes to 7 days. The carbapenem F-3 is obtained by conventional isolation/purification methodology known in the art.

Generally speaking, the mild conditions of the synthesis shown in Flow Sheet F allow for a wide range of functional groups $R^a$ to be present. However, in certain cases it is advantageous for the $R^a$ substituent(s) of the stannane B-11 to be introduced in a protected or precursory form. Final elaboration of $R^a$ from a precursor substituent, e.g. hydroxymethyl, may be accomplished on carbapenem intermediate F-3. Removal of hydroxyl and carboxyl protecting groups then provides the final compound of Formula I. Such final elaboration and deprotection is described in further detail below.

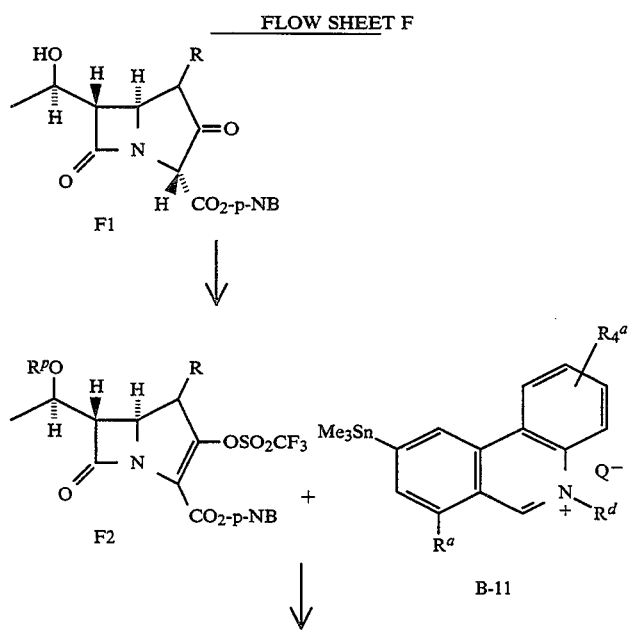

FLOW SHEET F

FLOW SHEET F

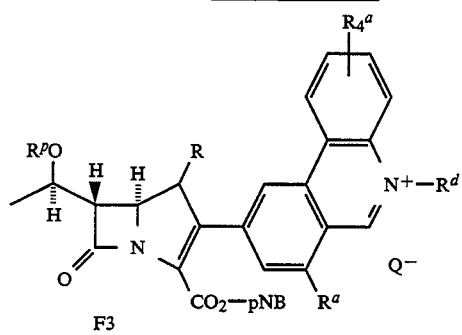

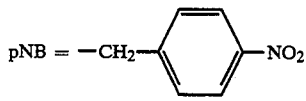

$R^p$ = H or —Si(alkyl)$_3$

The steps for preparing the 2-oxocarbapenam intermediate F-1 are well known in the art and are explained in ample detail by D. G. Melillo et al., *Tetrahedron Letters*, 21, 2783 (1980), T. Salzmann et al., *J. Am. Chem. Soc.*, 102, 6161 (1980), and L. M. Fuentes, I. Shinkai, and T. N. Salzmann, *J. Am. Chem. Soc.*, 108, 4675 (1986). The syntheses are also disclosed in U.S. Pat. Nos. 4,269,772, 4,350,631, 4,383,946 and 4,414,155 all assigned to Merck and Company, Inc.

The general synthesis description depicted above in the Flow Sheets $R^a$ shows a protected 1-hydroxyethyl substitution on the 6-position of the carbapenem. After final deprotection, a 1-hydroxyethyl substituent is obtained, which is preferred in most cases. However, it has been found that with certain 2-position-side-chain selections, the ultimate balance of favorable properties in the overall molecule may be enhanced by selection of the 6-(1-fluoroethyl) moiety instead. Preparation of 6-fluoroalkyl compounds within the scope of the present invention is carried out in a straightforward manner using techniques well known in the art of preparing carbapenem antibacterial compounds. See, e.g., J. G. deVries et al., *Heterocycles*, 23 (8), 1915 (1985); BE 900 718 A (Sandoz) and Japanese Patent Pub. No. 6-0163-882-A (Sanruku Ocean).

In preferred compounds of Formula I, $R^1$ is hydrogen. More preferably, $R^1$ is hydrogen and $R^2$ is (R)—CH$_3$CH(OH)— or (R)—CH$_3$CH(F)—. In the most preferred case, $R^1$ is hydrogen and $R^2$ is (R)—CH$_3$CH(OH)—. While R═H is usually preferred, there are instances in which R═CH$_3$ may provide improved chemical stability, water solubility, or pharmacokinetic behavior. The substituent R═CH$_3$ may be of either configuration, i.e., the α or β-stereoisomer. Additionally, in preferred compounds, at least one $R^a$ in the 4-, 7- or 8-position of the phenanthridine or $R^c$ is other than hydrogen if Y is substituent b), at least one $R^a$ in the 3-, 4- or 7-position of the phenanthridine or $R^c$ is other than hydrogen if Y is substituent a), at least one $R^a$ in the 1-, 7- or 8-position of the phenanthridine or $R^c$ is other than hydrogen if Y is substituent d), or at least one $R^a$ in the 3-, 4- or 10-position of the phenanthridine or $R^c$ is other than hydrogen if Y is substituent c). In the most preferred compounds, in total, up to two $R^a$ substituents in two of those positions are other than hydrogen.

The formulas depicting substituent Y show positively charged states for that substituent. It is understood that certain embodiments of substituent Y, which are cationic by virtue of having a protonating hydrogen atom attached to the nitrogen, may also exist or be produced under certain conditions as a neutral substituent by virtue of the absence of such a hydrogen atom. Whether such a substituent Y will be predominately cationic or neutral in a given physical state will be governed by principles of acid-base chemistry, which are well known to those skilled in the art. For example, the particular ratio of neutral form to cationic form will depend upon the basicity of the phenanthridinyl nitrogen and the acidity of the solution. When the phenanthridinyl substituent is in a protonated quaternized state, the compound exists as a zwitterion which is internally balanced as to charge. When the phenanthridinyl substituent is not in a protonated quaternized state, the compound exists as a anionic carboxylic acid salt, balance with an appropriate cation, M.

Suitable $R^a$ are described above in the text associated with Formula I. Among preferred $R^a$ are $C_{1-4}$ alkyl mono-substituted with hydroxy, such as, hydroxymethyl; formyl; alkoxycarbonyl, such as, —COOMe; carbamoyl, such as, —CONH$_2$; hydroxoximinomethyl, such as, —CH═NOH or cyano.

For example, when Y is substituent b), in regard to this preferred substitution, the hydroxymethyl groups may be obtained in the 4, 7, and 8-positions of the phenanthridine as follows. Thus referring to Flow Sheet B, methyl, as a precursor substituent, is substituted on starting materials B-3 and/or B-5 in the appropriate positions by well know means. Subsequently the methyl substituent of methyl-substituted B-3, B-5, B-6 or B-8 may be oxidized e.g. to carboxy with ruthenium tetroxide or to bromomethyl with N-bromosuccinimide. The resultant carboxy or bromomethyl substituted starting material may be further elaborated. In the case of the bromomethyl substituent, conversion to a hydroxymethyl substituted precursor may be accomplished by a three-step sequence. Reaction of the bromomethyl compound with potassium acetate in DMF at 60°–100° C. gives the corresponding acetoxymethyl compound. Removal of the acetate group, e.g. by hydrolysis with methanolic sodium hydroxide or by reduction with diisobutylaluminium hydride in THF, gives the hydroxymethyl substituted compound which may then be incorporated in the synthesis of a correspondingly substituted B11. When necessary the hydroxymethyl moiety may be protected by silylation with t-butyldimethylsilyl chloride, triethylamine and 4-dimethylaminopyridine in dichloromethane or t-butyldimethylsilyl chloride and imidazole in DMF. Further elaboration of B-3, B-5, B-6, B-8 or B-10 provides other moieties as described hereinbelow.

The preferred formyl substitution on the phenanthridine may be obtained from the hydroxymethyl substituted starting material just described by a Swern oxidation. For example, the hydroxymethyl is oxidized in methylene chloride at from −70° C. to room temperature employing oxalyl chloride-dimethyl sulfoxide followed by triethylamine as the active agent. Obviously, the position of the resultant formyl substitution will depend upon the position of the hydroxymethyl substitution on compound B-3, B-5 B-6, B-8 or B-10.

The preferred —CH═NOH substitution on the phenanthridine may be conveniently obtained from the formyl substitution just described. This is accomplished simply by exposing the formyl substituted compound to hydroxylamine in an appropriate solvent at room temperature.

The preferred cyano substitution on the phenanthridine may be obtained from the —CH═NOH substitution just described. The —CH═NOH substituted compound is dehydrated with triflic anhydride and triethylamine in a solvent at −70° C.

The preferred alkoxycarbonyl substitution on the phenanthridine may be obtained from the hydroxymethyl substituted starting material. For example, the substituted compound B-7 or B-8 is oxidized with Jones reagent to convert the hydroxymethyl substituent to a carboxylic acid group. This carboxylic acid group may then be esterified by procedures well known in the art, such as treatment with diazomethane and the like.

The preferred carbamoyl substitution on the phenanthridine, may be obtained by oxidizing the hydroxymethyl group with Jones reagent to the corresponding carboxylic acid group as described above. This carboxylic acid substituent is converted to the carboxamide group, —CONH$_2$, by sequentially contacting with 1-ethyl-3-(3-dimethylaminopropyl)carbodiimide hydrochloride, 1-hydroxybenzotriazole, and ammonia in an organic solvent at room temperature. Substituted amides may of course be obtained by replacing ammonia with the corresponding substituted amine.

In the preparation methods described above, the carboxyl group at the 3-position and the hydroxyl group at the 8-position of the carbapenem remain blocked by protecting groups until the penultimate product is prepared. Deblocking may be carried out in a conventional manner. For compounds prepared via Flow Sheet F, if the hydroxyethyl moiety has been protected deprotection is conducted sequentially. Thus, compound F-3 where $R^p$ is a trialkylsilyl is exposed initially to aqueous acidic conditions, acetic acid or dilute HCl or the like, in an organic solvent such as tetrahydrofuran at 0° C. to ambient temperature for from a few minutes to several hours. The desilylated carbapenem may be isolated by conventional techniques, but is more conveniently taken into the final deprotection process. Thus, addition of a base such as NaHCO$_3$ or KHCO$_3$, and optionally a buffer such as MOPS buffer, phosphate buffer and the like, and a suitable catalyst, such as 5%–10% Pd/C, 5%–10% Rh/Al$_2$O$_3$, 5%–10% Rh/C and the like, followed by hydrogenation provides for the removal of the p-nitrobenzyl protecting group and the formation of the final compound of Formula I.

With reference to the above definitions, "alkyl" means a straight or branched chain aliphatic hydrocarbon radical.

The term "heteroatom" means N, S, or O, selected on an independent basis.

The term "heteroaryl" has been defined herein, in relation to the $R^x$ group, to have a specific and limited meaning, being only monocyclic. It is required that the monocyclic heteroaryl have at least one nitrogen atom, and optionally at most only one additional oxygen or sulfur heteroatom may be present. Heteroaryls of this type are pyrrole and pyridine (1N); and oxazole, thiazole or oxazine (1N+1 O or 1 S). While additional nitrogen atoms may be present together with the first nitrogen and oxygen or sulfur, giving, e.g., a thiadiazole (2N's+1S), the preferred heteroaryls are those where only nitrogen heteroatoms are present when there is more than one. Typical of these are pyrazole, imidazole, pyrimidine and pyrazine (2 N's) and triazine (3 N's).

The heteroaryl group of $R^x$ is always optionally mono-substituted by $R^q$, defined above, and substitution can be on one of the carbon atoms or one of the heteroatoms, although in the latter case certain substitutent choices may not be appropriate.

The ring system formed when $R^g$ is combined with $R^d$ to form a diradical which forms a ring is easily understood by those of ordinary skill in the art and may be illustrated by the following structures:

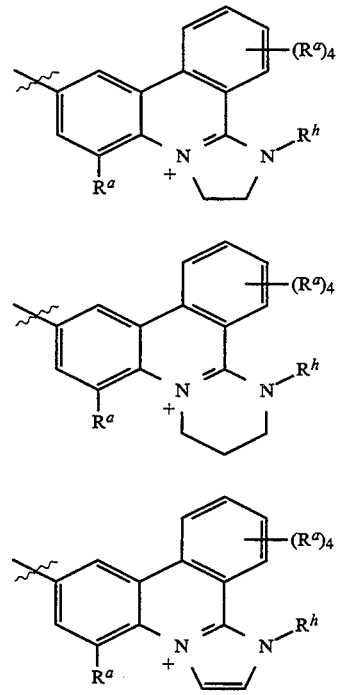

Preparation of the such a ring system has been previously described in the literature (R. F. Cookson and R. E. Rodway, *J. Chem. Soc. Perkin I*, 1850 (1975)).

The compounds of the instant invention are characterized by substitution on the ring nitrogen of the phenanthridinyl moiety which creates a positive charge at that nitrogen. Another term for such a charge is that the nitrogen is quaternized. This charge is offset by the carboxylate moiety in the 3-position of the carbapenem, thus giving the molecule an overall neutral characteristic. Usually such a nitrogen substitution is characterized by a covalent bond which is unaffected by the pH of the solution in which the compound is dissolved. However, when the ring substituent $R^a$ or $R^c$ is an amine group in conjugation with the ring nitrogen, said ring nitrogen may be sufficiently basic in character such that at physiological pH said ring nitrogen may be protonated and thus positively charged. This charge is offset by the carboxylate moiety in the 3-position of the carbapenem. The structure below illustrates this situation where the $R^c$ substitution is an amine and the ring nitrogen is substituted by a hydrogen atom. It is understood that this invention encompasses such a pH dependent charged substitution on the ring nitrogen.

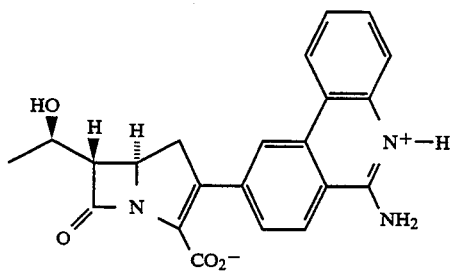

Also understood by the instant invention is a compound wherein the phenanthridine moiety is substituted by an amine group but the ring nitrogen is not sufficiently basic in character to be protonated at physiological pH. This latter embodiment of the instant invention has a phenanthridine moiety which has no substituent on the ring nitrogen and the negative charge of the carboxylate moiety in the 3-position of the carbapenem is offset by an alkali metal or other pharmaceutically acceptable cation.

Listed in Tables I, II, III and IV are specific compounds of the instant invention. It is understood that when $R^d$ is $O^-$ or is absent, a cation M must also be associated with the compound described so as to render the compound neutral overall. These compounds are meant to be illustrative and are not limiting.

TABLE I

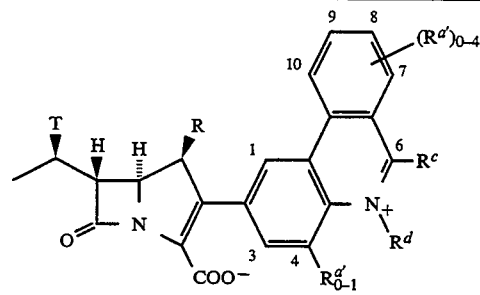

| R | $R^{a'}$ | $R^{a'}$ Position | T | $R^c$ | $R^d$ |
|---|---|---|---|---|---|
| H | —CN | 4 | OH | H | $CH_3$ |
| H | —$CONH_2$ | 4 | OH | H | $CH_3$ |
| H | —$CONMe_2$ | 4 | OH | H | $CH_3$ |
| H | —CHO | 4 | OH | H | $CH_3$ |
| H | —$SCH_3$ | 4 | OH | H | $CH_3$ |
| H | —$SOCH_3$ | 4 | OH | H | $CH_3$ |
| H | —$SO_2CH_3$ | 4 | OH | H | $CH_3$ |
| H | —F | 4 | OH | H | $CH_3$ |
| H | —$SO_2NH_2$ | 4 | OH | H | $CH_3$ |
| H | —$CH_2OH$ | 8 | OH | H | $CH_3$ |
| H | —CN | 8 | OH | H | $CH_3$ |
| H | —$CONH_2$ | 8 | OH | H | $CH_3$ |
| H | —CHO | 8 | OH | H | $CH_3$ |
| H | —$CH_2OH$ | 7 | OH | H | $CH_3$ |
| H | —CN | 7 | OH | H | $CH_3$ |
| H | —$CONH_2$ | 7 | OH | H | $CH_3$ |
| H | —CHO | 7 | OH | H | $CH_3$ |
| H | —CN | 4 | F | H | $CH_3$ |
| H | —CHO | 4 | F | H | $CH_3$ |
| H | —$CONH_2$ | 4 | F | H | $CH_3$ |
| $CH_3$ | —CN | 4 | OH | H | $CH_3$ |
| $CH_3$ | —$CONH_2$ | 4 | OH | H | $CH_3$ |
| $CH_3$ | —CHO | 4 | OH | H | $CH_3$ |
| $CH_3$ | —CN | 4 | F | H | $CH_3$ |
| H | —CN | 4 | OH | H | Et |
| H | —$CONH_2$ | 4 | OH | H | Pr |
| H | —$CONH_2$ | 4 | OH | H | Bu |
| H | —$CF_3$ | 8 | OH | H | $CH_3$ |
| H | —$OCH_3$ | 9 | OH | H | $CH_3$ |

TABLE I-continued

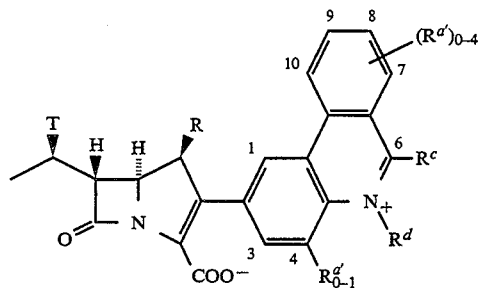

| R | $R^{a'}$ | $R^{a'}$ Position | T | $R^c$ | $R^d$ |
|---|---|---|---|---|---|
| H | —OCH$_2$CO$_2$CH$_3$ | 10 | OH | H | CH$_3$ |
| H | —Cl | 4,7,8 | OH | H | CH$_3$ |
| H | —OH | 9 | OH | H | CH$_3$ |
| H | —OCOCH$_3$ | 8 | OH | H | CH$_3$ |
| H | —OCONH$_2$ | 8 | OH | H | CH$_3$ |
| H | —SCH$_2$CH$_2$OH | 8 | OH | H | CH$_3$ |
| H | —SOCH$_2$CH$_2$OH | 9 | OH | H | CH$_3$ |
| H | —SCH$_2$CONH$_2$ | 4 | OH | H | CH$_3$ |
| H | —SO$_2$NMe$_2$ | 4,8 | OH | H | CH$_3$ |
| H | —NHCHO | 8 | OH | H | CH$_3$ |
| H | — | | OH | —NHCH$_2$CONH$_2$ | CH$_3$ |
| H | — | | OH | —N(CH$_3$)$_2$ | CH$_3$ |
| H | — | | F | —N(CH$_3$)$_2$ | CH$_3$ |
| CH$_3$ | — | | OH | —N(CH$_3$)$_2$ | CH$_3$ |
| H | —CH$_2$OH | 8 | OH | H | O$^-$ |
| H | —CH$_2$OH | 8 | OH | H | NH$_2$ |
| H | —CH$_2$OH | 8 | OH | H | CH$_2$CH$_2$OH |
| H | —CH$_2$OH | 8 | OH | H | CH$_2$CH$_2$CH$_2$CN |
| H | —NHCOCH$_3$ | 9 | OH | H | CH$_3$ |
| H | —NHCOCH$_3$ | 10 | OH | H | CH$_3$ |
| H | —NHSO$_2$CH$_3$ | 4 | OH | H | CH$_3$ |
| H | —COMe | 4 | OH | H | CH$_3$ |
| H | —COCH$_2$OH | 7 | OH | H | CH$_3$ |
| H | —CH=NOH | 8 | OH | H | CH$_3$ |
| H | —CH=NOMe | 7 | OH | H | CH$_3$ |
| H | —CH=NOCH$_2$CO$_2$Me | 8 | OH | H | CH$_3$ |
| H | —CH=NOCM$_{e2}$CO$_2$Me | 8 | OH | H | CH$_3$ |
| H | —CH=NOCMe$_2$CONH$_2$ | 9 | OH | H | CH$_3$ |
| H | —CO$_2$CH$_2$CH$_2$OH | 10 | OH | H | CH$_3$ |
| H | —CONHCH$_3$ | 4 | OH | H | CH$_3$ |
| H | —CONHCH$_2$CN | 4 | OH | H | CH$_3$ |
| H | —CONHCH$_2$CN | 4 | F | H | CH$_3$ |
| CH$_3$ | —CONHCH$_2$CN | 4 | OH | H | CH$_3$ |
| H | —CONHCH$_2$CONH$_2$ | 8 | OH | H | CH$_3$ |
| H | —CONHCH$_2$CO$_2$CH$_3$ | 9 | OH | H | CH$_3$ |
| H | —CONHOH | 4 | OH | H | CH$_3$ |
| H | —CONHOCH$_3$ | 10 | OH | H | CH$_3$ |
| H | —CO$_2$CH$_3$ | 4 | OH | H | CH$_3$ |
| H | -tetrazolyl | 8 | OH | H | CH$_3$ |
| H | —SCF$_3$ | 4 | OH | H | CH$_3$ |
| H | —PO$_2$NH$_2$ | 4 | OH | H | CH$_3$ |
| H | —CONHSO$_2$Ph | 4 | OH | H | CH$_3$ |
| H | —CONHSO$_2$NH$_2$ | 4 | OH | H | CH$_3$ |
| H | —SO$_2$CF$_3$ | 8 | OH | H | CH$_3$ |
| H | —SO$_2$NHCN | 4 | OH | H | CH$_3$ |
| H | —SO$_2$NHCONH$_2$ | 4 | OH | H | CH$_3$ |
| H | —CH=CHCN | 4 | OH | H | CH$_3$ |
| H | —CH=CHCONH$_2$ | 4 | OH | H | CH$_3$ |
| H | —C≡C—CN | 4 | OH | H | CH$_3$ |
| H | —CH$_2$N$_3$ | 7 | OH | H | CH$_3$ |
| H | —CH$_2$CO$_2$Me | 10 | OH | H | CH$_3$ |
| H | —SO$_2$CH$_2$CH$_2$OH | 4 | OH | H | CH$_3$ |
| H | —CH$_2$I | 8 | OH | H | CH$_3$ |
| H | —I | 4 | OH | H | CH$_3$ |
| H | —Br | 4 | OH | H | CH$_3$ |
| H | — | | OH | H | CH$_2$CH$_2$CH$_3$ |
| H | — | | OH | OCH$_3$ | CH$_3$ |
| H | — | | OH | NHCH$_2$CH$_2$OH | CH$_3$ |
| H | — | | OH | N-pyrrolidinyl | CH$_3$ |
| H | — | | OH | NH$_2$ | H |

TABLE II

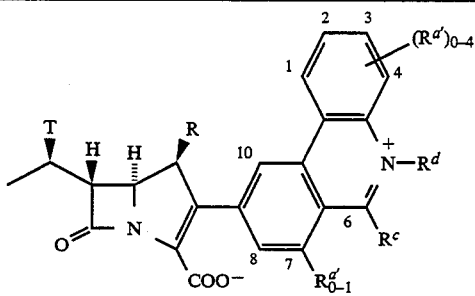

| R | $R^{a'}$ | $R^{a'}$ Position | T | $R^c$ | $R^d$ |
|---|---|---|---|---|---|
| H | —CN | 7 | OH | H | $CH_3$ |
| H | —$CONH_2$ | 7 | OH | H | $CH_3$ |
| H | —$CONMe_2$ | 7 | OH | H | $CH_3$ |
| H | —CHO | 7 | OH | H | $CH_3$ |
| H | —$SCH_3$ | 7 | OH | H | $CH_3$ |
| H | —$SOCH_3$ | 7 | OH | H | $CH_3$ |
| H | —$SO_2CH_3$ | 7 | OH | H | $CH_3$ |
| H | —F | 7 | OH | H | $CH_3$ |
| H | —$SO_2NH_2$ | 7 | OH | H | $CH_3$ |
| H | —$CH_2OH$ | 3 | OH | H | $CH_3$ |
| H | —CN | 3 | OH | H | $CH_3$ |
| H | —$CONH_2$ | 3 | OH | H | $CH_3$ |
| H | —CHO | 3 | OH | H | $CH_3$ |
| H | —$CH_2OH$ | 4 | OH | H | $CH_3$ |
| H | —CN | 4 | OH | H | $CH_3$ |
| H | —$CONH_2$ | 4 | OH | H | $CH_3$ |
| H | —CHO | 4 | OH | H | $CH_3$ |
| H | —CN | 7 | F | H | $CH_3$ |
| H | —CHO | 7 | F | H | $CH_3$ |
| H | —$CONH_2$ | 7 | F | H | $CH_3$ |
| $CH_3$ | —CN | 7 | OH | H | $CH_3$ |
| $CH_3$ | —$CONH_2$ | 7 | OH | H | $CH_3$ |
| $CH_3$ | —CHO | 7 | OH | H | $CH_3$ |
| $CH_3$ | —CN | 7 | F | H | $CH_3$ |
| H | —CN | 7 | OH | H | Et |
| H | —$CONH_2$ | 7 | OH | H | Pr |
| H | —$CONH_2$ | 7 | OH | H | Bu |
| H | —$CF_3$ | 3 | OH | H | $CH_3$ |
| H | —$OCH_3$ | 2 | OH | H | $CH_3$ |
| H | —$OCH_2CO_2CH_3$ | 1 | OH | H | $CH_3$ |
| H | —Cl | 3,4,7 | OH | H | $CH_3$ |
| H | —OH | 2 | OH | H | $CH_3$ |
| H | —$OCOCH_3$ | 3 | OH | H | $CH_3$ |
| H | —$OCONH_2$ | 3 | OH | H | $CH_3$ |
| H | —$SCH_2CH_2OH$ | 3 | OH | H | $CH_3$ |
| H | —$SOCH_2CH_2OH$ | 2 | OH | H | $CH_3$ |
| H | —$SCH_2CONH_2$ | 7 | OH | H | $CH_3$ |
| H | —$SO_2NMe_2$ | 7,3 | OH | H | $CH_3$ |
| H | —NHCHO | 3 | OH | H | $CH_3$ |
| H | — | | OH | —$NHCH_2CONH_2$ | $CH_3$ |
| H | — | | OH | —$N(CH_3)_2$ | $CH_3$ |
| H | — | | F | —$N(CH_3)_2$ | $CH_3$ |
| $CH_3$ | — | | OH | —$N(CH_3)_2$ | $CH_3$ |
| H | —$CH_2OH$ | 3 | OH | H | $O^-$ |
| H | —$CH_2OH$ | 3 | OH | H | $NH_2$ |
| H | —$CH_2OH$ | 3 | OH | H | $CH_2CH_2OH$ |
| H | —$CH_2OH$ | 3 | OH | H | $CH_2CH_2CH_2CN$ |
| H | —$NHCOCH_3$ | 2 | OH | H | $CH_3$ |
| H | —$NHCOCH_3$ | 1 | OH | H | $CH_3$ |
| H | —$NHSO_2CH_3$ | 7 | OH | H | $CH_3$ |
| H | —COMe | 7 | OH | H | $CH_3$ |
| H | —$COCH_2OH$ | 4 | OH | H | $CH_3$ |
| H | —CH=NOH | 3 | OH | H | $CH_3$ |
| H | —CH=NOMe | 4 | OH | H | $CH_3$ |
| H | —CH=$NOCH_2CO_2Me$ | 3 | OH | H | $CH_3$ |
| H | —CH=$NOCMe_2CO_2Me$ | 3 | OH | H | $CH_3$ |
| H | —CH=$NOCMe_2CONH_2$ | 2 | OH | H | $CH_3$ |
| H | —$CO_2CH_2CH_2OH$ | 1 | OH | H | $CH_3$ |
| H | —$CONHCH_3$ | 7 | OH | H | $CH_3$ |
| H | —$CONHCH_2CN$ | 7 | OH | H | $CH_3$ |
| H | —$CONHCH_2CN$ | 7 | F | H | $CH_3$ |
| $CH_3$ | —$CONHCH_2CN$ | 7 | OH | H | $CH_3$ |
| H | —$CONHCH_2CONH_2$ | 3 | OH | H | $CH_3$ |
| H | —$CONHCH_2CO_2CH_3$ | 2 | OH | H | $CH_3$ |
| H | —CONHOH | 7 | OH | H | $CH_3$ |
| H | —$CONHOCH_3$ | 1 | OH | H | $CH_3$ |

TABLE II-continued

| R | $R^{a'}$ | $R^{a'}$ Position | T | $R^c$ | $R^d$ |
|---|---|---|---|---|---|
| H | —CO$_2$CH$_3$ | 7 | OH | H | CH$_3$ |
| H | -tetrazolyl | 3 | OH | H | CH$_3$ |
| H | —SCF$_3$ | 7 | OH | H | CH$_3$ |
| H | —PO$_2$NH$_2$ | 7 | OH | H | CH$_3$ |
| H | —CONHSO$_2$Ph | 7 | OH | H | CH$_3$ |
| H | —CONHSO$_2$NH$_2$ | 7 | OH | H | CH$_3$ |
| H | —SO$_2$CF$_3$ | 3 | OH | H | CH$_3$ |
| H | —SO$_2$NHCN | 7 | OH | H | CH$_3$ |
| H | —SO$_2$NHCONH$_2$ | 7 | OH | H | CH$_3$ |
| H | —CH=CHCN | 7 | OH | H | CH$_3$ |
| H | —CH=CHCONH$_2$ | 7 | OH | H | CH$_3$ |
| H | —C≡C—CN | 7 | OH | H | CH$_3$ |
| H | —CH$_2$N$_3$ | 4 | OH | H | CH$_3$ |
| H | —CH$_2$CO$_2$Me | 1 | OH | H | CH$_3$ |
| H | —SO$_2$CH$_2$CH$_2$OH | 7 | OH | H | CH$_3$ |
| H | —CH$_2$I | 3 | OH | H | CH$_3$ |
| H | —I | 7 | OH | H | CH$_3$ |
| H | —Br | 7 | OH | H | CH$_3$ |
| H | — | | OH | H | CH$_2$CH$_2$CH$_3$ |
| H | — | | OH | OCH$_3$ | CH$_3$ |
| H | — | | OH | NHCH$_2$CH$_2$OH | CH$_3$ |
| H | — | | OH | N-pyrrolidinyl | CH$_3$ |
| H | — | | OH | NH$_2$ | H |

TABLE III

| R | $R^{a'}$ | $R^{a'}$ Position | T | $R^c$ | $R^d$ |
|---|---|---|---|---|---|
| H | —CN | 1 | OH | H | CH$_3$ |
| H | —CONH$_2$ | 1 | OH | H | CH$_3$ |
| H | —CONMe$_2$ | 1 | OH | H | CH$_3$ |
| H | —CHO | 1 | OH | H | CH$_3$ |
| H | —SCH$_3$ | 1 | OH | H | CH$_3$ |
| H | —SOCH$_3$ | 1 | OH | H | CH$_3$ |
| H | —SO$_2$CH$_3$ | 1 | OH | H | CH$_3$ |
| H | —F | 1 | OH | H | CH$_3$ |
| H | —SO$_2$NH$_2$ | 1 | OH | H | CH$_3$ |
| H | —CH$_2$OH | 8 | OH | H | CH$_3$ |
| H | —CN | 8 | OH | H | CH$_3$ |
| H | —CONH$_2$ | 8 | OH | H | CH$_3$ |
| H | —CHO | 8 | OH | H | CH$_3$ |
| H | —CH$_2$OH | 7 | OH | H | CH$_3$ |
| H | —CN | 7 | OH | H | CH$_3$ |
| H | —CONH$_2$ | 7 | OH | H | CH$_3$ |
| H | —CHO | 7 | OH | H | CH$_3$ |
| H | —CN | 1 | F | H | CH$_3$ |
| H | —CHO | 1 | F | H | CH$_3$ |
| H | —CONH$_2$ | 1 | F | H | CH$_3$ |
| CH$_3$ | —CN | 1 | OH | H | CH$_3$ |
| CH$_3$ | —CONH$_2$ | 1 | OH | H | CH$_3$ |
| CH$_3$ | —CHO | 1 | OH | H | CH$_3$ |
| CH$_3$ | —CN | 1 | F | H | CH$_3$ |
| H | —CN | 1 | OH | H | Et |

TABLE III-continued

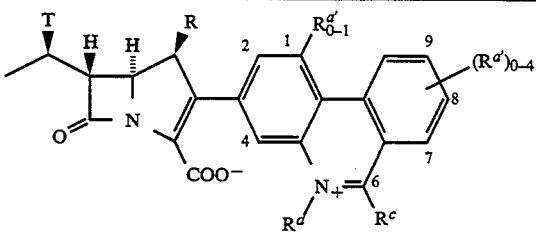

| R | $R^{a'}$ | $R^{a'}$ Position | T | $R^c$ | $R^d$ |
|---|---|---|---|---|---|
| H | —CONH$_2$ | 1 | OH | H | Pr |
| H | —CONH$_2$ | 1 | OH | H | Bu |
| H | —CF$_3$ | 8 | OH | H | CH$_3$ |
| H | —OCH$_3$ | 9 | OH | H | CH$_3$ |
| H | —OCH$_2$CO$_2$CH$_3$ | 10 | OH | H | CH$_3$ |
| H | —Cl | 1,7,8 | OH | H | CH$_3$ |
| H | —OH | 9 | OH | H | CH$_3$ |
| H | —OCOCH$_3$ | 8 | OH | H | CH$_3$ |
| H | —OCONH$_2$ | 8 | OH | H | CH$_3$ |
| H | —SCH$_2$CH$_2$OH | 8 | OH | H | CH$_3$ |
| H | —SOCH$_2$CH$_2$OH | 9 | OH | H | CH$_3$ |
| H | —SCH$_2$CONH$_2$ | 1 | OH | H | CH$_3$ |
| H | —SO$_2$NMe$_2$ | 1,8 | OH | H | CH$_3$ |
| H | —NHCHO | 8 | OH | H | CH$_3$ |
| H | — | | OH | —NHCH$_2$CONH$_2$ | CH$_3$ |
| H | — | | OH | —N(CH$_3$)$_2$ | CH$_3$ |
| H | — | | F | —N(CH$_3$)$_2$ | CH$_3$ |
| CH$_3$ | — | | OH | —N(CH$_3$)$_2$ | CH$_3$ |
| H | —CH$_2$OH | 8 | OH | H | O$^-$ |
| H | —CH$_2$OH | 8 | OH | H | NH$_2$ |
| H | —CH$_2$OH | 8 | OH | H | CH$_2$CH$_2$OH |
| H | —CH$_2$OH | 8 | OH | H | CH$_2$CH$_2$CH$_2$CN |
| H | —NHCOCH$_3$ | 9 | OH | H | CH$_3$ |
| H | —NHCOCH$_3$ | 10 | OH | H | CH$_3$ |
| H | —NHSO$_2$CH$_3$ | 1 | OH | H | CH$_3$ |
| H | —COMe | 1 | OH | H | CH$_3$ |
| H | —COCH$_2$OH | 7 | OH | H | CH$_3$ |
| H | —CH=NOH | 8 | OH | H | CH$_3$ |
| H | —CH=NOMe | 7 | OH | H | CH$_3$ |
| H | —CH=NOCH$_2$CO$_2$Me | 8 | OH | H | CH$_3$ |
| H | —CH=NOCM$_{e2}$CO$_2$Me | 8 | OH | H | CH$_3$ |
| H | —CH=NOCMe$_2$CONH$_2$ | 9 | OH | H | CH$_3$ |
| H | —CO$_2$CH$_2$CH$_2$OH | 10 | OH | H | CH$_3$ |
| H | —CONHCH$_3$ | 1 | OH | H | CH$_3$ |
| H | —CONHCH$_2$CN | 1 | OH | H | CH$_3$ |
| H | —CONHCH$_2$CN | 1 | F | H | CH$_3$ |
| CH$_3$ | —CONHCH$_2$CN | 1 | OH | H | CH$_3$ |
| H | —CONHCH$_2$CONH$_2$ | 8 | OH | H | CH$_3$ |
| H | —CONHCH$_2$CO$_2$CH$_3$ | 9 | OH | H | CH$_3$ |
| H | —CONHOH | 1 | OH | H | CH$_3$ |
| H | —CONHOCH$_3$ | 10 | OH | H | CH$_3$ |
| H | —CO$_2$CH$_3$ | 1 | OH | H | CH$_3$ |
| H | -tetrazolyl | 8 | OH | H | CH$_3$ |
| H | —SCF$_3$ | 1 | OH | H | CH$_3$ |
| H | —PO$_2$NH$_2$ | 1 | OH | H | CH$_3$ |
| H | —CONHSO$_2$Ph | 1 | OH | H | CH$_3$ |
| H | —CONHSO$_2$NH$_2$ | 1 | OH | H | CH$_3$ |
| H | —SO$_2$CF$_3$ | 8 | OH | H | CH$_3$ |
| H | —SO$_2$NHCN | 1 | OH | H | CH$_3$ |
| H | —SO$_2$NHCONH$_2$ | 1 | OH | H | CH$_3$ |
| H | —CH=CHCN | 1 | OH | H | CH$_3$ |
| H | —CH=CHCONH$_2$ | 1 | OH | H | CH$_3$ |
| H | —C≡C—CN | 1 | OH | H | CH$_3$ |
| H | —CH$_2$N$_3$ | 7 | OH | H | CH$_3$ |
| H | —CH$_2$CO$_2$Me | 10 | OH | H | CH$_3$ |
| H | —SO$_2$CH$_2$CH$_2$OH | 1 | OH | H | CH$_3$ |
| H | —CH$_2$I | 8 | OH | H | CH$_3$ |
| H | —I | 1 | OH | H | CH$_3$ |
| H | —Br | 1 | OH | H | CH$_3$ |
| H | — | | OH | H | CH$_2$CH$_2$CH$_3$ |
| H | — | | OH | OCH$_3$ | CH$_3$ |
| H | — | | OH | NHCH$_2$CH$_2$OH | CH$_3$ |
| H | — | | OH | N-pyrrol-idinyl | CH$_3$ |
| H | — | | OH | NH$_2$ | H |

TABLE IV

| R | $R^{a'}$ | $R^{a'}$ Position | T | $R^c$ | $R^d$ |
|---|---|---|---|---|---|
| H | —CN | 7 | OH | H | $CH_3$ |
| H | —$CONH_2$ | 10 | OH | H | $CH_3$ |
| H | —$CONMe_2$ | 10 | OH | H | $CH_3$ |
| H | —CHO | 10 | OH | H | $CH_3$ |
| H | —$SCH_3$ | 10 | OH | H | $CH_3$ |
| H | —$SOCH_3$ | 10 | OH | H | $CH_3$ |
| H | —$SO_2CH_3$ | 10 | OH | H | $CH_3$ |
| H | —F | 10 | OH | H | $CH_3$ |
| H | —$SO_2NH_2$ | 10 | OH | H | $CH_3$ |
| H | —$CH_2OH$ | 3 | OH | H | $CH_3$ |
| H | —CN | 3 | OH | H | $CH_3$ |
| H | —$CONH_2$ | 3 | OH | H | $CH_3$ |
| H | —CHO | 3 | OH | H | $CH_3$ |
| H | —$CH_2OH$ | 4 | OH | H | $CH_3$ |
| H | —CN | 4 | OH | H | $CH_3$ |
| H | —$CONH_2$ | 4 | OH | H | $CH_3$ |
| H | —CHO | 4 | OH | H | $CH_3$ |
| H | —CN | 10 | F | H | $CH_3$ |
| H | —CHO | 10 | F | H | $CH_3$ |
| H | —$CONH_2$ | 10 | F | H | $CH_3$ |
| $CH_3$ | —CN | 10 | OH | H | $CH_3$ |
| $CH_3$ | —$CONH_2$ | 10 | OH | H | $CH_3$ |
| $CH_3$ | —CHO | 10 | OH | H | $CH_3$ |
| $CH_3$ | —CN | 10 | F | H | $CH_3$ |
| H | —CN | 10 | OH | H | Et |
| H | —$CONH_2$ | 10 | OH | H | Pr |
| H | —$CONH_2$ | 10 | OH | H | Bu |
| H | —$CF_3$ | 3 | OH | H | $CH_3$ |
| H | —$OCH_3$ | 2 | OH | H | $CH_3$ |
| H | —$OCH_2CO_2CH_3$ | 1 | OH | H | $CH_3$ |
| H | —Cl | 3,4,10 | OH | H | $CH_3$ |
| H | —OH | 2 | OH | H | $CH_3$ |
| H | —$OCOCH_3$ | 3 | OH | H | $CH_3$ |
| H | —$OCONH_2$ | 3 | OH | H | $CH_3$ |
| H | —$SCH_2CH_2OH$ | 3 | OH | H | $CH_3$ |
| H | —$SOCH_2CH_2OH$ | 2 | OH | H | $CH_3$ |
| H | —$SCH_2CONH_2$ | 10 | OH | H | $CH_3$ |
| H | —$SO_2NMe_2$ | 10,3 | OH | H | $CH_3$ |
| H | —NHCHO | 3 | OH | H | $CH_3$ |
| H | — | | OH | —$NHCH_2CONH_2$ | $CH_3$ |
| H | — | | OH | —$N(CH_3)_2$ | $CH_3$ |
| H | — | | F | —$N(CH_3)_2$ | $CH_3$ |
| $CH_3$ | — | | OH | —$N(CH_3)_2$ | $CH_3$ |
| H | —$CH_2OH$ | 3 | OH | H | $O^-$ |
| H | —$CH_2OH$ | 3 | OH | H | $NH_2$ |
| H | —$CH_2OH$ | 3 | OH | H | $CH_2CH_2OH$ |
| H | —$CH_2OH$ | 3 | OH | H | $CH_2CH_2CH_2CN$ |
| H | —$NHCOCH_3$ | 2 | OH | H | $CH_3$ |
| H | —$NHCOCH_3$ | 1 | OH | H | $CH_3$ |
| H | —$NHSO_2CH_3$ | 10 | OH | H | $CH_3$ |
| H | —COMe | 10 | OH | H | $CH_3$ |
| H | —$COCH_2OH$ | 4 | OH | H | $CH_3$ |
| H | —CH=NOH | 3 | OH | H | $CH_3$ |
| H | —CH=NOMe | 4 | OH | H | $CH_3$ |
| H | —CH=$NOCH_2CO_2Me$ | 3 | OH | H | $CH_3$ |
| H | —CH=$NOCMe_2CO_2Me$ | 3 | OH | H | $CH_3$ |
| H | —CH=$NOCMe_2CONH_2$ | 2 | OH | H | $CH_3$ |
| H | —$CO_2CH_2CH_2OH$ | 1 | OH | H | $CH_3$ |
| H | —$CONHCH_3$ | 10 | OH | H | $CH_3$ |
| H | —$CONHCH_2CN$ | 10 | OH | H | $CH_3$ |
| H | —$CONHCH_2CN$ | 10 | F | H | $CH_3$ |
| $CH_3$ | —$CONHCH_2CN$ | 10 | OH | H | $CH_3$ |
| H | —$CONHCH_2CONH_2$ | 3 | OH | H | $CH_3$ |
| H | —$CONHCH_2CO_2CH_3$ | 2 | OH | H | $CH_3$ |
| H | —CONHOH | 10 | OH | H | $CH_3$ |
| H | —$CONHOCH_3$ | 1 | OH | H | $CH_3$ |
| H | —$CO_2CH_3$ | 10 | OH | H | $CH_3$ |
| H | -tetrazol4l | 3 | OH | H | $CH_3$ |
| H | —$SCF_3$ | 10 | OH | H | $CH_3$ |

TABLE IV-continued

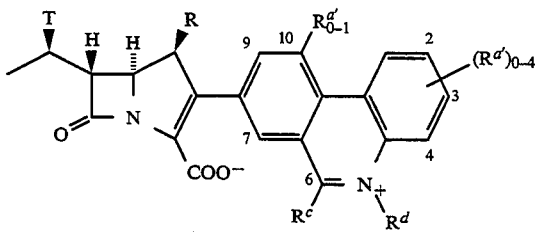

| R | $R^{a'}$ | $R^{a'}$ Position | T | $R^c$ | $R^d$ |
|---|---|---|---|---|---|
| H | $-PO_2NH_2$ | 10 | OH | H | $CH_3$ |
| H | $-CONHSO_2Ph$ | 10 | OH | H | $CH_3$ |
| H | $-CONHSO_2NH_2$ | 10 | OH | H | $CH_3$ |
| H | $-SO_2CF_3$ | 3 | OH | H | $CH_3$ |
| H | $-SO_2NHCN$ | 10 | OH | H | $CH_3$ |
| H | $-SO_2NHCONH_2$ | 10 | OH | H | $CH_3$ |
| H | $-CH=CHCN$ | 10 | OH | H | $CH_3$ |
| H | $-CH=CHCONH_2$ | 10 | OH | H | $CH_3$ |
| H | $-C\equiv C-CN$ | 10 | OH | H | $CH_3$ |
| H | $-CH_2N_3$ | 4 | OH | H | $CH_3$ |
| H | $-CH_2CO_2Me$ | 1 | OH | H | $CH_3$ |
| H | $-SO_2CH_2CH_2OH$ | 10 | OH | H | $CH_3$ |
| H | $-CH_2I$ | 3 | OH | H | $CH_3$ |
| H | $-I$ | 10 | OH | H | $CH_3$ |
| H | $-Br$ | 10 | OH | H | $CH_3$ |
| H | — | | OH | H | $CH_2CH_2CH_3$ |
| H | — | | OH | $OCH_3$ | $CH_3$ |
| H | — | | OH | $NHCH_2CH_2OH$ | $CH_3$ |
| H | — | | OH | N-pyrrolidinyl | $CH_3$ |
| H | — | | OH | $NH_2$ | H |

The carbapenem compounds of the present invention are useful per se and in their pharmaceutically acceptable salt and ester forms in the treatment of bacterial infections in animal and human subjects. The term "pharmaceutically acceptable ester or salt" refers to those salt and ester forms of the compounds of the present invention which would be apparent to the pharmaceutical chemist, i.e., those which are non-toxic and which would favorably affect the pharmacokinetic properties of said compounds, their palatability, absorption, distribution, metabolism and excretion. Other factors, more practical in nature, which are also important in the selection, are cost of the raw materials, ease of crystallization, yield, stability, hygroscopicity, and flowability of the resulting bulk drug. Conveniently, pharmaceutical compositions may be prepared from the active ingredients in combination with pharmaceutically acceptable carriers. Thus, the present invention is also concerned with pharmaceutical compositions and methods of treating bacterial infections utilizing as an active ingredient the novel carbapenem compounds of the present invention.

The pharmaceutically acceptable salts referred to above may take the form —COOM. The M may be an alkali metal cation such as sodium or potassium. Other pharmaceutically acceptable cations for M may be calcium, magnesium, zinc, ammonium, or alkylammonium cations such as tetramethylammonium, tetrabutylammonium, choline, triethylhydroammonium, meglumine, triethanolhydroammonium, etc.

The pharmaceutical acceptable esters of the novel carbapenem compounds of the present invention are such as would be readily apparent to a medicinal chemist, and include, for example, those described in detail in U.S. Pat. No. 4,309,438, Column 9, line 61 to Column 12, line 51, which is incorporated herein by reference. Included within such pharmaceutically acceptable esters are those which are hydrolyzed under physiological conditions, such as pivaloyloxymethyl, acetoxymethyl, phthalidyl, indanyl and methoxymethyl, and those described in detail in U.S. Pat. No. 4,479,947, which is incorporated herein by reference.

The novel carbapenem compounds of the present invention may take the form COOM, where M is a readily removable carboxyl protecting group. Such conventional blocking groups consist of known ester groups which are used to protectively block the carboxyl group during the synthesis procedures described above. These conventional blocking groups are readily removable, i.e., they can be removed, if desired, by procedures which will not cause cleavage or other disruption of the remaining portions of the molecule. Such procedures include chemical and enzymatic hydrolysis, treatment with chemical reducing or oxidizing agents under mild conditions, treatment with a transition metal catalyst and a nucleophile, and catalytic hydrogenation. Examples of such ester protecting groups include benzhydryl, p-nitrobenzyl, 2-naphthylmethyl, allyl, benzyl, t-butyl, trichloroethyl, silyl such as trimethylsilyl, trimethylsilylethyl, phenacyl, p-methoxybenzyl, acetonyl, o-nitrobenzyl, p-methoxyphenyl and 4-pyridylmethyl.

The compounds of the present invention are valuable antibacterial agents active against various Gram-positive and to a lesser extent Gram-negative bacteria and accordingly find utility in human and veterinary medicine. The antibacterials of the invention are not limited to utility as medicaments; they may be used in all manner of industry, for example: additives to animal feed, preservation of food, disinfectants, and in other industrial systems where control of bacterial growth is desired. For example, they may be employed in aqueous compositions in concentrations ranging from 0.1 to 100 parts of antibiotic per million parts of solution in order to destroy or inhibit the growth of harmful bacteria on medical and dental equipment and as bactericides in industrial applications, for example in waterbased paints and in the white water of paper mills to inhibit the growth of harmful bacteria.

The compounds of this invention may be used in any of a variety of pharmaceutical preparations. They may be employed in capsule, powder form, in liquid solution, or in suspension. They may be administered by a variety of means; those of principal interest include: topically or parenterally by injection (intravenously or intramuscularly).

Compositions for injection, a preferred route of delivery, may be prepared in unit dosage form in ampules, or in multidose containers. The compositions may take such forms as suspensions, solutions, or emulsions in oily or aqueous vehicles, and may contain formulatory agents. Alternatively, the active ingredient may be in powder form for reconstitution, at the time of delivery, with a suitable vehicle, such as sterile water. Topical applications may be formulated in hydrophobic or hydrophilic bases as ointments, creams, lotions, paints, or powders.

The dosage to be administered depends to a large extent upon the condition and size of the subject being treated as well as the route and frequency of administration, the parenteral route by injection being preferred for generalized infections. Such matters, however, are left to the routine discretion of the therapist according to principles of treatment well known in the antibacterial art. Another factor influencing the precise dosage regimen, apart from the nature of the infection and peculiar identity of the individual being treated, is the molecular weight of the chosen species of this invention.

The compositions for human delivery per unit dosage, whether liquid or solid, may contain from 0.1% to 99% of active material, the preferred range being from about 10-60%. The composition will generally contain from about 15 mg to about 1500 mg of the active ingredient; however, in general, it is preferable to employ a dosage amount in the range of from about 250 mg to 1000 mg. In parenteral administration, the unit dosage is usually the pure compound I in sterile water solution or in the form of a soluble powder intended for solution.

The preferred method of administration of the Formula I antibacterial compounds is parenteral by i.v. infusion, i.v. bolus, or i.m. injection.

For adults, 5-50 mg of Formula I antibacterial compounds per kg of body weight given 2, 3, or w times per day is preferred. Preferred dosage is 250 mg to 1000 mg of the Formula I antibacterial given two (b.i.d.) three (t.i.d.) or four (q.i.d.) times per day. More specifically, for mild infections a dose of 250 mg t.i.d. or q.i.d. is recommended. For moderate infections against highly susceptible gram positive organisms a dose of 500 mg t.i.d. or q.i.d. is recommended. For severe, life-threatening infections against organisms at the upper limits of sensitivity to the antibiotic, a dose of 1000 mg t.i.d. or q.i.d. is recommended.

For children, a dose of 5-25 mg/kg of body weight given 2, 3, or 4 times per day is preferred; a dose of 10 mg/kg t.i.d. or q.i.d. is usually recommended.

Antibacterial compounds of Formula I are of the broad class known as carbapenems or 1-carbadethiapenems. Naturally occuring carbapenems are susceptible to attack by a renal enzyme known as dehydropeptidase (DHP). This attack or degradation may reduce the efficacy of the carbapenem antibacterial agent. The compounds of the present invention, on the other hand, are significantly less subject to such attack, and therefore may not require the use of a DHP inhibitor. However, such use is optional and contemplated to be part of the present invention. Inhibitors of DHP and their use with carbapenem antibacterial agents are disclosed in the prior art [see European Patent Applications No. 79102616.4 filed Jul. 24, 1979 (Patent No. 0 007 614); and No. 82107174.3, filed Aug. 9, 1982 (Publication No. 0 072 014)].

The compounds of the present invention may, where DHP inhibition is desired or necessary, be combined or used with the appropriate DHP inhibitor as described in the aforesaid patents and published application. Thus, to the extent that the cited European patent applications 1.) define the procedure for determining DHP susceptibility of the present carbapenems and 2.) disclose suitable inhibitors, combination compositions and methods of treatment, they are incorporated herein by reference. A preferred weight ratio of Formula I compound: DHP inhibitor in the combination compositions is about 1:1. A preferred DHP inhibitor is 7-(L-2-amino-2-carboxyethylthio)-2-(2,2-dimethylcyclopropanecarboxamide)-2-heptenoic acid or a useful salt thereof.

The invention is further defined by reference to the following examples, which are illustrative and not limiting. All temperatures are in degrees Celsius.

EXAMPLE 1

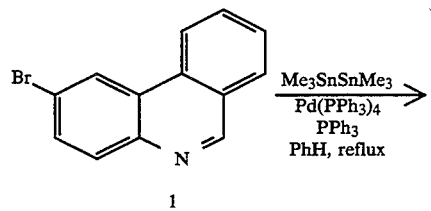

1

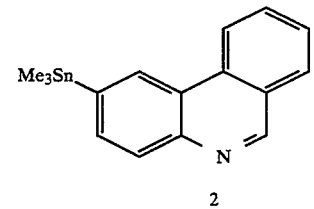

2

Dry nitrogen gas was bubbled through a mixture of 1 (300 mg; 1.16 mmol), hexamethylditin (418 mg; 1.28 mmol; 1.1 equiv.), Pd(PPh3)4 (67 mg; 0.058 mmol; 5 mol %) and triphenylphosphine (9 mg; 0.035 mmol; 3 mol %) in toluene (6 mL) for 15 minutes. The reaction mixture was then heated to reflux for 1 hr. 45 min. before being poured into Et$_2$O. The organic layers were washed with H$_2$O (1×), saturated NaHCO$_3$ (3×), H$_2$O (1×) and brine (1×). The reaction mixture was dried over MgSO$_4$, filtered and the solvent was removed in vacuo. Purification via SiO$_2$ flash column chromatography (20% EtOAc/hexanes) provided the stannane 2.

$^1$H NMR (200 MHz, CDCl$_3$) δ0.42 (s, 9H), 7.68-7.75 (m 1H), 7.85-7.92 (m, 2H), 8.06 (d, J=7.8 Hz, 1H), 8.17 (d, J=7.9 Hz, 1H), 8.67-8.74 (m, 2H), 9.28 (s, 1H).

EXAMPLE 2

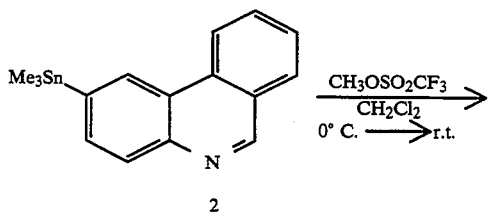

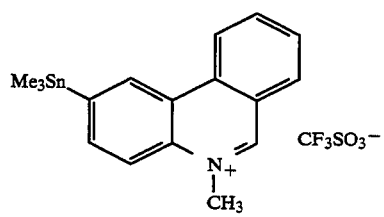

To stannane 2 (96.7 mg; 0.283 mmol), prepared as described in Example 1, in anhydrous $CH_2Cl_2$ (1.4 mL) under $N_2$ at 0° C. was added $CH_3OSO_2CF_3$(35.2 μL; 0.311 mmol; 1.1 eq). The reaction vessel was then allowed to reach ambient temperature and stirred for one hour. A white precipitate formed. Some $CHCl_3$ was then added to dissolve the precipitate, prior to removal of the solvents in vacuo to provide Stannane 3.

$^1$HNMR (300 MHz, $CDCl_3$) δ:0.48 (s, 9H), 4.81 (s, 3H), 8.00 (t, J=7.5 Hz, 1H), 8.17 (s, 2H), 8.28 (t, J=7.2 Hz, 1H), 8.80 (m, 2H), 8.93 (s, 1H), 10.54 (s, 1H).

EXAMPLE 3

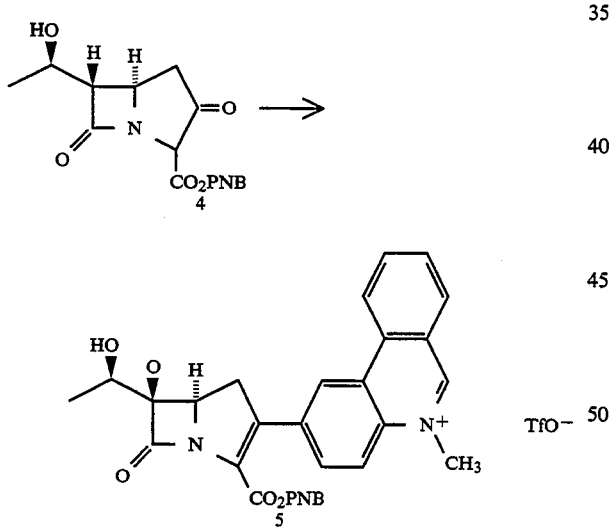

To a stirred solution of the bicyclic β-keto ester 4 (412.9 mg, 1.18 mmol) in dry THF (4.9 mL) at −78° C. under $N_2$ was added diisopropylamine (180 μL, 1.3 mmol, 1.1 eq). The resultant yellow mixture was stirred for 10 minutes before trifluoromethanesulfonic anhydride (220 μL, 1.3 mmol, 1.1 eq) was added. After 15 minutes the mixture was treated sequentially with anhydrous N-methyl-2-pyrrolidinone (4.9 mL), the $Pd_2(dba)_3$•$CHCl_3$ catalyst (24.5 mg, 2.4×10$^{-2}$mmol, 2.0 mol%), the aryl stannane 3 (500 mg, 0.988 mmol) and diisopropylammonium chloride (136 mg; 0.988 mmol). The low temperature bath was then removed and the reaction vessel was placed in a warm water bath to quickly reach ambient temperature. The resulting solution was stirred for 45 minutes at ambient temperature.

The reaction mixture was poured into EtOAc and washed repetitively with $H_2O$. The $H_2O$ layer was then back extracted with $CH_2Cl_2$. The organic layers were combined, dried over $Na_2SO_4$, filtered and the solvent was removed in vacuo. Precipitation from $CH_2Cl_2/Et_2O$ provided carbapenem 5.

$^1$H NMR (400 MHz, $D_6$-Acetone) δ:1.31 (d, J=6.3 Hz, 3H), 3.47–3.54 (m, 2H), 3.85 (½ ABX, $J_{AB}$=18.4 Hz, $J_{AX}$=8.5 Hz, 1H), 4.18–4.25 (m, 1H), 4.48–4.52 (m, 1H), 4.95 (s, 3H), 5.32 (AB$_q$, $J_{AB}$=13.7 Hz, $\Delta\nu_{AB}$=67.2 Hz, 2H), 7.54 (d, J=8.8 Hz, 2H), 7.98 (d, J=8.8 Hz, 2H), 8.15 (t, J=7.1 Hz, 1H), 8.26 (dd, J=9.0, 1.9 Hz, 1H), 8.41 (t, J=7.1 Hz, 1H), 8.62–8.66 (m, 2H), 9.08 (d, J=8.4 Hz, 1H), 9.21 (d, J=1.83 Hz, 1H); IR ($CHCl_3$)1765, 1720, 1625, 1600, 1515 cm$^{-1}$.

EXAMPLE 4

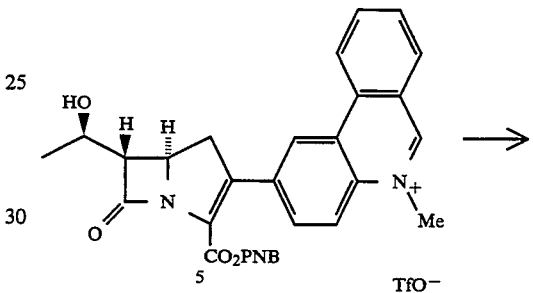

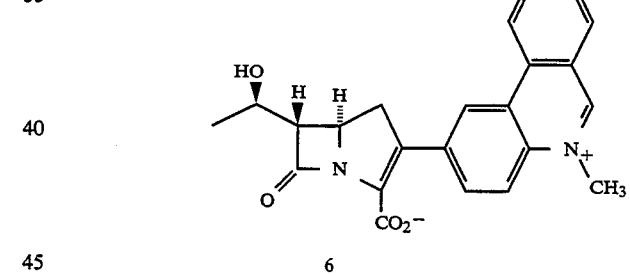

(5R,6S)-2-(5-Methyl-2-phenanthiridinyl)-6-(1R-hydroxyethyl)carbapen-2-em-3-carboxylate To a stirred solution of 5 (50 mg, 0.0072 mmol) and sodium bicarbonate solution (75.8 μL 0.0072 mmol, 1.0 eq) in 2:1 acetone/$H_2O$ was added 5% $Rh/Al_2O_3$ catalyst (5.0 mg, 10% wt), and the reaction mixture was hydrogenated under an $H_2$ balloon at ambient temperature for 40 minutes. The mixture was then filtered through a pad of celite and the acetone solvent from the filtrate was removed in vacuo. The remaining water was then frozen and lyholized at 0° C. Crude 6 was redissolved in a minimal amount of $H_2O/CH_3CN$ and purified using Analtech reverse phase prep-plates (1.6:1 $H_2O/CH_3CN$) to provide carbapenem 6.

$^1$H NMR (400 MHz, 2:1 $D_2O/CD_3CN$) δ1.68 (d, J=6.2 Hz, 3H), 3.68 (½ ABX, $J_{AB}$=15.6 Hz, $J_{AX}$=9.9 Hz, 1H), 3.91–3.94 (m, 1H), 4.00–4.08 (m, 1H), 4.60–4.68 (m, 1H), 4.75–4.80 (m, obscured by HOD peak, 1H), 5.04 (S, 3H), 8.46 (t, J=7.5 Hz, 1H)8.53 (d, J=9.2 Hz, 1H), 8.70–8.80 (m, 2H), 8.74 (d, J=9.2 Hz, 1H), 9.27, (d, J=1.7 Hz, 1H), 9.32 (d, J=8.4 Hz, 1H), 10.18 (s, 1H).

I.R. (KBr) 1750, 1600 cm$^{-1}$ U.V. (MOPS BUFFER) $\lambda_{ext}$=293 nm, $\epsilon_{ext}$=3000.

EXAMPLE 5

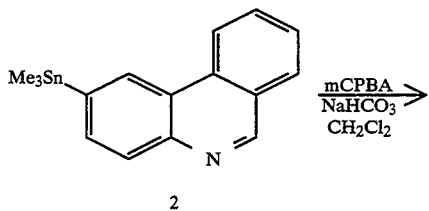

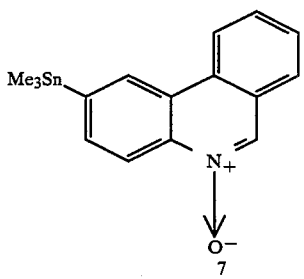

To phenanthridine 2, prepared as described in Example 1 (73.2 mg; 0.214 mmol) in CH$_2$Cl$_2$ (4.3 mL) cooled to 0° C. under N$_2$ was added aqueous NaHCO$_3$ (1.7 mL; 0.214 mmol; 1 equiv) followed by mCPBA (40.6 mg; 0.235 mmol; 1.1 eq). After allowing the reaction to stir for 2 hours at ambient temperature a 5% aqueous solution of Na$_2$S$_2$O$_3$ (5 mL) was added. The reaction mixture was stirred for one hour before being poured into Et$_2$O. The organic layers were washed with H$_2$O (1×), brine (2×), dried over MgSO$_4$, filtered and evaporated. Purification via SiO$_2$ flash column chromatography (100% EtOAc→20% MeOH/EtOAc) provided stannane 7.

$^1$H NMR (400 MHz, CDCl$_3$) δ0.42 (s, 9H), 7.66 (t, J=7.8 Hz, 1H), 7.73-7.80 (m, 2H), 7.93 (d, J=8.1 Hz, 1H), 8.56 (d, J=8.4 Hz, 1H), 8.68 (s, 1H), 8.83 (d, J=8.1 Hz, 1H), 8.90 (s, 1H).

EXAMPLE 6

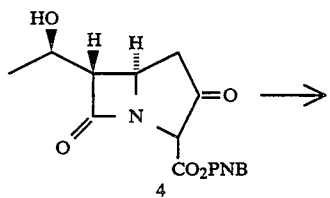

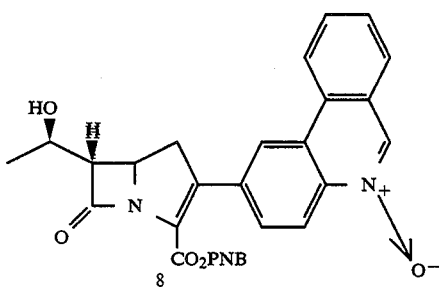

To a stirred solution of the bicyclic β-keto ester 4 (116.7 mg, 0.335 mmol) in dry THF (1.4 mL) at −78° C. under N$_2$ was added diisopropylamine (51.6 μL, 0.369 mmol, 1.1 eq). The resultant yellow mixture was stirred for 10 minutes before trifluoromethanesulfonic anhydride (62 μL, 0.369 mmol, 1.1 eq) was added. After 15 minutes the reaction mixture was treated sequentially with anhydrous N-methyl-2-pyrrolidinone (1.4 mL), the (MeCN)$_2$PdCl$_2$ catalyst (3.6 mg, 1.4×10$^2$ mmol, 5.0 mol %), the aryl-stannane 7 (100 mg, 0.279 mmol) and diisopropylammonium chloride (38 mg; 0.279 mmol). The low temperature bath was then removed and the reaction vessel was placed in a warm water bath to quickly reach ambient temperature. The resulting solution was stirred for 20 minutes at ambient temperature.

The reaction was then poured into EtOAc and washed with water (4×) and brine. The organic layer was dried (Na$_2$SO$_4$), filtered, and evaporated in vacuo. The residue was dissolved in CH$_2$Cl$_2$ and precipitated with Et$_2$O to provide carbapenem 8.

$^1$H NMR (400 MHz, D$_6$ DMSO) δ1.19 (d, J=6.0 Hz, 3H) 3.35 (½ ABX, obscured by H$_2$O peak from DMSO, 1H), 3.49-3.50 (m, 1H), 3.73 (½ ABX, J$_{AB}$=18.9 Hz, J$_{AX}$=8.6 Hz, 1H), 4.00-4.06 (m, 1H), 4.31-4.35 (m, 1H), 5.22 (ABq, J$_{AB}$=13.6 Hz, Δv$_{AB}$=49.8 Hz, 2H), 7.32 (d, J=8.5 Hz, 2H), 7.68-7.72 (m, 2H), 7.83 (d, J=8.8 Hz, 2H), 7.93-7.95 (m, 1H), 8.58 (d, J=8.7, 1H), 8.62-8.64 (m, 1H), 8.80 (s, 1H), 9.08 (s, 1H); I.R. (KBr) 3520, 1750, 1720, 1600, 1510 cm$^{-1}$.

EXAMPLE 7

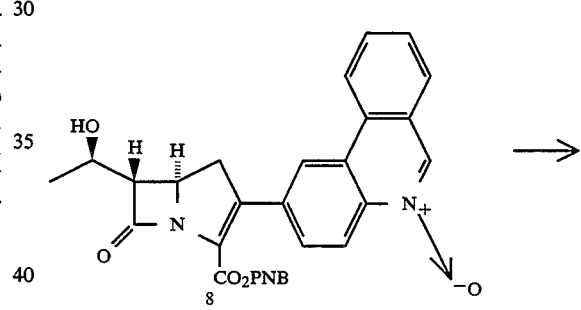

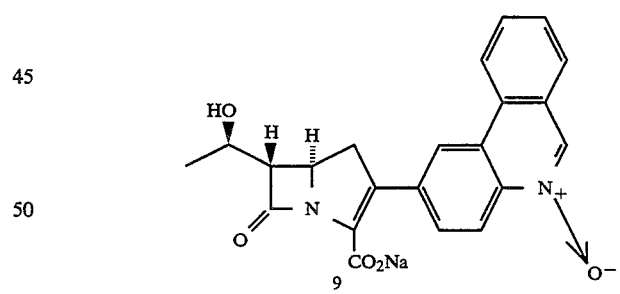

To a stirred solution of 8 (43.6 mg, 0.083 mmol) and sodium bicarbonate solution (87 μL, 0.087 mmol, 1.05 eq) in 2:1 -THF/H$_2$O was added 10% Pd/C catalyst (4.4 mg, 10% wt), and the reaction mixture was hydrogenated under an H$_2$ balloon at ambient temperature for 40 minutes. The mixture was then filtered through a pad of celite, and the THF solvent from the filtrate was removed in vacuo. The remaining water was then frozen and lyophilized at 0° C. Crude 9 was redissolved in a minimal amount of H$_2$O/CH$_3$CN and purified using Analtech reverse phase prep-plates (5:1 H$_2$O/CH$_3$CN) to provide carbapenem 9.

$^1$H NMR (400 MHz, (2:1) D$_2$O/CD$_3$CN) δ 1.70 (d, J=6.4 Hz, 3H), 3.64 (½ ABX, J$_{AB}$=16.6 Hz, J$_{AX}$=9.9

Hz, 1H), 3.91 (dd, J=5.9, 2.8 Hz, 1H), 4.00 (½ ABX, $J_{AB}$=16.7 Hz, $J_{AX}$=8.5, 1H), 4.62–4.65 (m, 1H), 4.75 (dt, J=9.5, 2.9 Hz, 1H), 8.21 (t, J=7.8 Hz, 1H) 8.32–8.36 (m, 2H), 8.43 (d, J=8.0 Hz, 1H), 8.97 (d, J=8.9 Hz, 1H), 9.04–9.07 (m, 2H), 9.45 (s, 1H); U.V. (MOPS BUFFER) $\lambda_{ext1}$, =299 nm, $\epsilon_{ext1}$, =6500; $\lambda_{ext2}$=346 nm, $\lambda_{ext2}$=5600.

EXAMPLE 8

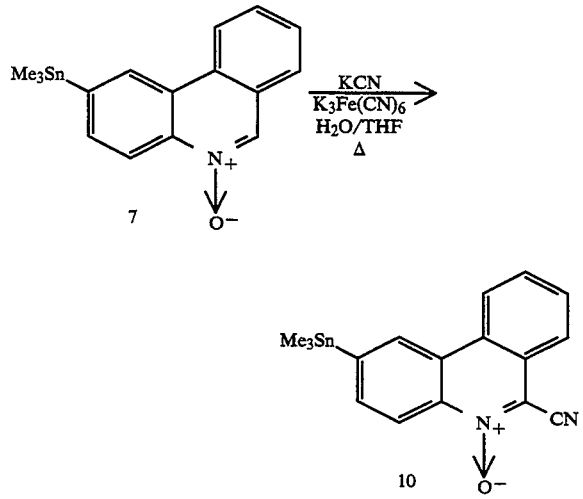

To a solution of KCN (90.9 mg; 1.40 mmol; 5 eq) and $K_3Fe(CN)_6$ (136.3 mg; 0.41 mmol; 1.5 eq) in $H_2O$ (5.6 mL) and THF (1.0 mL) was added phenanthridine N-oxide 7. (100 mg; 0.279 mmol). The suspension was heated to reflux for 3 days. The reaction mixture was cooled to ambient temperature before being poured into $Et_2O$ and washed with $H_2O$ (3×) and brine. The organic layer was dried ($MgSO_4$) filtered and evaporated. Purification by $SiO_2$ column chromatography provided stannane 10.

$^1$H NMR (400 MHz, $CDCl_3$) δ0.44 (s, 9H), 7.70–7.79 (m, 2H), 7.93 (d, J=8.0 Hz, 1H), 8.01 (d, J=8.4 Hz, 1H), 8.54 (d, J=7.7 Hz, 1H), 8.65–8.70 (m, 2H); I.R. ($CHCl_3$)2230, 1560 cm$^{-1}$.

EXAMPLE 9

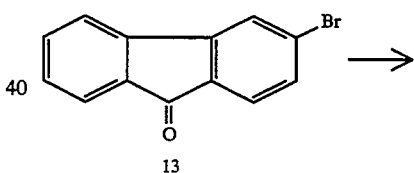

Compound 11 was prepared by the procedure described in Example 6 but substituting the stannane 10 prepared as described in Example 8, and employing 5 mol % $(MeCN)_2PdCl_2$ as the catalyst.

$^1$H NMR (400 MHz, $D_6$ Acetone) δ1.30 (d, J=6.3 Hz, 3H), 3.45 (½ ABX, $J_{AB}$=18.2, $J_{AX}$=10.1, 1H), 3.51 (dd, J=6.4, 2.9 Hz, 1H), 3.79 (½ ABX, $J_{AB}$=18.5 Hz, $J_{AX}$=8.7, 1H), 4.18–4.23 (m, 1H), 4.45–4.50 (m, 1H), 5.27 (ABq, $J_{AB}$=13.4 Hz, $\Delta\nu_{AB}$=64.7 Hz, 2H), 7.45 (d, J=9.1 Hz, 2H), 7.80–8.02 (complex m, 7H), 8.61 (d, J=8.9 Hz, 1H), 8.70 (d, J=8.8 Hz, 1H), 8.88 (d, J=1.7 Hz, 1H); IR (KBr) 3550, 3500–3400, 2230, 1750, 1720, 1600, 1515 cm$^{-1}$.

EXAMPLE 10

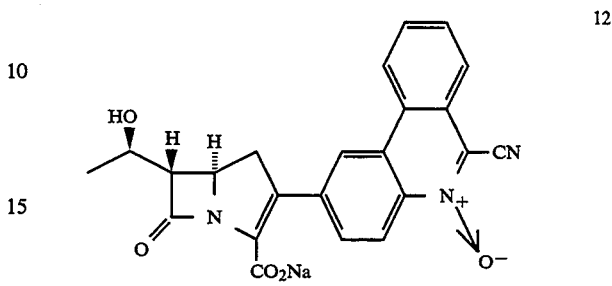

Compound 12 was prepared by the procedure described in Example 7 but substituting the carbapenem 11 prepared as described in Example 9, for the carbapenem 8 and using Pd/C as the catalyst.

$^1$H NMR (400 MHz, (2:1) $D_2O/CD_3CN$) δ1.65 (d, J=6.3 Hz, 3H), 3.60 (½ ABX, $J_{AB}$=16.4 Hz, $J_{AX}$=8.8 Hz, 1H), 3.88 (dd, J=6.1, 2.9 Hz, 1H), 3.94 (½ ABX, $J_{AB}$=16.6 Hz, $J_{AX}$=8.5 Hz, 1H), 4.53–4.61 (m, 1H), 4.72 (dt, J=9.7, 2.9 Hz, 1H), 8.20–8.30 (complex m, 3H), 8.37–8.41 (m, 1H), 8.87 (d, J=9.0 Hz, 1H), 8.87–8.90 (m, 2H); IR (KBr)1750, 1600 cm$^{-1}$; UV (MOPS buffer) $\lambda_{ext}$=305 nm, $\epsilon_{ext}$=5600.

EXAMPLE 11

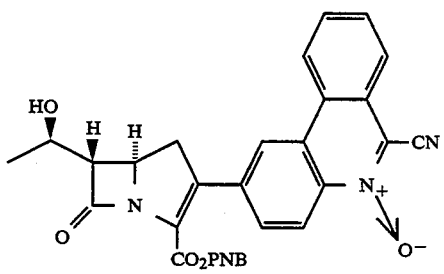

To a stirred solution of 13 (200 mg, 0.77 mmol) in concentrated sulfuric acid (12.9 mL) at 0° C. was added a solution of sodium azide (75.3 mg, 1.16 mmol, 1.5 eq) in water (1 mL). After stirring the resultant black mixture for 24 hours at room temperature, ice-water (10 mL) was added. The reaction mixture was then stirred for 15 minutes, poured into ethyl acetate (200 mL), and washed with saturated sodium bicarbonate solution (2×25 mL), water (2×), and brine. The organic layer was dried ($MgSO_4$), filtered, and evaporated in vacuo to obtain a mixture of 1:1 inseparable bromo-phenanthridone isomers (14 and 15) in 74% yield (156 mg).

EXAMPLE 12

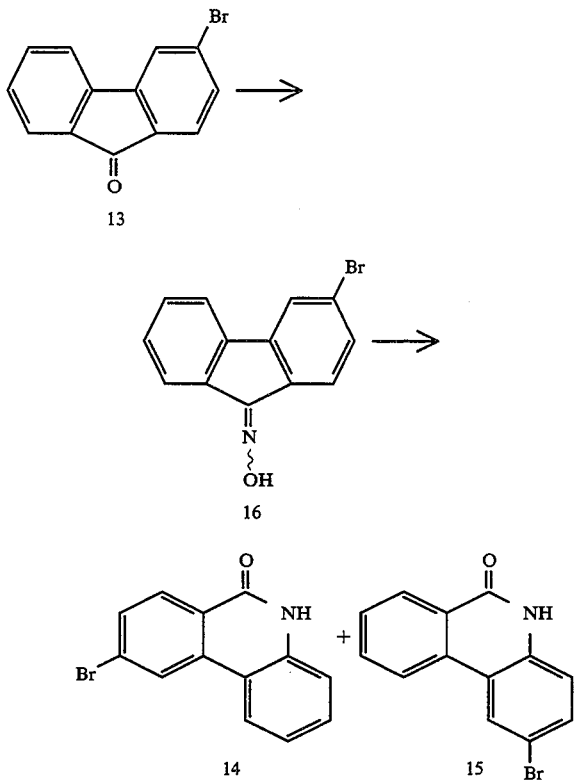

A suspension of 13 (200 mg, 0.77 mmol) and hydroxylamine hydrochloride (161 mg, 2.32 mmol, 3.0 eq) in anhydrous pyridine (7.7 mL) was sonicated to afford dissolution. The homogeneous mixture was then stirred at room temperature for 3.5 hour and poured into ether (100 mL). The ethereal layer was washed with water (1×), 1N HCl solution (4×15 mL), saturated sodium bicarbonate solution (2×15 mL), water (2×), and brine. The organic layer was dried (MgSO$_4$), filtered, and evaporated in vacuo to afford 200 mg (95%) of the hydroxylamine isomers 16, a white solid. [The hydroxylamine isomers mixture 16 was not separated or characterized and was taken to the next step].

A mixture of 16 (104 mg, 0.38 mmol) in an excess amount of polyphosphoric acid (9g) was heated to 200° C. After 30 minutes the resultant black paste was dissolved in ice-water (50 mL) and extracted with ethyl acetate (3×50 mL). The combined organic layers were then washed with saturated sodium bicarbonate solution (3×25 mL), water (2×), and brine. The organic layer was dried (MgSO$_4$), filtered, and evaporated in vacuo. The inseparable 1:1 mixture of the phenanthridone isomers (14 and 15) was isolated in 96% yield (100 mg) as a beige solid.

$^1$H-NMR for 14/15 [300 MHz, D$_6$ DMSO, mixture]: δ7.24 to 7.38 (m, 3H), 7.52 (t, J=6.9 Hz, 1H), 7.64 to 7.71 (m, 2H), 7.79 to 7.89 (m, 2H), 8.22 (d, J=8.5 Hz, 1H), 8.32 (d, J=7.4 Hz, 1H), 8.45 (d, J=7.8 Hz, 1H), 8.56 to 8.60 (m, 2H), 8.75 (s, 1H). IR (KBr): 3020, 2880, 1685, 1610 cm$^{-1}$. Fast atom bombardment mass spectrum: m/e 274, 276 (calculated MH+ C$_{13}$H$_8$BrNO=274, 276).

EXAMPLE 13

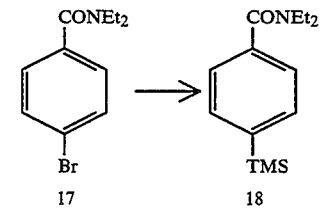

Chlorotrimethylsilane (10.4 mL, 81.9 mmol, 3.0 eq) was added to a stirred solution of 17 (7.0 g, 27.3 mmol) in dry THF (103 mL) at −78° C. under N$_2$. Tert-butyllithium (23.1 mL, 30 mmol, 1.1 eq) was added dropwise at −78° C. over 45 minutes. The reaction mixture was warmed to 0° C. with an ice bath and then quenched with saturated ammonium chloride solution (25 mL). After removal of THF in vacuo the reaction mixture was poured into ether (400 mL) and washed with water, saturated sodium bicarbonate solution (2×50 mL), water, and brine. The ethereal layer was dried (MgSO$_4$), filtered, and evaporated in vacuo. Purification using flash chromatography (20% EtOAc/hex) afforded 5.7 g (87%) of aryl silane 18, a white solid.

$^1$H-NMR for 18 [400 MHz, CDCl$_3$, rotamers]: δ0.24 (s, 9H), 1.08 (broad s, 3H), 1.21 (broad s, 3H), 3.23 (broad s, 2H), 3.51 (broad s, 2H), 7.30 (d, J=8.1 Hz, 2H), 7.50 (d, J=8.1 Hz, 2H). IR(CHCl$_3$): 3010, 1615 cm$^{-1}$.

EXAMPLE 14

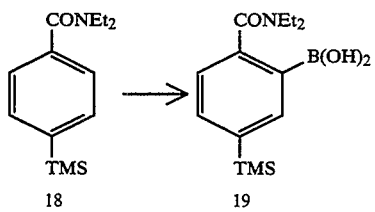

To a stirred solution of N,N,N',N'-tetramethylethylenediamine (2.7 mL, 17.6 mmol, 1.1 eq) in anhydrous THF (100 mL) at −78° C. under N$_2$ was added dropwise sec-butyllithium (13.0 mL, 16.8 mmol, 1.05 eq). After 15 minutes the yellow mixture was treated with a solution of 18 (4.0 g, 16.0 mmol) in dry THF (40 mL), and the resultant red mixture was stirred for 1 hour at −78° C. Trimethylborate (2.0 mL, 17.6 mmol, 1.1 eq) was added dropwise. The reaction flask was warmed to 0° C. with an ice bath and then stirred for 5 minutes. The green reaction mixture was quenched with 8% HCl solution (60 mL), stirred for 10 minutes, and the organic solvent concentrated in vacuo. The mixture was poured into ether and the ethereal layer was washed with water (2×), brine, dried (MgSO$_4$), filtered, and evaporated in vacuo. Purification using flash chromatography (5:3:1 EtOAc/acetone/H$_2$O) provided 3.77 g (80%) of boronic acid 19, a white foam.

$^1$H-NMR for 19 [200 MHz, CDCl$_3$, rotamers]: δ0.27 (s, 9H), 0.88 to 1.16 (m, 6H), 3.27 to 3.36 (m, 4H), 7.28 (d, J=6.4 Hz, 1H), 7.52 (d, J=7.6 Hz, 1H), 8.15 (s, 1H). IR(CHCl$_3$): 2960, 1615, 1601 cm$^{-1}$.

EXAMPLE 15

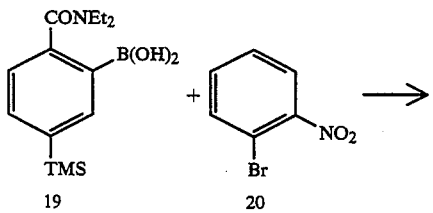

Aqueous sodium carbonate (2.66 mL, 5.32 mmol, 2.0 eq) was added to a stirred solution of 19 (779.3 mg, 2.7 mmol) and tetrakis(triphenylphosphine) palladium (O) (153.7 mg, 5.0 mol %) in toluene (10.6 mL). The resulting two-phase mixture was stirred for 10 minutes under $N_2$ at room temperature. A solution of 20 (590.5 g, 9.6 mmol, 1.1 eq) dissolved in absolute ethanol (5 mL) was added, and the heterogeneous mixture was stirred for 3 hours at reflux under $N_2$. The cooled reaction mixture was poured into ether (175 mL) and washed with water (1×), saturated sodium carbonate solution (2×25 mL), water (1×), and brine. The organic layer was dried ($MgSO_4$), filtered, and evaporated in vacuo. Purification using flash chromatography (60% EtOAc/hex) provided 812.5 mg (82.5%) of the biphenyl compound 21, a yellow foam.

$^1$H-NMR for 21 [400 MHz, $CDCl_3$, rotamers]; δ0.24 (s, 9H), 0.80(t, J=7.1 Hz, 3H), 0.91(t, J=7.1 Hz, 3H), 2.80 to 3.67 (broad, 4H), 7.30 to 7.33 (m, 2H), 7.46 (t, J=8.1 Hz, 1H), 7.52 to 7.58 (m, 3H), 7.90 (d, J=8.8 Hz, 1H). IR ($CHCl_3$): 3000, 2980, 1610, 1580, 1525 cm$^{-1}$.

EXAMPLE 16

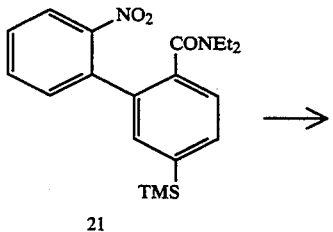

Iodine monochloride in dichloromethane (10.9 mL, 10.9 mmol, 5.0 eq) was added dropwise over 0.5 hour to a stirred solution of 21 (812.5 mg, 2.19 mmol) in dry dichloromethane (10.9 mL). The reaction mixture was then poured in ether (200mL) and washed with saturated sodium thiosulfate solution (2×25 mL), water, saturated bicarbonate solution (2×25 mL), water and brine. The etheral layer was then dried ($MgSO_4$), filtered, and evaporated in vacuo. Purification using flash column chromatography (30% EtOAc/hex) afforded 887.7 mg (95.4%) of 22, a yellow foam.

$^1$H-NMR for 22 [400 MHz, $CDCl_3$, rotamers]: δ0.75 (t, J=7.0 Hz, 3H), 0.93 (t, J=7.0 Hz, 3H), 2.82 to 3.60 (broad, 4H), 7.07 (d, J=8.1 Hz, 1H), 7.46 to 7.51 (m, 2H), 7.56 to 7.60 (m, 2H), 7.73 (d, J=8.1 Hz, 1H), 7.97 (d, J=8.1 Hz, 1H). IR ($CHCl_3$): 3000, 2980, 1620, 1580, 1525 cm$^{-1}$.

EXAMPLE 17

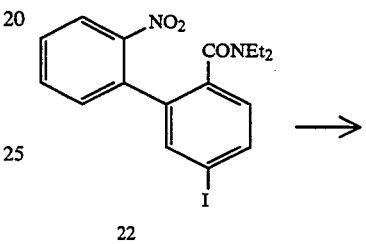

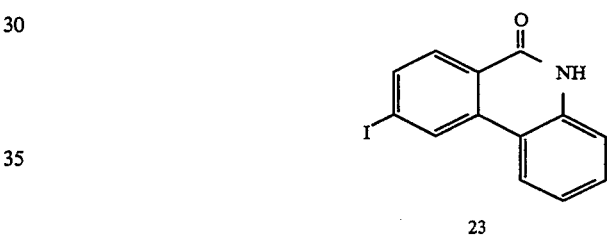

To a stirred solution of 22 (158.0 mg, 0.37 mmol) in 3:2:2 AcOH/EtOH/THF (7.0 mL) was added iron powder (103.8 mg, 1.86 mmol, 5.0 eq), and the reaction mixture was stirred at reflux until a white solid had separated (30 minutes). The reaction mixture was poured into ethyl acetate (200 mL) and washed with saturated sodium bicarbonate solution (1×25 mL), water, and brine. The organic layer was dried ($MgSO_4$) filtered and evaporated in vacuo. Chloroform (~10 mL) was added and the product was filtered to afford 119.0 mg (99.5%) of 23, a white solid.

$^1$H-NMR for 23 [400 MHz, $D_6$ DMSO]: δ7.24 (t, J=7.7 Hz, 1H), 7.34 (d, J=8.1 Hz, 1H), 7.50 (t, J=7.6 Hz, 1H), 8.42 (d, J=8.1 Hz, 1H), 8.89 (s, 1H). IR(KBr): 3010, 2990, 2870, 1665, 1600, 1585 cm$^{-1}$.

EXAMPLE 18

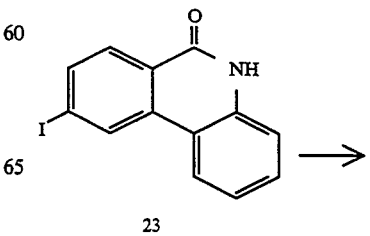

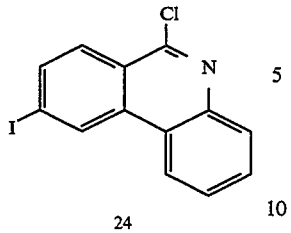

To phenanthridone 23 (50 mg; 0.156 mmol) and PCl$_5$ (32.5 mg; 0.156 mmol; 1.0 eq) was added excess POCl$_3$ (2.5 mL). The reaction was heated to reflux for 5 hours, cooled and quenched by pouring onto ice. The aqueous layer was extracted with CHCl$_3$. The organic layer was dried over MgSO$_4$, filtered and evaporated to provide phenanthridine 24 slightly contaminated with some starting material 23.

$^1$H NMR(400 MHz, CDCl$_3$) δ7.69 (dt, J=8.2, 1.3 Hz, 1H), 7.76 (dt, J=7.2, 1.4 Hz, 1H), 8.02–8.08 (m, 2H), 8.16 (d, 8.8 Hz, 1H), 8.45 (d, 7.1 Hz, 1H), 8.97 (d, J=1.6 Hz, 1H)

EXAMPLE 19

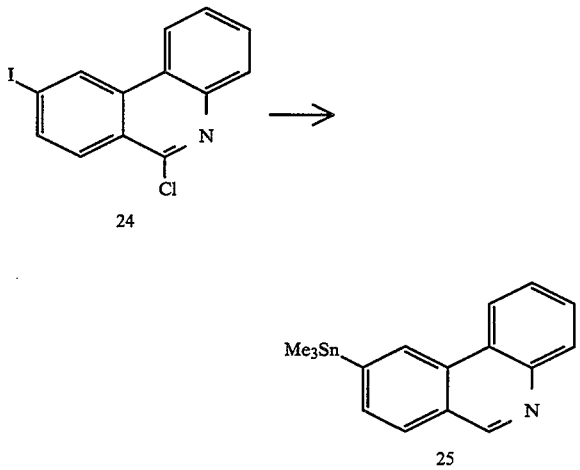

To phenanthridine 24 (170 mg; 0.50 mmol) in toluene (5 mL) was added Me$_3$SnSnMe$_3$ (180 mg; 0.55 mmol; 1.1 eq), Pd(PPh$_3$)$_4$ (29 mg; 0.025 mmol; 5 mol %) and triphenylphosphine (3.9 mg; 0.015 mmol; 3 mol %). After bubbling N$_2$ through the reaction mixture for 15 minutes, the vessel was heated to reflux for 3 hours. The reaction was cooled, poured into Et$_2$O and washed with H$_2$O (1×), saturated NaHCO$_3$ solution (1×), H$_2$O (2×) and brine. The organic layer was dried (MgSO$_4$), filtered and evaporated. Purification by flash chromatography (20% EtOAc/hex) provided 25.

$^1$H NMR (400 MHz, CDCl$_3$) δ0.42 (s, 9H), 7.65–7.75 (m, 2H), 7.81 (d, J=7.7 Hz, 1H), 7.96 (d, J=7.7 Hz, 1H), 8.17 (dd, J=8.1, 1.3 Hz, 1H), 8.63 (dd, 8.1, 1.4 Hz, 1H), 8.74 (s, 1H), 9.25 (s, 1H).

EXAMPLE 20

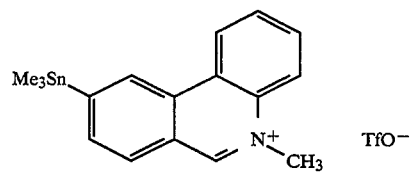

Compound 26 was prepared by the procedure described in Example 2 but substituting the stannane 25, obtained as described in Example 19, for stannane 2. $^1$H NMR (400 MHz, CDCl$_3$) δ0.48 (s, 9H), 4.82 (s, 3H), 8.03–8.09 (m, 3H), 8.13 (d, J=7.8 Hz, 1H), 8.29 (d, J=7.9 Hz, 1H), 8.61 (d, J=8.0 Hz, 1H), 8.87 (s, 1H), 8.90 (d, J=7.4 Hz, 1H), 10.46 (s, 1H).

EXAMPLE 21

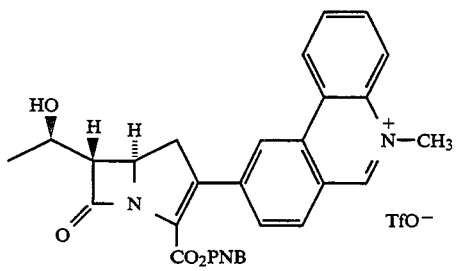

Compound 27 was prepared by the method described in Example 3 but substituting the stannane 26, obtained as described in Example 20, for stannane 3. $^1$H NMR (400 MHz, D$_6$-Acetone) δ1.30 (d, J=6.2 Hz, 3H), 3.50 (½ ABX, J$_{AB}$=18.2 Hz, J$_{AX}$=10.2 Hz, 1H), 3.56 (dd, J=6.2, 3.2 Hz, 1H), 3.91 (½ ABX, J$_{AB}$=18.3 Hz, J$_{AX}$=8.4 Hz, 1H), 4.19–4.23 (m, 1H), 4.49–4.55 (m, 1H), 4.91 (s, 3H), 5.61 (ABq, J$_{AB}$=13.6 Hz, Δv$_{AB}$=71.7 Hz, 2H), 7.47 (d, J=8.7 Hz, 2H), 7.91 (d, J=8.8 Hz, 2H), 8.09–8.22 (complex m, 3H), 8.59–8.63 (m, 2H), 9.08 (d, J=8.1 Hz, 1H), 9.12 (s, 1H), 10.26 (s, 1H); IR (KBr) 3680–3200, 1775, 1720, 1625, 1600, 1520 cm$^{-1}$; UV (CH$_3$CN) λ=374 nm; ε=13,000.

EXAMPLE 22

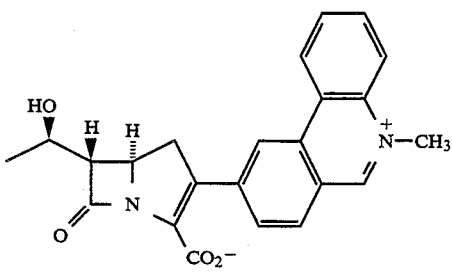

(5R, 6S)-2-(5-Methyl-9-phenanthridinyl )-6-( 1R-hydroxyethyl)carbapen-2-em-3-carboxylate Carbapenem 28 was prepared by the procedure described in Example 4, but substituting the carbapenem 27, obtained as described in Example 21, for carbapenem 5. $^1$H NMR (400 MHz (2:1) D$_2$O/CD$_3$CN) δ1.74 (d, J=6.2 Hz, 3H), 3.72 (½ ABX, J$_{AB}$=16.4 Hz, $J_{AX}=9.8$ Hz, 1H), 3.98–4.02 (m, 2H), 4.10 (½ ABX, $J_{AB}=16.5$ Hz, $J_{AX}=11.0$ Hz, 1H), 4.62–4.70 (m, 1H), 4.8–4.85 (obscured by HOD peak, 1H), 5.05 (s, 3H), 8.48 (d, J=8.3 Hz, 1H), 8.50–8.59 (complex m, 2H), 8.82 (d, J=8.3 Hz, 2H), 9.21 (s, 1H), 9.40 (d, J=7.4 Hz, 1H), 10.16 (s, 1H); I.R. (KBr) 1760, 1600 cm$^{-1}$ ; U.V. (MOPS BUFFER) $\lambda_{ext}=390$ nm, $\epsilon_{ext}=6800$.

EXAMPLE 23

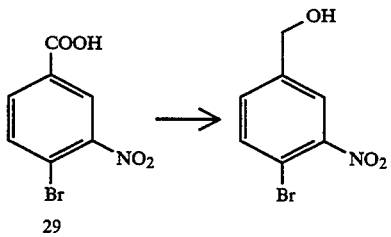

To a stirred solution of 4-bromo-3-nitrobenzoic acid (5.0 g, 20.3 mmol) in dry THF (40.6 mL) under $N_2$ at room temperature was added dropwise the borane-tetrahydrofuran complex (40.6 mL, 40.6 mmol, 2.0 eq). After stirring at reflux for 1 hour the reaction mixture was quenched with dropwise addition of triethylamine (1 mL) in methanol (50 mL) at 0° C. The solvent was then removed in vacuo to give crude 4. Purification using flash chromatography (30% EtOAc/hex) provided 4.5 g (96%) of 29, an off-white solid.

$^1$H-NMR for 29 [400 MHz, CDCl$_3$]: δ1.86 (t, J=5.8 Hz, 1H), 4.74 (d, J=5.8 Hz, 2H), 7.41 (dd, J=8.3, 2.1 Hz, 1H), 7.70 (d, J=8.3 Hz, 1H), 7.85 (s, 1H). IR(CHCl$_3$): 3605, 3500 to 3200, 3010, 2880, 1605, 1535, 1355 cm$^{-1}$.

EXAMPLE 24

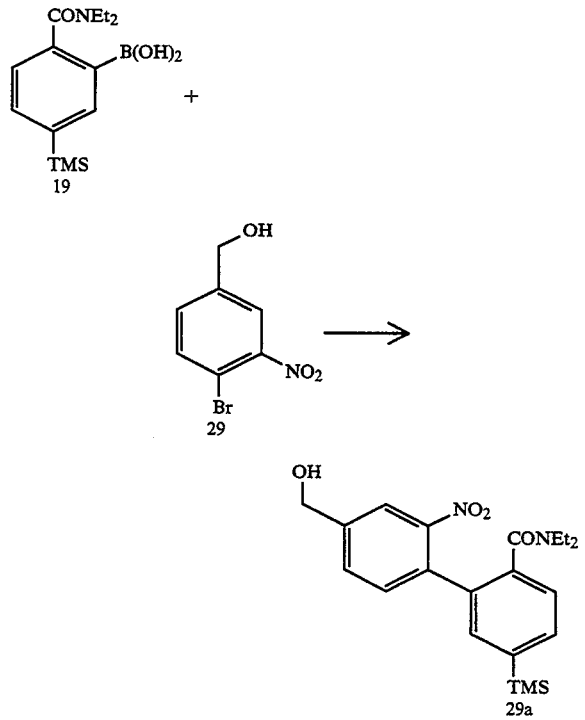

Aqueous sodium carbonate (8.7 mL, 17.4 mmol, 2.0 eq) was added to a stirred solution of 19 (2.0 g, 8.7 mmol) and tetrakis(triphenylphosphine)palladium (O) (502.8 mg, 5.0 mol %) in toluene (33.5 mL). The resulting two-phase mixture was stirred for 10 minutes under $N_2$ at room temperature. A solution of 29 (2.8 g, 9.6 mmol, 1.1 eq) dissolved in absolute ethanol (9.6 mL) was added, and the heterogeneous mixture was stirred for 3 hours at reflux under $N_2$. The cooled reaction mixture was poured into ether (175 mL) and washed with water (1×), saturated sodium carbonate solution (2×25 mL), water (1×), and brine. The organic layer was dried (MgSO$_4$), filtered, and evaporated in vacuo. Purification using flash chromatography (60% EtOAc/hex) provided 2.9 g (83%) of the biphenyl compound 29a, a yellow foam.

$^1$H-NMR for 29a [400 MHz, CDCl$_3$, rotamers]: δ0.24 (s, 9H), 0.87 (t, J=7.1 Hz, 3H), 0.94 (t, J=7.1 Hz, 3H), 2.40 (broad s, 1H), 2.72 to 3.65 (broad, 4H), 4.76 (s, 2H), 7.30 to 7.32 (m, 2H), 7.51 to 7.56 (m, 3H), 7.93 (s, 1H). IR(CHCl$_3$): 3360, 3520 to 3300, 2990, 1620, 1605, 1530 cm$^{-1}$.

EXAMPLE 25

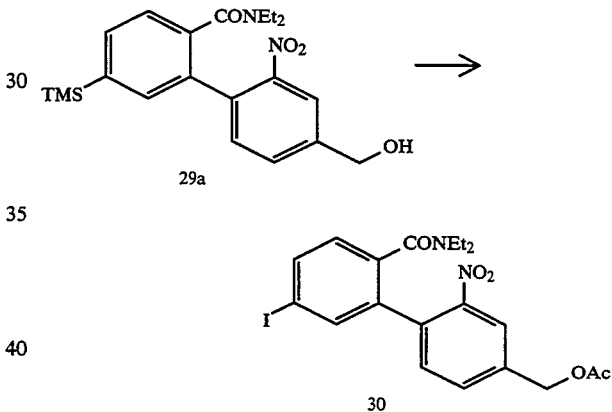

Acetic anhydride (6.8 mL, 72.4 mmol, 10.0 eq) was added to a stirred solution of 29a (2.9 g, 7.24 mmol) in dry pyridine (36 mL). The reaction mixture was stirred for 25 minutes at room temperature under $N_2$. The solvent was removed in vacuo and the residual oil azeotroped from toluene. The crude acetate was redissolved in dry dichloromethane (20 mL), and a 1.0M solution of iodine monochloride in dichloromethane (33 mL, 33.3 mmol, 4.6 eq) was added dropwise over 1 hour using an addition funnel. The reaction mixture was then poured into ether (250 mL) and the organic layer was washed with saturated sodium thiosulfate solution (3×30 mL), water (1×), saturated sodium bicarbonate solution (1×30 mL), water (1×), and brine. The organic layer was dried (MgSO$_4$), filtered, and evaporated in vacuo to afford 3.6 g (quantitative yield) of 30, a yellow oil.

$^1$H-NMR for 30 [400 MHz, CDCl$_3$, rotamers]: δ0.81 (t, J=7.1 Hz, 3H), 0.98 (t, J=7.1 Hz, 3H), 2.14 (s, 3H), 2.78 to 3.65 (broad, 4H), 5.17 (s, 2H), 7.08 (d, J=8.1 Hz, 1H), 7.49 to 7.61 (m, 3H), 7.76 (d, J=8.0 Hz, 1H), 7.97 (s, 1H). IR(CHCl$_3$): 3010, 1745, 1610, 1530 cm$^{-1}$.

EXAMPLE 26

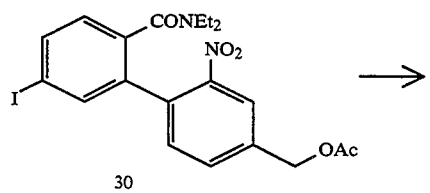

30

A solution of 25% sodium methoxide in methanol (0.53 mL, 2.4 mmol, 1.1 eq) was added to a stirred solution of 30(1.1 g, 2.2 mmol) in dry methanol (11.0 mL). The reaction mixture was stirred for 10 minutes at room temperature under $N_2$. Acetic acid (6.0 mL) and dry tetrahydrofuran (11.0 mL) were then added. Iron powder (371.9 mg, 6.7 mmol, 3.0 eq) was added next, and the reaction mixture was stirred at reflux until a white solid had separated (approximately 15 minutes). The reaction mixture was cooled, poured into ice water (250 mL), and the solid filtered. The crude cyclized product was redissolved in hot ethanol (250 mL), filtered through a hot-sintered glass funnel, and the solvent removed in vacuo. Recrystallization from ethanol provided 501 mg (64%) of the cyclized amide 31, a white fluffy solid.

$^1$H-NMR for 31 [400 MHz, d$_6$-DMSO]: δ4.57 (s, 2H), 5.36 (t, J=5.7 Hz, 1H), 7.16 (d, J=8.2 Hz, 1H), 7.33 (s, 1H), 7.93 (d, J=8.4 Hz, 1H), 8.00 (d, J=8.4 Hz, 1H), 8.35 (d, J=8.4 Hz, 1H), 8.85 (s, 1H), 11.74 (s, 1H). IR (KBr): 1670, 1601 cm$^{-1}$.

EXAMPLE 27

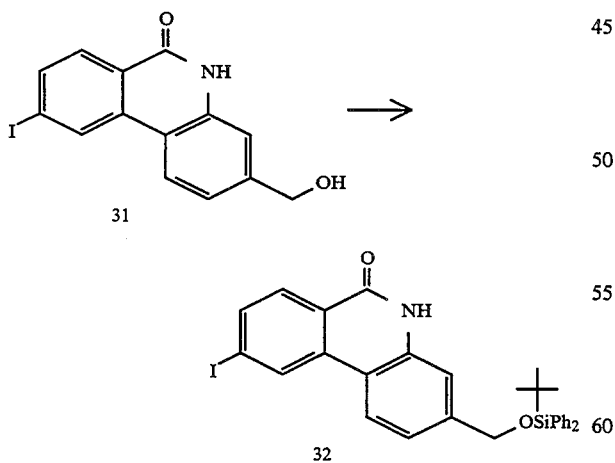

2-iodo-8-(t-butyldiphenylsilyloxymethyl)-phenanthridone

To a solution of 2-iodo-8-(hydroxymethyl) phenanthridone 31 and t-butyldiphenylsilyl chloride in CH$_2$Cl$_2$ and THF are added triethylamine followed by 4-dimethylaminopyridine. After stirring at room temperature until chromatographic analysis indicates complete reaction, the solution is poured into ethyl ether and washed successively with sat. NAHCO$_3$, H$_2$O, and brine. Drying (Na$_2$SO$_4$) and evaporation provides the crude product which is purified by flash chromatography to provide the title compound 32.

EXAMPLE 28

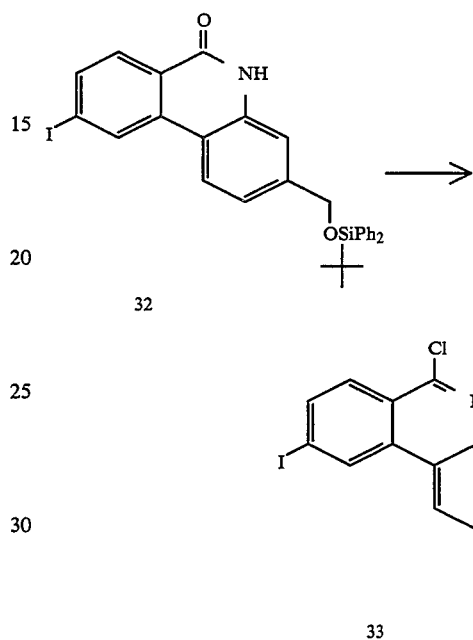

To a mixture of phenanthridone 32 and PCl$_5$ is added a molar excess of POCl$_3$. The reaction is heated to reflux until chromatographic analysis indicates complete reaction, cooled and quenched by pouring onto ice. The aqueous layer is extracted with CHCl$_3$. The organic layer is dried over MgSO$_4$, filtered and evaporated to provide phenanthridine 33.

EXAMPLE 29

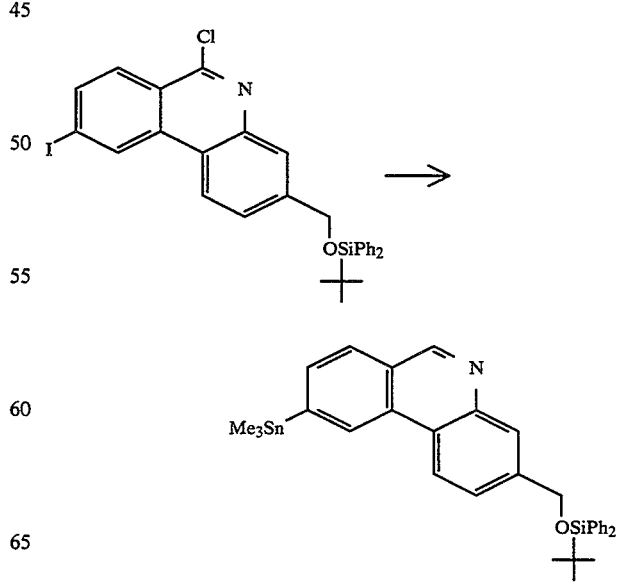

To a solution of phenanthridine 33 in toluene is added Me₃SnSnMe₃, Pd(PPh₃)₄ and triphenyl phosphine. After N₂ is bubbled through the reaction mixture for 15 minutes, the vessel is heated to reflux until chromatographic analysis indicates complete reaction. The reaction is cooled, poured into ether and the organic solution is washed with H₂O (1×), saturated NaHCO₃ solution (1×), H₂O (2×) and brine. The organic layer is dried over MgSO₄, filtered and evaporated to provide the crude product. The crude product is purified by flash chromatography to provide the compound 34.

EXAMPLE 30

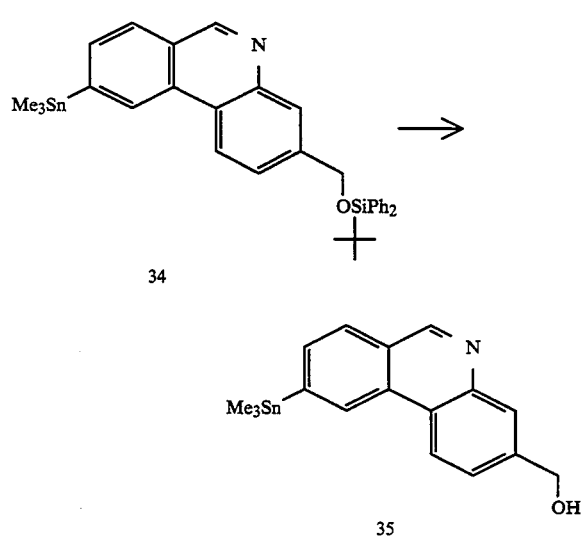

To a solution of the phenanthridine 34 is THF is added a 1.0M solution of nBu₄NF in THF. The reaction solution is stirred until chromatographic analysis indicates complete reaction and then poured into EtOAC. The organic solution is washed with saturated aqueous NaHCO₃ (2×) and brine, then is dried over MgSO₄ and filtered. The solution is concentrated in vacuo and purified by flash chromatography to provide the phenanthridine 35.

EXAMPLE 31

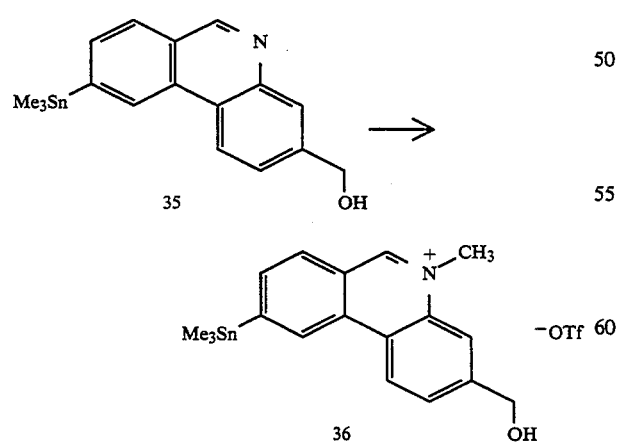

Employing the procedure described in Example 2, but substituting the hydroxymethylphenanthridinyl stannane 35 prepared as described in Example 30 for the stannane 2, provides the N-methyl hydroxymethylphenanthridinyl stannane 36.

EXAMPLE 32

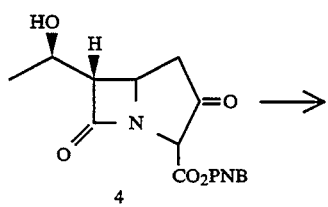

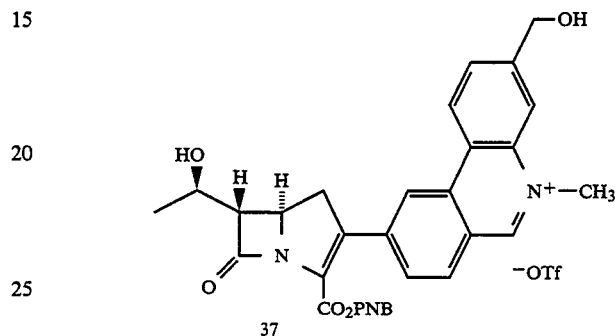

Employing the procedure described in Example 3, but substituting the N-methyl hydroxymethylphenanthridinyl stannane 36 prepared as described in Example 31 for the stannane 2, provides the carbapenem 37.

EXAMPLE 33

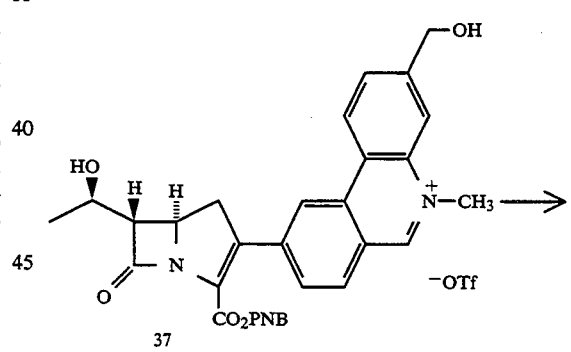

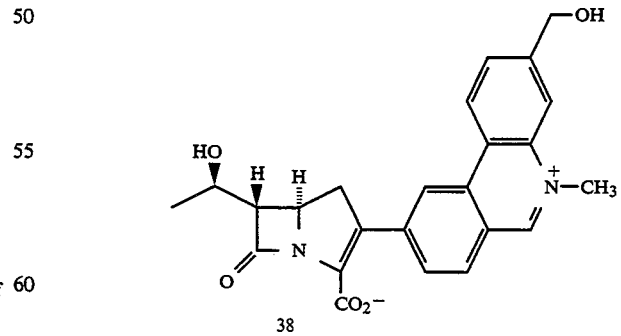

Employing the procedure described in Example 4, but substituting the 5-methyl-3-hydroxymethylphenanthridinyl carbapenem 37 prepared as described in Example 32 for the carbapenem 5, provides the carbapenem 38.

EXAMPLE 34

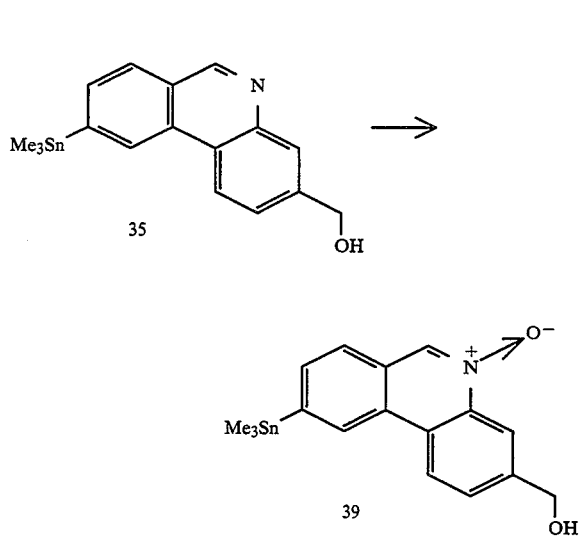

Employing the procedure described in Example 5, but substituting the hydroxymethylphenanthridinyl stannane 35 prepared as described in Example 30 for the stannane 2, provides the hydroxymethylphenanthridinyl N-oxide 39.

EXAMPLE 35

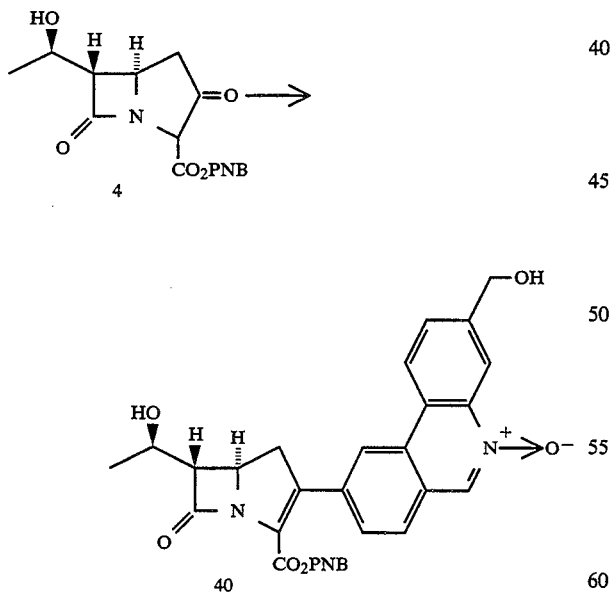

Employing the procedure described in Example 3, but substituting the N-methyl hydroxymethylphenanthridinyl stannane 39 prepared as described in Example 34 for the stannane 3, provides the carbapenem 40.

EXAMPLE 36

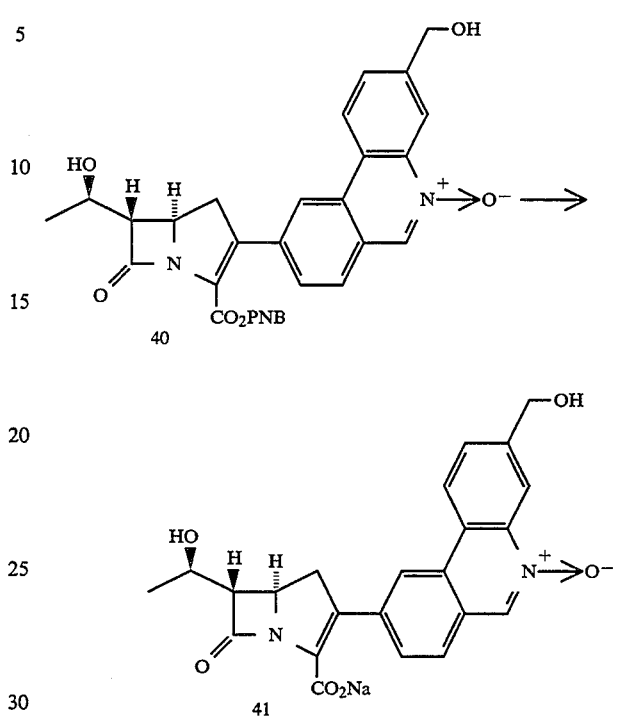

Employing the procedure described in Example 4, but substituting the 5-methyl-3-hydroxymethylphenanthridinyl carbapenem 40 prepared as described in Example 35 for the carbapenem 5, provides the carbapenem 41.

EXAMPLE 37

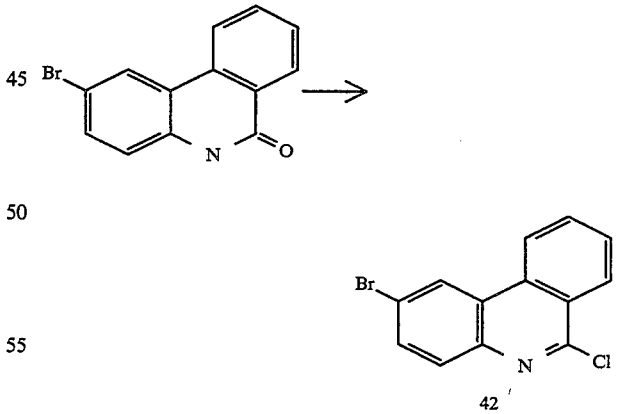

Following the procedure described in Example 18, but substituting 2-bromophenanthridone, obtained by the procedure described by L. W. Mosby, J. Chem. Soc., Vol. 76, pp 936(1954), for the iodo phenanthridone 23, phenanthridine 42 was obtained.

$^1$H NMR (400 MHz, CDCl$_3$) δ7.77–7.85 (m, 2H), 7.89–7.96 (m, 2H), 8.48 (d, J=7.9 Hz, 1H), 8.53 (d, J=8.1 Hz, 1H), 8.65 (d, J=2.0 Hz, 1H).

EXAMPLE 38

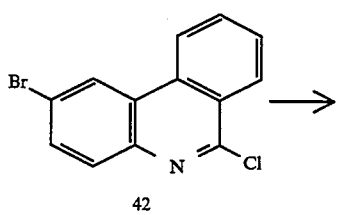

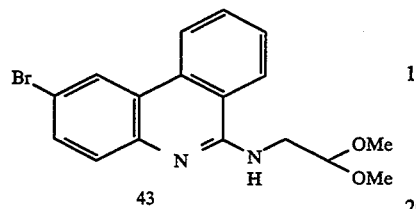

To a mixture of 42 (600 mg; 2.05 mmol) and ground 4 Å molecular sieves in anhydrous DME was added amino dimethylacetaldehyde (1.2 mL; 10.3 mmol; 5 equiv). The mixture was heated at 100° C. for 2 days. After cooling, the reaction mixture was poured into EtOAc and washed with $H_2O$ (1×), 1N HCl (3×), $H_2O$ (1×), saturated $NaHCO_3$ solution (1×), $H_2O$ (2×) and brine. The organic layer was dried ($MgSO_4$), filtered and the solvent removed in vacuo. Purification via $SiO_2$ flash column chromotography (30% EtOAc/Hex) afforded compound 43.

$^1$H NMR (400 MHz, CDCl$_3$) δ3.47 (s, 6H), 3.89 (dd, $J_1=J_2=5.4$ Hz, 2H), 4.68 (dd, $J_1=J_2=5.2$ Hz, 1H), 5.58–5.68 (b, 1H), 7.55–7.65 (m, 3H), 7.76 (t, J=7.1 Hz, 1H) 7.85 (d, J=7.0 Hz, 1H), 8.41–8.43 (m, 2H); IR (CHCl$_3$) 3470, 1590 cm$^{-1}$.

EXAMPLE 39

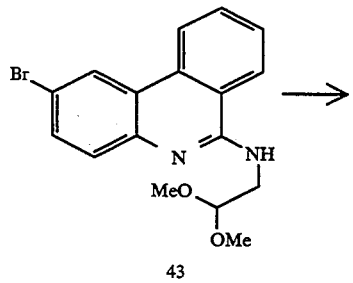

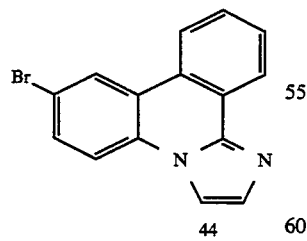

Compound 43 (308 mg; 0.853 mmol) was dissolved in 5N HCl (30 mL) and heated to reflux overnight. The resulting homogeneous solution was cooled to ambient temperature and poured onto crushed ice. The pH of the solution was adjusted to 7–8 using 50% NaOH solution. Following extraction with EtOAc, the organic layer was dried (MgSO$_4$), filtered and evaporated. The residual oil was purified via SiO$_2$ flash column chromatography (100% EtOAc) to afford compound 44.

$^1$H NMR (200 MHz CDCl$_3$) δ7.60–7.75 (complex m, 5H), 7.95 (d, J=1.4 Hz, 1H), 8.25–8.35 (m, 1H), 8.57 (d, J=1.6 Hz, 1H), 8.63–8.68 (m, 1H); IR (CHCl$_3$) 3000–2920, 1545 cm$^{-1}$.

EXAMPLE 40

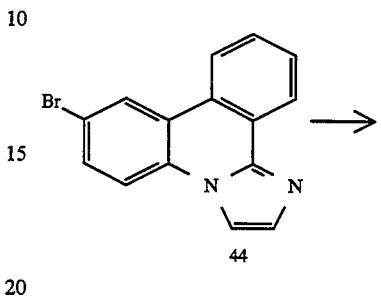

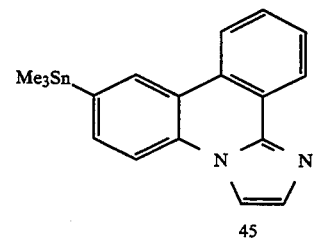

Following the procedure described in Example 1, but substituting aryl bromide 44 for aryl bromide 1, compound 45 was obtained.

$^1$H NMR (500 MHz, CDCl$_3$) δ0.40 (s, 9H), 7.59 (s, 1H), 7.61–7.63 (m, 2H), 7.69 (d, J=8.0 Hz, 1H) 7.81 (d, J=8 Hz, 1H), 7.97 (s, 1H), 8.41–8.43 (m, 1H), 8.54 (s, 1H), 8.67 (m, 1H); IR (CHCl$_3$) 2970, 1590, 1525 cm$^{-1}$.

EXAMPLE 41

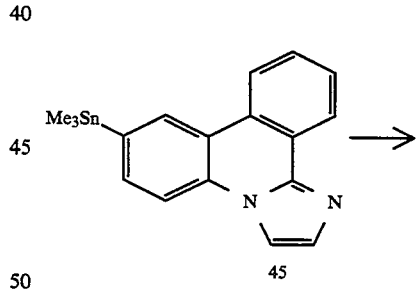

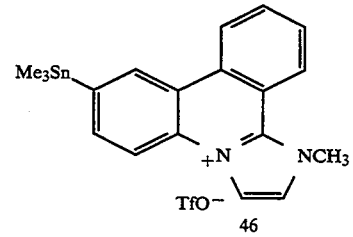

Following the procedure described in Example 2, but substituting aryl bromide 45 for aryl bromide 2, provided compound 45.

$^1$H NMR (200 MHz, D$_6$ Acetone) δ0.47 (s, 9H), 4.76 (s 3H), 7.90–8.20 (complex m, 3H), 8.36 (d, J=2.3 Hz, 1H), 8.58 (d, J=8.2 Hz, 1H), 8.96 (d, J=9.2 Hz, 1H), 9.08–9.18 (m, 3H); IR (CHCl$_3$) 1600 cm$^{-1}$.

EXAMPLE 42

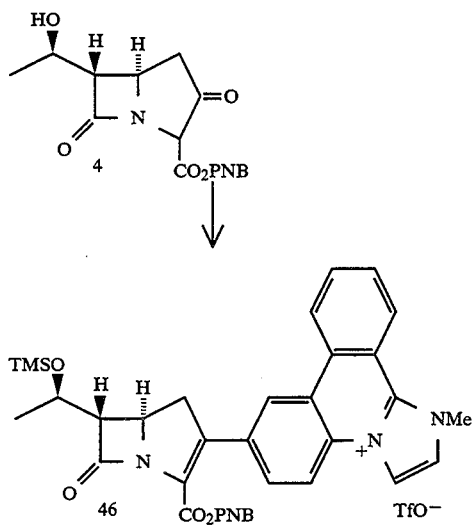

Employing the procedure described in Example 3, but substituting the stannane 46 for the aryl stannane 3, and using the activated ADC-13 intermediate in 1.5 molar excess, together with 2 mol % of Pd₂(DBA)₃•CHCl₃ and 1.0 equivalents of DIPA•HCl, provided compound 46.

$^1$H NMR (400 MHz, CDCl₃) δ0.15 (s, 9H), 1.30 (d, J=6.1 Hz, 3H), 3.34 (dd, J=18.6, 10.2 Hz, 1H), 3.41 (dd, J=5.4, 3.0 Hz, 1H), 3.52, (dd, J=19.5, 10.0 Hz, 1H), 4.23–4.30 (m, 1H), 4.35–4.42 (m, 1H), 4.49 (s, 1H), 5.26 (ABq, J$_{AB}$=15.6 Hz, ΔυAB=66.7 Hz, 2H), 7.45 (d, J=8.8 Hz, 2H), 7.78–7.87 (m, 2H), 7.90–7.96 (m, 3H), 8.04 (d, J=2.1 Hz, 1H), 8.30 (d, J=8.8 Hz, 1H), 8.45–8.52 (m, 2H), 8.58 (s, 1H), 8.74 (d, J=2.2 Hz, 1H); IR (CHCl₃) 1780, 1720, 1608, 1520 cm$^{-1}$.

EXAMPLE 43

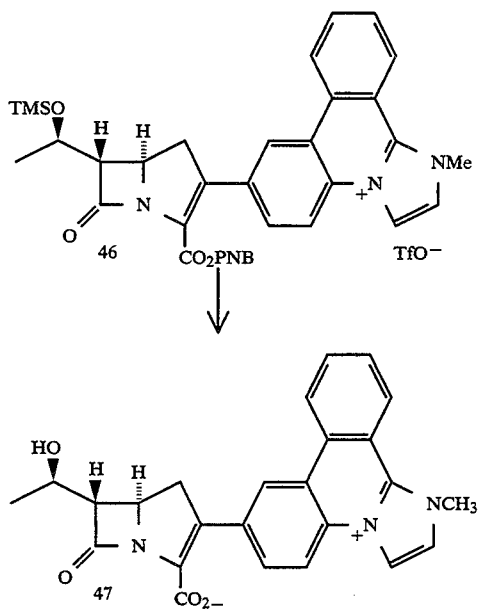

Following the procedure described in Example 4, but substituting carbapenem 46 for carbapenem 5, and using 5% Rh/Al₂O₃ as the catalyst and EtOH/THF/H₂O as the solvent system, provided carbapenem 47.

$^1$H NMR (400 MHz, D₆ DMSO/D₂O) δ1.18 (d, J=6.4 Hz, 2H), 3.14 (dd, J=15.6, 10.2 Hz, 1H), 3.26 (dd, J=6.2, 3.9 Hz, 1H), 3.32 (dd, J=16.9, 8.3 Hz, 1H), 3.92–3.99 (m, 1H), 4.12–4.17 (m, 1H), 4.44 (s, 3H), 7.89–7.92 (m, 1H), 7.97 (d, J=8.4 Hz, 1H), 8.03 (t, J=7.51 Hz, 1H), 8.25 (s, 1H), 8.37 (d, J=8.8 Hz, 1H), 8.72 (d, J=8.1 Hz, 1H), 8.81 (d, J=8.0 Hz, 1H), 8.93 (s, 1H), 9.05 (s, 1H); IR (KBr) 1750, 1600 cm$^{-1}$; UV (MOPS BUFFER λ$_{ext1}$=327 nm, ε$_{ext1}$32 4000; λ$_{ext2}$=343 nm, ε$_{ext2}$32 3200.

What is claimed is:

1. A compound of the formula:

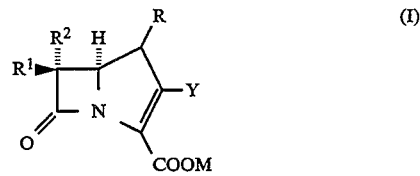

wherein
Y is

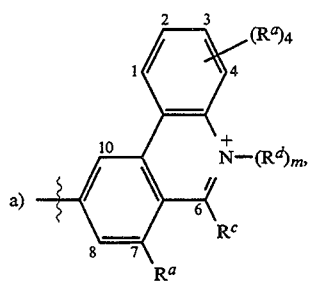

a)

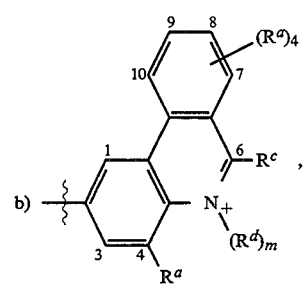

b)

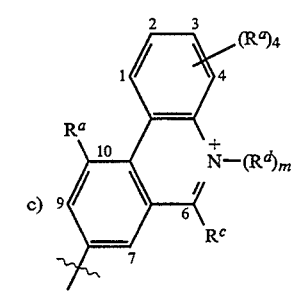

c)

or

-continued

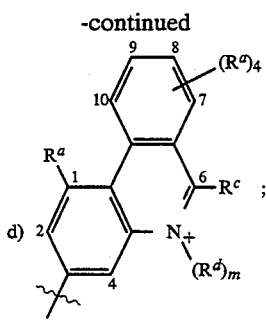

R is H or CH₃;

R¹ and R² are independently H, CH₃—, CH₃CH₂—, (CH₃)₂CH—, HOCH₂—, CH₃CH(OH)—, (CH₃)₂C(OH)—, FCH₂CH(OH)—, F₂CHCH(OH)—, F₃CCH(OH)—, CH₃CH(F)—, CH₃CF₂—, or (CH₃)₂C(F)—;

R^a are independently selected from the group consisting of hydrogen and the radicals set out below, provided that not more than four R^a radicals are other than hydrogen:

a) a trifluoromethyl group: —CF₃;
b) a halogen atom: —Br, —Cl, —F, or —I;
c) C₁–C₄ alkoxy radical: —OC₁₋₄ alkyl, wherein the alkyl is optionally mono-substituted by R^q, where R^q is a member selected from the group consisting of —OH, —OCH₃, —CN, —C(O)NH₂, —OC(O)NH₂, CHO, —OC(O)N(CH₃)₂, —SO₂NH₂, —SO₂N(CH₃)₂, —SOCH₃, —SO₂CH₃, —F, —CF₃, —COOM^a (where M^a is hydrogen, alkali metal, methyl or phenyl), tetrazolyl (where the point of attachment is the carbon atom of the tetrazole ring and one of the nitrogen atoms is mono-substituted by M^a as defined above) and —SO₃M^b (where M^b is hydrogen or an alkali metal);

d) a hydroxy group: —OH;
e) a carbonyloxy radical: —O(C═O)R^s, where

R^s is C₁₋₄ alkyl or phenyl, each of which is optionally mono-substituted by R^q as defined above;

f) a carbamoyloxy radical: —O(C═O)N(R^y)R^z where

R^y and R^z are independently H, C₁₋₄ alkyl (optionally mono-substituted by R^q as defined above), together a 3- to 5-membered alkylidene radical to form a ring (optionally substituted with R^q as defined above) or together a 2- to 4-membered alkylidene radical, interrupted by —O—, —S—, —S(O)— or —S(O)₂— to form a ring (where the ring is optionally mono-substituted with Rq as defined above);

g) a sulfur radical: —S(O)_n—R^s where n=0–2, and R^s is , defined above;
h) a sulfamoyl group: —SO₂N(R^y)R^z where R^y and R^z are as defined above;
i) azido: N₃
j) a formamido group: —N(R^t)(C═O)H, where R^t is H or C₁₋₄ alkyl, and the alkyl thereof is optionally mono-substituted by R^q as defined above;
k) a (C₁–C₄ alkyl)carbonylamino radical: —N(R^t)(C═O)C₁₋₄ alkyl, where R^t is as defined above, and the alkyl group is also optionally mono-substituted by R^q as defined above;
l) a (C₁–C₄ alkoxy) carbonylamino radical: —N(R^t)(C═O)OC₁₋₄ alkyl, where R^t is defined above, and the alkyl group is also optionally mono-substituted by R^q as defined above;
m) a ureido group: —N(R^t)(C═O)N(R^y)R^z where R^t, R^y and R^z are as defined above;
n) a sulfonamido group: —N(R^t)SO₂R^s, where R^s and R^t are as defined above;
o) a cyano group: —CN;
p) a formyl or acetalized formyl radical: —(C═O)H or —CH(OCH₃)₂;
q) (C₁–C₄ alkyl)carbonyl radical wherein the carbonyl is acetalized: —C(OCH₃)₂C₁₋₄ alkyl, where the alkyl is optionally mono-substituted by R^q as defined above;
r) carbonyl radical: —(C═O)R^s, where R^s is as defined above;
s) a hydroximinomethyl radical in which the oxygen or carbon atom is optionally substituted by a C₁–C₄ alkyl group: —(C═NOR^z)R^y where R^y and R^z are as defined above, except they may not be joined together to form a ring;
t) a (C₁–C₄ alkoxy)carbonyl radical: —(C═O)OC₁₋₄ alkyl, where the alkyl is optionally mono-substituted by R^q as defined above;
u) a carbamoyl radical: —(C═O)N(R^y)R^z where R^y and R^z are as defined above;
v) an N-hydroxycarbamoyl or N(C₁–C₄ alkoxy)-carbamoyl radical in which the nitrogen atom may be additionally substituted by a C₁–C₄ alkyl group: —(C═O)—N(OR^y)R^z where R^y and R^z are as defined above, except they may not be joined together to form a ring;
w) a thiocarbamoyl group: —(C═S)N(R^y)(R^z) where R^y and R^z are as defined above;
x) carboxyl: —COOM^b, where M^b is as defined above;
y) thiocyanate: —SCN;
z) trifluoromethylthio: —SCF₃;
aa) tetrazolyl, where the point of attachment is the carbon atom of the tetrazole ring and one of the nitrogen atoms is mono-substituted by hydrogen, an alkali metal or a C₁–C₄ alkyl optionally substituted by R^q as defined above;
ab) an anionic function selected from the group consisting of: phosphono; [P═O(OM^b)₂]; alkylphosphono {P═O(OM^b)-[O(C₁–C₄ alkyl)]}; ; alkylphosphinyl; [P═(OM^b)-(C₁–C₄alkyl)]; phosphoramido [P═O(OM^b)N(R^y)R^z and P═O(OM^b)NHR^x]; sulfino (SO₂M^b); sulfo (SO₃M^b); acylsulfonamides selected from the structures CONM^bSO₂R^x, CONM^bSO₂N(R^y)R^z, SO₂NM^bCON(R^y)R^z; and SO₂NM^bCN, where R^x i s phenyl or heteroaryl, where heteroaryl is a monocyclic aromatic hydrocarbon group having 5 or 6 ring atoms, in which a carbon atom is the point of attachment, in which one of the carbon atoms has been replaced by a nitrogen atom, in which one additional carbon atom is optionally replaced by a heteroatom selected from O or S, and in which from 1 to 2 additional carbon atoms are optionally replaced by a nitrogen heteroatom, and where the phenyl and heteroaryl are optionally mono-substituted by R^q, as defined above; M^b is as defined above; and R^y and R^z are as defined above;

ac) C₅–C₇ cycloalkyl group in which one of the carbon atoms in the ring is replaced by a heteroatom selected from O, S, NH or N(C₁–C₄ alkyl) and in which one additional carbon atom may be replaced by NH or N(C₁–C₄ alkyl), and in which at least one carbon atom adjacent to each nitrogen heteroatom has both of its attached hydrogen atoms replaced by one oxygen thus forming a carbonyl moiety and there are one or two carbonyl moieties present in the ring;

ad) $C_2$-$C_4$ alkenyl radical, optionally mono-substituted by one of the substituents a) to ac) above and phenyl which is optionally substituted by $R^q$ as defined above;

ae) $C_2$-$C_4$ alkynyl radical, optionally mono-substituted by one of the substituents a) to ac) above;

af) $C_1$-$C_4$ alkyl radical;

ag) $C_1$-$C_4$ alkyl mono-substituted by one of the substituents a)-ac) above;

ah) a 2-oxazolidinonyl moiety in which the point of attachment is the nitrogen atom of the oxazolidinone ring, the ring oxygen atom is optionally replaced by a heteroatom selected from —S— and $NR^t$ (where $R^t$ is as defined above) and one of the saturated carbon atoms of the oxazolidinone ring is optionally mono-substituted by one of the substituents a) to ag) above;

ai) an amine group: —$NR^eR^f$, where $R^e$ and $R^f$ are independently H, $C_{1-4}$ alkyl (optionally mono-substituted by $R^q$ as defined above), together a 4- to 5-membered alkylidene radical to form a ring (optionally substituted with $R^q$ as defined above);

$R^c$ is selected from the group consisting of hydrogen and the radicals set out below:

ba) $C_1$-$C_4$ alkyl radical;

bb) $C_1$-$C_4$ alkyl mono-substituted by one of the substituents a)-ac) described hereinabove;

bc) $C_1$-$C_4$ alkoxy radical: —$OC_{1-4}$ alkyl, wherein the alkyl is optionally mono-substituted by $R^q$, where $R^q$ is as described hereinabove; and bd) an amine group: —$NR^gR^h$, where $R^g$ and $R^h$ are independently H, $C_{1-4}$ alkyl (optionally mono-substituted by $R^q$ as defined above), together a 4- to 5-membered alkylidene radical to form a ring (optionally substituted with $R^q$ as defined above) or $R^g$ is combined with $R^d$ to form a diradical selected from the group consisting of: —$CH_2CH_2$—, —$CH_2CH_2CH_2$— and —$CH$=$CH$—;

$R^d$ is —$NH_2$, —$O^-$, $C_1$-$C_4$-alkyl (where the alkyl group is optionally monosubstituted with $R^q$ as defined above), or hydrogen, or $R^d$ is combined with $R^g$ to form a diradical selected from the group consisting of: —$CH_2CH_2$—, —$CH_2CH_2CH_2$— and —$CH$=$CH$—;

provided that $R^d$ is hydrogen only if at least one $R^a$ or $R^c$ is an amine group;

m is 0 to 1, if at least one $R^a$ or $R^c$ is an amine group;

m is 1 if neither $R^a$ nor $R^c$ is an amine group; and

M is selected from:

i) hydrogen;

ii) a pharmaceutically acceptable esterifying group or removable carboxyl protecting group;

iii) an alkali metal or other pharmaceutically acceptable cation; or (iv) a negative charge.

2. The compound of claim 1, wherein $R^1$ is hydrogen and $R^2$ is (R)—$CH_3CH(OH)$— or (R)—$CH_3CH(F)$—.

3. The compound according to claim 1 wherein:

$R^g$ and $R^h$ are independently H, $C_{1-4}$ alkyl (optionally mono-substituted by $R^q$ as defined above) or together are a 4- to 5-membered alkylidene radical forming a ring (optionally substituted with $R^q$ as defined above); and $R^d$ is —$NH_2$, —$O^-$, $C_1$-$C_4$-alkyl (where the alkyl group is optionally monosubstituted with $R^q$ as defined above), or hydrogen;

provided that $R^d$ is hydrogen only if at least one $R^a$ or $R^c$ is an amine group.

4. The compound according to claim 1 wherein:
Y=

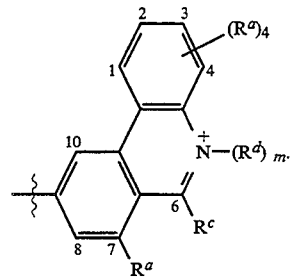

a)

5. The compound according to claim 1 wherein:
Y=

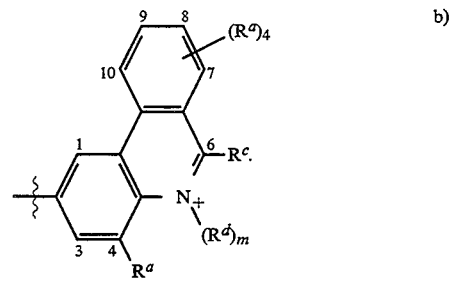

b)

6. The compound according to claim 1, wherein the structural formula is:

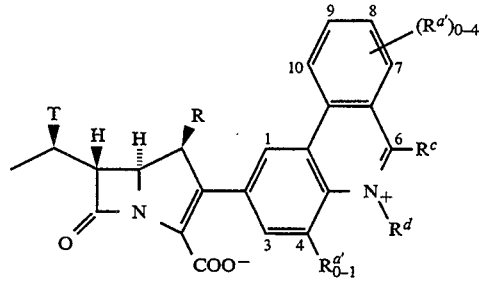

and the substituents $R^{a'}$ (which is $R^a$ when it is not hydrogen), R, $R^c$, $R^d$ and T are as defined in Table I below:

TABLE I

| R | R$^{a'}$ | R$^{a'}$ Position | T | R$^c$ | R$^d$ |
|---|---|---|---|---|---|
| H | —CN | 4 | OH | H | CH$_3$ |
| H | —CONH$_2$ | 4 | OH | H | CH$_3$ |
| H | —CONMe$_2$ | 4 | OH | H | CH$_3$ |
| H | —CHO | 4 | OH | H | CH$_3$ |
| H | —SCH$_3$ | 4 | OH | H | CH$_3$ |
| H | —SOCH$_3$ | 4 | OH | H | CH$_3$ |
| H | —SO$_2$CH$_3$ | 4 | OH | H | CH$_3$ |
| H | —F | 4 | OH | H | CH$_3$ |
| H | —SO$_2$NH$_2$ | 4 | OH | H | CH$_3$ |
| H | —CH$_2$OH | 8 | OH | H | CH$_3$ |
| H | —CN | 8 | OH | H | CH$_3$ |
| H | —CONH$_2$ | 8 | OH | H | CH$_3$ |
| H | —CHO | 8 | OH | H | CH$_3$ |
| H | —CH$_2$OH | 7 | OH | H | CH$_3$ |
| H | —CN | 7 | OH | H | CH$_3$ |
| H | —CONH$_2$ | 7 | OH | H | CH$_3$ |
| H | —CHO | 7 | OH | H | CH$_3$ |
| H | —CN | 4 | F | H | CH$_3$ |
| H | —CHO | 4 | F | H | CH$_3$ |
| H | —CONH$_2$ | 4 | F | H | CH$_3$ |
| CH$_3$ | —CN | 4 | OH | H | CH$_3$ |
| CH$_3$ | —CONH$_2$ | 4 | OH | H | CH$_3$ |
| CH$_3$ | —CHO | 4 | OH | H | CH$_3$ |
| CH$_3$ | —CN | 4 | F | H | CH$_3$ |
| H | —CN | 4 | OH | H | Et |
| H | —CONH$_2$ | 4 | OH | H | Pr |
| H | —CONH$_2$ | 4 | OH | H | Bu |
| H | —CF$_3$ | 8 | OH | H | CH$_3$ |
| H | —OCH$_3$ | 9 | OH | H | CH$_3$ |
| H | —OCH$_2$CO$_2$CH$_3$ | 10 | OH | H | CH$_3$ |
| H | —Cl | 4, 7, 8 | OH | H | CH$_3$ |
| H | —OH | 9 | OH | H | CH$_3$ |
| H | —OCOCH$_3$ | 8 | OH | H | CH$_3$ |
| H | —OCONH$_2$ | 8 | OH | H | CH$_3$ |
| H | —SCH$_2$CH$_2$OH | 8 | OH | H | CH$_3$ |
| H | —SOCH$_2$CH$_2$OH | 9 | OH | H | CH$_3$ |
| H | —SCH$_2$CONH$_2$ | 4 | OH | H | CH$_3$ |
| H | —SO$_2$NMe$_2$ | 4, 8 | OH | H | CH$_3$ |
| H | —NHCHO | 8 | OH | H | CH$_3$ |
| H | — | | OH | —NHCH$_2$CONH$_2$ | CH$_3$ |
| H | — | | OH | —N(CH$_3$)$_2$ | CH$_3$ |
| H | — | | F | —N(CH$_3$)$_2$ | CH$_3$ |
| CH$_3$ | — | | OH | —N(CH$_3$)$_2$ | CH$_3$ |
| H | —CH$_2$OH | 8 | OH | H | O$^-$ |
| H | —CH$_2$OH | 8 | OH | H | NH$_2$ |
| H | —CH$_2$OH | 8 | OH | H | CH$_2$CH$_2$OH |
| H | —CH$_2$OH | 8 | OH | H | CH$_2$CH$_2$CH$_2$CN |
| H | —NHCOCH$_3$ | 9 | OH | H | CH$_3$ |
| H | —NHCOCH$_3$ | 10 | OH | H | CH$_3$ |
| H | —NHSO$_2$CH$_3$ | 4 | OH | H | CH$_3$ |
| H | —COMe | 4 | OH | H | CH$_3$ |
| H | —COCH$_2$OH | 7 | OH | H | CH$_3$ |
| H | —CH=NOH | 8 | OH | H | CH$_3$ |
| H | —CH=NOMe | 7 | OH | H | CH$_3$ |
| H | —CH=NOCH$_2$CO$_2$Me | 8 | OH | H | CH$_3$ |
| H | —CH=NOCMe$_2$CO$_2$Me | 8 | OH | H | CH$_3$ |
| H | —CH=NOCMe$_2$CONH$_2$ | 9 | OH | H | CH$_3$ |
| H | —CO$_2$CH$_2$CH$_2$OH | 10 | OH | H | CH$_3$ |
| H | —CONHCH$_3$ | 4 | OH | H | CH$_3$ |
| H | —CONHCH$_2$CN | 4 | OH | H | CH$_3$ |
| H | —CONHCH$_2$CN | 4 | F | H | CH$_3$ |
| CH$_3$ | —CONHCH$_2$CN | 4 | OH | H | CH$_3$ |
| H | —CONHCH$_2$CONH$_2$ | 8 | OH | H | CH$_3$ |
| H | —CONHCH$_2$CO$_2$CH$_3$ | 9 | OH | H | CH$_3$ |
| H | —CONHOH | 4 | OH | H | CH$_3$ |
| H | —CONHOCH$_3$ | 10 | OH | H | CH$_3$ |
| H | —CO$_2$CH$_3$ | 4 | OH | H | CH$_3$ |
| H | -tetrazolyl | 8 | OH | H | CH$_3$ |
| H | —SCF$_3$ | 4 | OH | H | CH$_3$ |
| H | —PO$_2$NH$_2$ | 4 | OH | H | CH$_3$ |
| H | —CONHSO$_2$Ph | 4 | OH | H | CH$_3$ |
| H | —CONHSO$_2$NH$_2$ | 4 | OH | H | CH$_3$ |
| H | —SO$_2$CF$_3$ | 8 | OH | H | CH$_3$ |
| H | —SO$_2$NHCN | 4 | OH | H | CH$_3$ |
| H | —SO$_2$NHCONH$_2$ | 4 | OH | H | CH$_3$ |
| H | —CH=CHCN | 4 | OH | H | CH$_3$ |
| H | —CH=CHCONH$_2$ | 4 | OH | H | CH$_3$ |
| H | —C≡C—CN | 4 | OH | H | CH$_3$ |
| H | —CH$_2$N$_3$ | 7 | OH | H | CH$_3$ |
| H | —CH$_2$CO$_2$Me | 10 | OH | H | CH$_3$ |

TABLE I-continued

| R | $R^{a'}$ | $R^{a'}$ Position | T | $R^c$ | $R^d$ |
|---|---|---|---|---|---|
| H | —SO$_2$CH$_2$CH$_2$OH | 4 | OH | H | CH$_3$ |
| H | —CH$_2$I | 8 | OH | H | CH$_3$ |
| H | —I | 4 | OH | H | CH$_3$ |
| H | —Br | 4 | OH | H | CH$_3$ |
| H | — | | OH | H | CH$_2$CH$_2$CH$_3$ |
| H | — | | OH | OCH$_3$ | CH$_3$ |
| H | — | | OH | NHCH$_2$CH$_2$OH | CH$_3$ |
| H | — | | OH | N-pyrrolidinyl | CH$_3$ or |
| H | — | | OH | NH$_2$ | H. |

7. The compound according to claim 1, wherein the structural formula is:

and the substituents $R^{a'}$ (which is $R^a$ when it is not hydrogen), R, $R^c$, $R^d$ and T are as defined in Table II below:

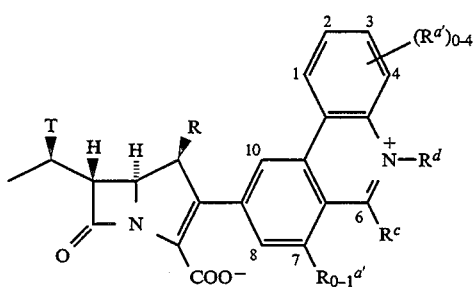

TABLE II

| R | $R^{a'}$ | $R^{a'}$ Position | T | $R^c$ | $R^d$ |
|---|---|---|---|---|---|
| H | —CN | 7 | OH | H | CH$_3$ |
| H | —CONH$_2$ | 7 | OH | H | CH$_3$ |
| H | —CONMe$_2$ | 7 | OH | H | CH$_3$ |
| H | —CHO | 7 | OH | H | CH$_3$ |
| H | —SCH$_3$ | 7 | OH | H | CH$_3$ |
| H | —SOCH$_3$ | 7 | OH | H | CH$_3$ |
| H | —SO$_2$CH$_3$ | 7 | OH | H | CH$_3$ |
| H | —F | 7 | OH | H | CH$_3$ |
| H | —SO$_2$NH$_2$ | 7 | OH | H | CH$_3$ |
| H | —CH$_2$OH | 3 | OH | H | CH$_3$ |
| H | —CN | 3 | OH | H | CH$_3$ |
| H | —CONH$_2$ | 3 | OH | H | CH$_3$ |
| H | —CHO | 3 | OH | H | CH$_3$ |
| H | —CH$_2$OH | 4 | OH | H | CH$_3$ |
| H | —CN | 4 | OH | H | CH$_3$ |
| H | —CONH$_2$ | 4 | OH | H | CH$_3$ |
| H | —CHO | 4 | OH | H | CH$_3$ |
| H | —CN | 7 | F | H | CH$_3$ |
| H | —CHO | 7 | F | H | CH$_3$ |
| H | —CONH$_2$ | 7 | F | H | CH$_3$ |
| CH$_3$ | —CN | 7 | OH | H | CH$_3$ |
| CH$_3$ | —CONH$_2$ | 7 | OH | H | CH$_3$ |
| CH$_3$ | —CHO | 7 | OH | H | CH$_3$ |
| CH$_3$ | —CN | 7 | F | H | CH$_3$ |
| H | —CN | 7 | OH | H | Et |
| H | —CONH$_2$ | 7 | OH | H | Pr |
| H | —CONH$_2$ | 7 | OH | H | Bu |
| H | —CF$_3$ | 3 | OH | H | CH$_3$ |
| H | —OCH$_3$ | 2 | OH | H | CH$_3$ |
| H | —OCH$_2$CO$_2$CH$_3$ | 1 | OH | H | CH$_3$ |
| H | —Cl | 3, 4, 7 | OH | H | CH$_3$ |
| H | —OH | 2 | OH | H | CH$_3$ |
| H | —OCOCH$_3$ | 3 | OH | H | CH$_3$ |
| H | —OCONH$_2$ | 3 | OH | H | CH$_3$ |
| H | —SCH$_2$CH$_2$OH | 3 | OH | H | CH$_3$ |
| H | —SOCH$_2$CH$_2$OH | 2 | OH | H | CH$_3$ |
| H | —SCH$_2$CONH$_2$ | 7 | OH | H | CH$_3$ |
| H | —SO$_2$NMe$_2$ | 7, 3 | OH | H | CH$_3$ |
| H | —NHCHO | 3 | OH | H | CH$_3$ |

TABLE II-continued

| R | $R^{a'}$ | $R^{a'}$ Position | T | $R^c$ | $R^d$ |
|---|---|---|---|---|---|
| H | — | | OH | —NHCH$_2$CONH$_2$ | CH$_3$ |
| H | — | | OH | —N(CH$_3$)$_2$ | CH$_3$ |
| H | — | | F | —N(CH$_3$)$_2$ | CH$_3$ |
| CH$_3$ | — | | OH | —N(CH$_3$)$_2$ | CH$_3$ |
| H | —CH$_2$OH | 3 | OH | H | O$^-$ |
| H | —CH$_2$OH | 3 | OH | H | NH$_2$ |
| H | —CH$_2$OH | 3 | OH | H | CH$_2$CH$_2$OH |
| H | —CH$_2$OH | 3 | OH | H | CH$_2$CH$_2$CH$_2$CN |
| H | —NHCOCH$_3$ | 2 | OH | H | CH$_3$ |
| H | —NHCOCH$_3$ | 1 | OH | H | CH$_3$ |
| H | —NHSO$_2$CH$_3$ | 7 | OH | H | CH$_3$ |
| H | —COMe | 7 | OH | H | CH$_3$ |
| H | —COCH$_2$OH | 4 | OH | H | CH$_3$ |
| H | —CH=NOH | 3 | OH | H | CH$_3$ |
| H | —CH=NOMe | 4 | OH | H | CH$_3$ |
| H | —CH=NOCH$_2$CO$_2$Me | 3 | OH | H | CH$_3$ |
| H | —CH=NOCMe$_2$CO$_2$Me | 3 | OH | H | CH$_3$ |
| H | —CH=NOCMe$_2$CONH$_2$ | 2 | OH | H | CH$_3$ |
| H | —CO$_2$CH$_2$CH$_2$OH | 1 | OH | H | CH$_3$ |
| H | —CONHCH$_3$ | 7 | OH | H | CH$_3$ |
| H | —CONHCH$_2$CN | 7 | OH | H | CH$_3$ |
| H | —CONHCH$_2$CN | 7 | F | H | CH$_3$ |
| CH$_3$ | —CONHCH$_2$CN | 7 | OH | H | CH$_3$ |
| H | —CONHCH$_2$CONH$_2$ | 3 | OH | H | CH$_3$ |
| H | —CONHCH$_2$CO$_2$CH$_3$ | 2 | OH | H | CH$_3$ |
| H | —CONHOH | 7 | OH | H | CH$_3$ |
| H | —CONHOCH$_3$ | 1 | OH | H | CH$_3$ |
| H | —CO$_2$CH$_3$ | 7 | OH | H | CH$_3$ |
| H | -tetrazolyl | 3 | OH | H | CH$_3$ |
| H | —SCF$_3$ | 7 | OH | H | CH$_3$ |
| H | —PO$_2$NH$_2$ | 7 | OH | H | CH$_3$ |
| H | —CONHSO$_2$Ph | 7 | OH | H | CH$_3$ |
| H | —CONHSO$_2$NH$_2$ | 7 | OH | H | CH$_3$ |
| H | —SO$_2$CF$_3$ | 3 | OH | H | CH$_3$ |
| H | —SO$_2$NHCN | 7 | OH | H | CH$_3$ |
| H | —SO$_2$NHCONH$_2$ | 7 | OH | H | CH$_3$ |
| H | —CH=CHCN | 7 | OH | H | CH$_3$ |
| H | —CH=CHCONH$_2$ | 7 | OH | H | CH$_3$ |
| H | —C≡C—CN | 7 | OH | H | CH$_3$ |
| H | —CH$_2$N$_3$ | 4 | OH | H | CH$_3$ |
| H | —CH$_2$CO$_2$Me | 1 | OH | H | CH$_3$ |
| H | —SO$_2$CH$_2$CH$_2$OH | 7 | OH | H | CH$_3$ |
| H | —CH$_2$I | 3 | OH | H | CH$_3$ |
| H | —I | 7 | OH | H | CH$_3$ |
| H | —Br | 7 | OH | H | CH$_3$ |
| H | — | | OH | H | CH$_2$CH$_2$CH$_3$ |
| H | — | | OH | OCH$_3$ | CH$_3$ |
| H | — | | OH | NHCH$_2$CH$_2$OH | CH$_3$ |
| H | — | | OH | N-pyrrolidinyl | CH$_3$ or |
| H | — | | OH | NH$_2$ | H. |

8. The compound according to claim 1, wherein the structural formula is:

and the substituents $R^{a'}$ (which is $R^a$ when it is not hydrogen), R, $R^c$, $R^d$ and T are as defined in Table III below:

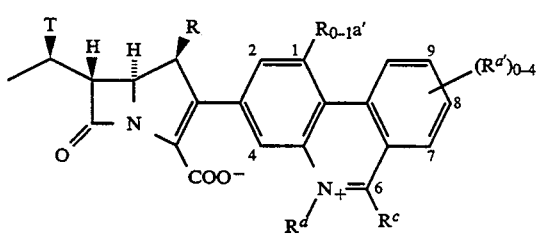

TABLE III

| R | $R^{a'}$ | $R^{a'}$ Position | T | $R^c$ | $R^d$ |
|---|---|---|---|---|---|
| H | —CN | 1 | OH | H | CH$_3$ |

TABLE III-continued

| R | $R^{a'}$ | $R^{a'}$ Position | T | $R^c$ | $R^d$ |
|---|---|---|---|---|---|
| H | —CONH$_2$ | 1 | OH | H | CH$_3$ |
| H | —CONMe$_2$ | 1 | OH | H | CH$_3$ |
| H | —CHO | 1 | OH | H | CH$_3$ |
| H | —SCH$_3$ | 1 | OH | H | CH$_3$ |
| H | —SOCH$_3$ | 1 | OH | H | CH$_3$ |
| H | —SO$_2$CH$_3$ | 1 | OH | H | CH$_3$ |
| H | —F | 1 | OH | H | CH$_3$ |
| H | —SO$_2$NH$_2$ | 1 | OH | H | CH$_3$ |
| H | —CH$_2$OH | 8 | OH | H | CH$_3$ |
| H | —CN | 8 | OH | H | CH$_3$ |
| H | —CONH$_2$ | 8 | OH | H | CH$_3$ |
| H | —CHO | 8 | OH | H | CH$_3$ |
| H | —CH$_2$OH | 7 | OH | H | CH$_3$ |
| H | —CN | 7 | OH | H | CH$_3$ |
| H | —CONH$_2$ | 7 | OH | H | CH$_3$ |
| H | —CHO | 7 | OH | H | CH$_3$ |
| H | —CN | 1 | F | H | CH$_3$ |
| H | —CHO | 1 | F | H | CH$_3$ |
| H | —CONH$_2$ | 1 | F | H | CH$_3$ |
| CH$_3$ | —CN | 1 | OH | H | CH$_3$ |
| CH$_3$ | —CONH$_2$ | 1 | OH | H | CH$_3$ |
| CH$_3$ | —CHO | 1 | OH | H | CH$_3$ |
| CH$_3$ | —CN | 1 | F | H | CH$_3$ |
| H | —CN | 1 | OH | H | Et |
| H | —CONH$_2$ | 1 | OH | H | Pr |
| H | —CONH$_2$ | 1 | OH | H | Bu |
| H | —CF$_3$ | 8 | OH | H | CH$_3$ |
| H | —OCH$_3$ | 9 | OH | H | CH$_3$ |
| H | —OCH$_2$CO$_2$CH$_3$ | 10 | OH | H | CH$_3$ |
| H | —Cl | 1,7,8 | OH | H | CH$_3$ |
| H | —OH | 9 | OH | H | CH$_3$ |
| H | —OCOCH$_3$ | 8 | OH | H | CH$_3$ |
| H | —OCONH$_2$ | 8 | OH | H | CH$_3$ |
| H | —SCH$_2$CH$_2$OH | 8 | OH | H | CH$_3$ |
| H | —SOCH$_2$CH$_2$OH | 9 | OH | H | CH$_3$ |
| H | —SCH$_2$CONH$_2$ | 1 | OH | H | CH$_3$ |
| H | —SO$_2$NMe$_2$ | 1,8 | OH | H | CH$_3$ |
| H | —NHCHO | 8 | OH | H | CH$_3$ |
| H | — | | OH | —NHCH$_2$CONH$_2$ | CH$_3$ |
| H | — | | OH | —N(CH$_3$)$_2$ | CH$_3$ |
| H | — | | F | —N(CH$_3$)$_2$ | CH$_3$ |
| CH$_3$ | — | | OH | —N(CH$_3$)$_2$ | CH$_3$ |
| H | —CH$_2$OH | 8 | OH | H | O$^-$ |
| H | —CH$_2$OH | 8 | OH | H | NH$_2$ |
| H | —CH$_2$OH | 8 | OH | H | CH$_2$CH$_2$OH |
| H | —CH$_2$OH | 8 | OH | H | CH$_2$CH$_2$CH$_2$CN |
| H | —NHCOCH$_3$ | 9 | OH | H | CH$_3$ |
| H | —NHCOCH$_3$ | 10 | OH | H | CH$_3$ |
| H | —NHSO$_2$CH$_3$ | 1 | OH | H | CH$_3$ |
| H | —COMe | 1 | OH | H | CH$_3$ |
| H | —COCH$_2$OH | 7 | OH | H | CH$_3$ |
| H | —CH=NOH | 8 | OH | H | CH$_3$ |
| H | —CH=NOMe | 7 | OH | H | CH$_3$ |
| H | —CH=NOCH$_2$CO$_2$Me | 8 | OH | H | CH$_3$ |
| H | —CH=NOCM$_{e2}$CO$_2$Me | 8 | OH | H | CH$_3$ |
| H | —CH=NOCMe$_2$CONH$_2$ | 9 | OH | H | CH$_3$ |
| H | —CO$_2$CH$_2$CH$_2$OH | 10 | OH | H | CH$_3$ |
| H | —CONHCH$_3$ | 1 | OH | H | CH$_3$ |
| H | —CONHCH$_2$CN | 1 | OH | H | CH$_3$ |
| H | —CONHCH$_2$CN | 1 | F | H | CH$_3$ |
| CH$_3$ | —CONHCH$_2$CN | 1 | OH | H | CH$_3$ |
| H | —CONHCH$_2$CONH$_2$ | 8 | OH | H | CH$_3$ |
| H | —CONHCH$_2$CO$_2$CH$_3$ | 9 | OH | H | CH$_3$ |
| H | —CONHOH | 1 | OH | H | CH$_3$ |
| H | —CONHOCH$_3$ | 10 | OH | H | CH$_3$ |
| H | —CO$_2$CH$_3$ | 1 | OH | H | CH$_3$ |
| H | -tetrazolyl | 8 | OH | H | CH$_3$ |
| H | —SCF$_3$ | 1 | OH | H | CH$_3$ |
| H | —PO$_2$NH$_2$ | 1 | OH | H | CH$_3$ |
| H | —CONHSO$_2$Ph | 1 | OH | H | CH$_3$ |
| H | —CONHSO$_2$NH$_2$ | 1 | OH | H | CH$_3$ |
| H | —SO$_2$CF$_3$ | 8 | OH | H | CH$_3$ |
| H | —SO$_2$NHCN | 1 | OH | H | CH$_3$ |
| H | —SO$_2$NHCONH$_2$ | 1 | OH | H | CH$_3$ |
| H | —CH=CHCN | 1 | OH | H | CH$_3$ |
| H | —CH=CHCONH$_2$ | 1 | OH | H | CH$_3$ |
| H | —C≡C—CN | 1 | OH | H | CH$_3$ |
| H | —CH$_2$N$_3$ | 7 | OH | H | CH$_3$ |
| H | —CH$_2$CO$_2$Me | 10 | OH | H | CH$_3$ |
| H | —SO$_2$CH$_2$CH$_2$OH | 1 | OH | H | CH$_3$ |

TABLE III-continued

| R | $R^{a'}$ | $R^{a'}$ Position | T | $R^c$ | $R^d$ |
|---|---|---|---|---|---|
| H | —CH$_2$I | 8 | OH | H | CH$_3$ |
| H | —I | 1 | OH | H | CH$_3$ |
| H | —Br | 1 | OH | H | CH$_3$ |
| H | — |  | OH | H | CH$_2$CH$_2$CH$_3$ |
| H | — |  | OH | OCH$_3$ | CH$_3$ |
| H | — |  | OH | NHCH$_2$CH$_2$OH | CH$_3$ |
| H | — |  | OH | N-pyrrolidinyl | CH$_3$ or |
| H | — |  | OH | NH$_2$ | H. |

9. The compound according to claim 1, wherein the structural formula is:

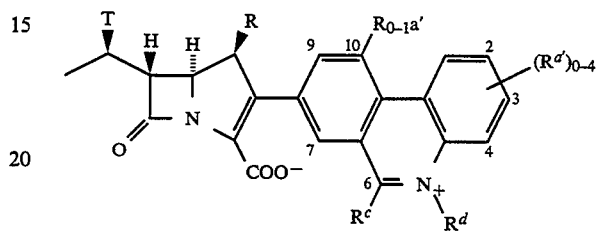

and the substituents $R^{a'}$ (which is $R^a$ when it is not hydrogen), R, $R^c$, $R^d$ and T are as defined in Table IV below:

TABLE IV

| R | $R^{a'}$ | $R^{a'}$ Position | T | $R^c$ | $R^d$ |
|---|---|---|---|---|---|
| H | —CN | 7 | OH | H | CH$_3$ |
| H | —CONH$_2$ | 10 | OH | H | CH$_3$ |
| H | —CONMe$_2$ | 10 | OH | H | CH$_3$ |
| H | —CHO | 10 | OH | H | CH$_3$ |
| H | —SCH$_3$ | 10 | OH | H | CH$_3$ |
| H | —SOCH$_3$ | 10 | OH | H | CH$_3$ |
| H | —SO$_2$CH$_3$ | 10 | OH | H | CH$_3$ |
| H | —F | 10 | OH | H | CH$_3$ |
| H | —SO$_2$NH$_2$ | 10 | OH | H | CH$_3$ |
| H | —CH$_2$OH | 3 | OH | H | CH$_3$ |
| H | —CN | 3 | OH | H | CH$_3$ |
| H | —CONH$_2$ | 3 | OH | H | CH$_3$ |
| H | —CHO | 3 | OH | H | CH$_3$ |
| H | —CH$_2$OH | 4 | OH | H | CH$_3$ |
| H | —CN | 4 | OH | H | CH$_3$ |
| H | —CONH$_2$ | 4 | OH | H | CH$_3$ |
| H | —CHO | 4 | OH | H | CH$_3$ |
| H | —CN | 10 | F | H | CH$_3$ |
| H | —CHO | 10 | F | H | CH$_3$ |
| H | —CONH$_2$ | 10 | F | H | CH$_3$ |
| CH$_3$ | —CN | 10 | OH | H | CH$_3$ |
| CH$_3$ | —CONH$_2$ | 10 | OH | H | CH$_3$ |
| CH$_3$ | —CHO | 10 | OH | H | CH$_3$ |
| CH$_3$ | —CN | 10 | F | H | CH$_3$ |
| H | —CN | 10 | OH | H | Et |
| H | —CONH$_2$ | 10 | OH | H | Pr |
| H | —CONH$_2$ | 10 | OH | H | Bu |
| H | —CF$_3$ | 3 | OH | H | CH$_3$ |
| H | —OCH$_3$ | 2 | OH | H | CH$_3$ |
| H | —OCH$_2$CO$_2$CH$_3$ | 1 | OH | H | CH$_3$ |
| H | —Cl | 3,4,10 | OH | H | CH$_3$ |
| H | —OH | 2 | OH | H | CH$_3$ |
| H | —OCOCH$_3$ | 3 | OH | H | CH$_3$ |
| H | —OCONH$_2$ | 3 | OH | H | CH$_3$ |
| H | —SCH$_2$CH$_2$OH | 3 | OH | H | CH$_3$ |
| H | —SOCH$_2$CH$_2$OH | 2 | OH | H | CH$_3$ |
| H | —SCH$_2$CONH$_2$ | 10 | OH | H | CH$_3$ |
| H | —SO$_2$NMe$_2$ | 10,3 | OH | H | CH$_3$ |
| H | —NHCHO | 3 | OH | H | CH$_3$ |
| H | — |  | OH | —NHCH$_2$CONH$_2$ | CH$_3$ |
| H | — |  | OH | —N(CH$_3$)$_2$ | CH$_3$ |
| H | — |  | F | —N(CH$_3$)$_2$ | CH$_3$ |
| CH$_3$ | — |  | OH | —N(CH$_3$)$_2$ | CH$_3$ |
| H | —CH$_2$OH | 3 | OH | H | O$^-$ |
| H | —CH$_2$OH | 3 | OH | H | NH$_2$ |
| H | —CH$_2$OH | 3 | OH | H | CH$_2$CH$_2$OH |
| H | —CH$_2$OH | 3 | OH | H | CH$_2$CH$_2$CH$_2$CN |

TABLE IV-continued

| R | R$^{a'}$ | R$^{a'}$ Position | T | R$^c$ | R$^d$ |
|---|---|---|---|---|---|
| H | —NHCOCH$_3$ | 2 | OH | H | CH$_3$ |
| H | —NHCOCH$_3$ | 1 | OH | H | CH$_3$ |
| H | —NHSO$_2$CH$_3$ | 10 | OH | H | CH$_3$ |
| H | —COMe | 10 | OH | H | CH$_3$ |
| H | —COCH$_2$OH | 4 | OH | H | CH$_3$ |
| H | —CH=NOH | 3 | OH | H | CH$_3$ |
| H | —CH=NOMe | 4 | OH | H | CH$_3$ |
| H | —CH=NOCH$_2$CO$_2$Me | 3 | OH | H | CH$_3$ |
| H | —C=NOCMe$_2$CO$_2$Me | 3 | OH | H | CH$_3$ |
| H | —CH=NOCMe$_2$CONH$_2$ | 2 | OH | H | CH$_3$ |
| H | —CO$_2$CH$_2$CH$_2$OH | 1 | OH | H | CH$_3$ |
| H | —CONHCH$_3$ | 10 | OH | H | CH$_3$ |
| H | —CONHCH$_2$CN | 10 | OH | H | CH$_3$ |
| H | —CONHCH$_2$CN | 10 | F | H | CH$_3$ |
| CH$_3$ | —CONHCH$_2$CN | 10 | OH | H | CH$_3$ |
| H | —CONHCH$_2$CONH$_2$ | 3 | OH | H | CH$_3$ |
| H | —CONHCH$_2$CO$_2$CH$_3$ | 2 | OH | H | CH$_3$ |
| H | —CONHOH | 10 | OH | H | CH$_3$ |
| H | —CONHOCH$_3$ | 1 | OH | H | CH$_3$ |
| H | —CO$_2$CH$_3$ | 10 | OH | H | CH$_3$ |
| H | -tetrazolyl | 3 | OH | H | CH$_3$ |
| H | —SCF$_3$ | 10 | OB | H | CH$_3$ |
| H | —PO$_2$NH$_2$ | 10 | OH | H | CH$_3$ |
| H | —CONHSO$_2$Ph | 10 | OH | H | CH$_3$ |
| H | —CONHSO$_2$NH$_2$ | 10 | OH | H | CH$_3$ |
| H | —SO$_2$CF$_3$ | 3 | OH | H | CH$_3$ |
| H | —SO$_2$NHCN | 10 | OH | H | CH$_3$ |
| H | —SO$_2$NHCONH$_2$ | 10 | OH | H | CH$_3$ |
| H | —CH=CHCN | 10 | OH | H | CH$_3$ |
| H | —CH=CHCONH$_2$ | 10 | OH | H | CH$_3$ |
| H | —C≡C—CN | 10 | OH | H | CH$_3$ |
| H | —CH$_2$N$_3$ | 4 | OH | H | CH$_3$ |
| H | —CH$_2$CO$_2$Me | 1 | OH | H | CH$_3$ |
| H | —SO$_2$CH$_2$CH$_2$OH | 10 | OH | H | CH$_3$ |
| H | —CH$_2$I | 3 | OH | H | CH$_3$ |
| H | —I | 10 | OH | H | CH$_3$ |
| H | —Br | 10 | OH | H | CH$_3$ |
| H | — | | OH | H | CH$_2$CH$_2$CH$_3$ |
| H | — | | OH | OCH$_3$ | CH$_3$ |
| H | — | | OH | NHCH$_2$CH$_2$OH | CH$_3$ |
| H | — | | OH | N-pyrrolidinyl | CH$_3$ or |
| H | — | | OH | NH$_2$ | H. |

10. A compound according to claim 4 wherein the structural formula is:

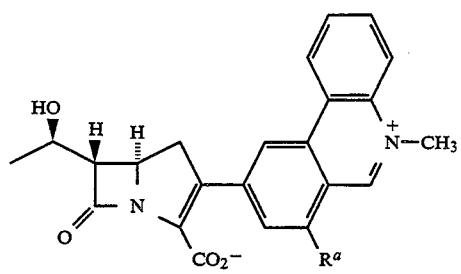

and the R$^a$ substituent is selected from CH$_2$OH, CO$_2$CH$_3$, CONH$_2$, Cl, CN, CHO, SCH$_3$, SCH$_2$CH$_2$OH and SO$_2$CH$_3$.

11. A compound according to claim 5 wherein the structural formula is:

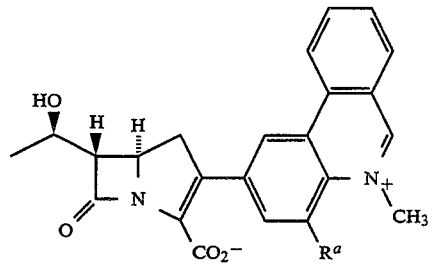

and the R$^a$ substituent is selected from CH$_2$OH, CO$_2$CH$_3$, CONH$_2$, Cl, CN, CHO, SCH$_3$, SCH$_2$CH$_2$OH and SO$_2$CH$_3$.

12. A compound according to claim 1 wherein the structural formula is:

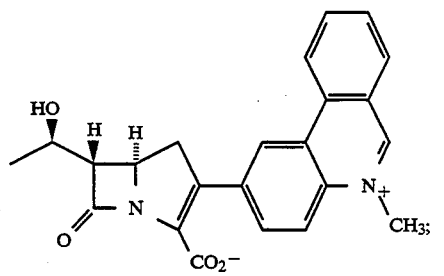

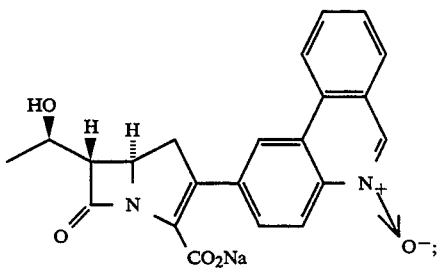

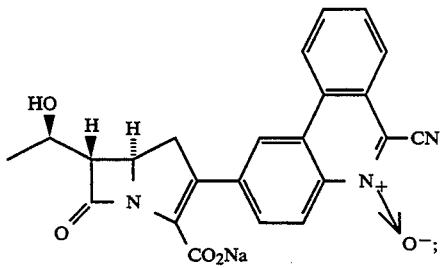

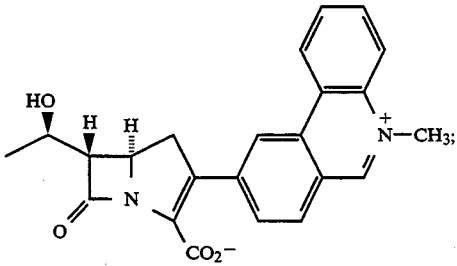

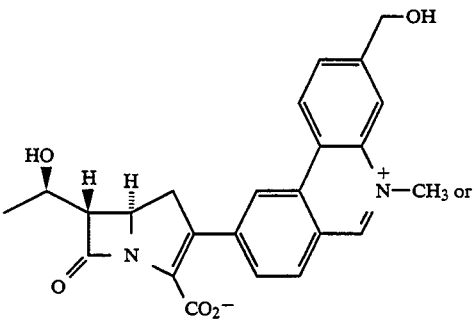

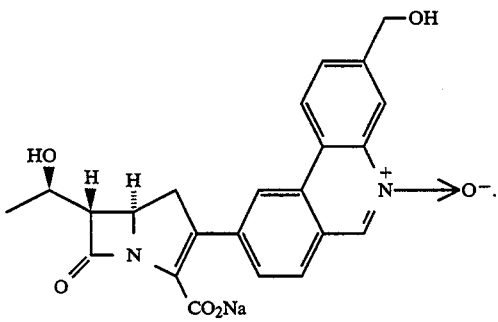

13. A compound according to claim 1 wherein the structural formula is:

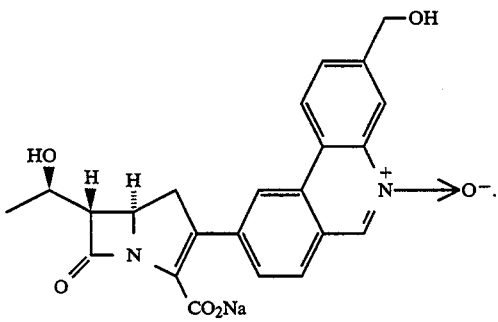

14. A pharmaceutical composition for antibacterial use comprising an antibacterially effective amount of a compound of claim 1 and a pharmaceutically acceptable carrier.

15. A method of treating bacterial infections in human or animal subjects in need of such treatment comprising administering to such subject an antibacterially effective amount of a compound of claim 1.

16. A pharmaceutical composition for antibacterial use comprising an antibacterially effective amount of a compound of claim 1, an inhibitorily effective amount of a dehydropeptidase (DHP) inhibitor, and optionally, a pharmaceutically acceptable carrier.

17. A pharmaceutical composition according to claim 16, wherein the DHP inhibitor is 7-(L-2-amino-2-carboxyethylthio)-2-(2,2-dimethylcyclopropanecarboxamide)-2-heptenoic acid.

18. A method of treating bacterial infections in human or animal subjects in need of such treatment comprising coadministering to such subject an antibacterially effective amount of a compound of claim 1 and an inhibitorily effective amount of a DHP inhibitor.

19. The method according to claim 18, wherein the DHP inhibitor is 7-(L-2-amino-2-carboxyethylthio)-2-(2,2-dimethylcyclopropanecarboxamide)-2heptenoic acid.

* * * * *

UNITED STATES PATENT AND TRADEMARK OFFICE
CERTIFICATE OF CORRECTION

PATENT NO. : 5,336,674
DATED : August 9, 1994
INVENTOR(S) : F. P. DiNinno et al.

It is certified that error appears in the above-indentified patent and that said Letters Patent is hereby corrected as shown below:

In Column 63, line 55, replace the phrase "m is O to 1" with the phrase -- m is O or 1 --.

At Column 69, between lines 53-65 in claim 8, please replace the structure with the following:

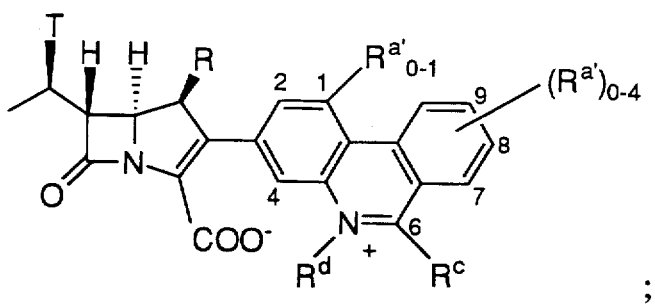

;

UNITED STATES PATENT AND TRADEMARK OFFICE
CERTIFICATE OF CORRECTION

PATENT NO. : 5,336,674
DATED : August 9, 1994
INVENTOR(S) : F.P. DiNinno et al.

It is certified that error appears in the above-indentified patent and that said Letters Patent is hereby corrected as shown below:

At Column 74, lines 15-23 in Claim 9, please replace the structure with the following;

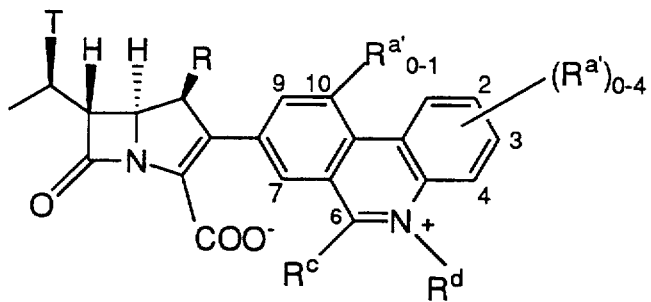

Signed and Sealed this

Twenty-seventh Day of December, 1994

Attest:

BRUCE LEHMAN

*Attesting Officer*       *Commissioner of Patents and Trademarks*